(12) United States Patent
Adler et al.

(10) Patent No.: US 12,408,963 B2
(45) Date of Patent: Sep. 9, 2025

(54) MEDICAL DEVICE FOR IMPLANTING IN BONEY TISSUE AND CHARACTERIZATION OF BONE FRACTURES

(71) Applicant: CANARY MEDICAL SWITZERLAND AG, Baar (CH)

(72) Inventors: Mark A. Adler, Carlsbad, CA (US); Steven Cazarez, San Diego, CA (US); Paul Charlesbois, Victoria (CA); Jeffrey M. Gross, Carlsbad, CA (US); Joshua Ben Hayes, Victoria (CA); Paul Alexander Hulme, Victoria (CA); Luke Aaron Mills, Victoria (CA); Tuyen Nguyen, Victoria (CA); Timothy Park, Victoria (CA); Aaron Olafur Laurence Philippsen, Victoria (CA); Peter J. Schiller, San Marcos, CA (US); Diego Ariel Sorrentino, Victoria (CA)

(73) Assignee: Canary Medical Switzerland AG, Baar (CH)

( * ) Notice: Subject to any disclaimer, the term of this patent is extended or adjusted under 35 U.S.C. 154(b) by 0 days.

(21) Appl. No.: 17/801,195

(22) PCT Filed: Feb. 19, 2021

(86) PCT No.: PCT/US2021/018892
§ 371 (c)(1),
(2) Date: Aug. 19, 2022

(87) PCT Pub. No.: WO2021/168337
PCT Pub. Date: Aug. 26, 2021

(65) Prior Publication Data
US 2023/0346440 A1  Nov. 2, 2023

Related U.S. Application Data

(60) Provisional application No. 63/120,158, filed on Dec. 1, 2020, provisional application No. 62/979,349, filed on Feb. 20, 2020.

(51) Int. Cl.
*A61B 17/86* (2006.01)
*A61B 5/00* (2006.01)
*A61B 17/72* (2006.01)

(52) U.S. Cl.
CPC ........ *A61B 17/8685* (2013.01); *A61B 5/4504* (2013.01); *A61B 5/4851* (2013.01);
(Continued)

(58) Field of Classification Search
CPC ... A61B 5/0031; A61B 5/4504; A61B 5/4851; A61B 5/6878; A61B 17/72; A61B 17/864; A61B 17/8685
See application file for complete search history.

(56) References Cited

U.S. PATENT DOCUMENTS

| | | |
|---|---|---|
| 4,411,266 A | 10/1983 | Cosman |
| 6,139,581 A | 10/2000 | Engh et al. |

(Continued)

FOREIGN PATENT DOCUMENTS

| | | |
|---|---|---|
| CN | 1899222 A | 1/2007 |
| CN | 101257860 A | 9/2008 |

(Continued)

OTHER PUBLICATIONS

Extended European Search Report for European Application No. 15842678.3, mailed Feb. 5, 2019, 13 Pages.
(Continued)

*Primary Examiner* — Larry E Waggle, Jr.

(57) ABSTRACT

A smart medical device includes a structure configured to be at least partially implanted in a body, and an electronics cartridge that is configured to be inserted into the structure after the structure is implanted in the body. The structure may be a cannulated screw for use in treating bone fractures. The medical device includes an impedance sensor for monitoring and reporting on the healing state of bone fractures.

(Continued)

The sensor includes components of the electronics cartridge and electrodes that are either associated with the cannulated screw or with the insertable electronics cartridge.

8 Claims, 41 Drawing Sheets

(52) U.S. Cl.
CPC .......... *A61B 5/6847* (2013.01); *A61B 5/6878* (2013.01); *A61B 17/72* (2013.01); *A61B 17/864* (2013.01)

(56) References Cited

U.S. PATENT DOCUMENTS

| | | | |
|---|---|---|---|
| 6,499,488 | B1 | 12/2002 | Hunter et al. |
| 6,706,071 | B1 | 3/2004 | Wolter |
| 7,009,511 | B2 | 3/2006 | Mazar et al. |
| 7,130,695 | B2 | 10/2006 | Czygan et al. |
| 7,384,403 | B2 | 6/2008 | Sherman |
| 7,938,831 | B2 * | 5/2011 | Leroux .................. A61B 17/70 606/86 R |
| 8,075,627 | B2 | 12/2011 | Caylor, III et al. |
| 8,374,697 | B2 * | 2/2013 | Berger ............... A61B 17/8605 607/51 |
| 8,556,888 | B2 | 10/2013 | Nields et al. |
| 8,668,742 | B2 | 3/2014 | Caylor, III et al. |
| 8,695,432 | B2 * | 4/2014 | Hsieh .................... F16B 31/025 606/301 |
| 9,019,098 | B2 | 4/2015 | Okano |
| 9,445,930 | B2 | 9/2016 | Chen et al. |
| 9,451,919 | B2 | 9/2016 | Roche |
| 9,456,915 | B2 | 10/2016 | Chen et al. |
| 9,949,669 | B2 | 4/2018 | DiSilvestro et al. |
| 10,070,973 | B2 | 9/2018 | Sherman et al. |
| 10,219,699 | B2 | 3/2019 | Wilder et al. |
| 10,285,637 | B1 | 5/2019 | Hnat et al. |
| 10,582,891 | B2 | 3/2020 | Wiedenhoefer et al. |
| 10,898,106 | B2 | 1/2021 | Bodewes et al. |
| 11,684,260 | B2 | 6/2023 | Wiedenhoefer et al. |
| 2002/0024450 | A1 | 2/2002 | Townsend et al. |
| 2002/0147416 | A1 | 10/2002 | Zogbi et al. |
| 2003/0069644 | A1 | 4/2003 | Kovacevic et al. |
| 2003/0204267 | A1 | 10/2003 | Hazebrouck et al. |
| 2004/0011137 | A1 | 1/2004 | Hnat et al. |
| 2004/0019382 | A1 | 1/2004 | Amirouche et al. |
| 2004/0019384 | A1 | 1/2004 | Kirking et al. |
| 2004/0204766 | A1 | 10/2004 | Siebel |
| 2004/0211580 | A1 | 10/2004 | Wang et al. |
| 2004/0249464 | A1 | 12/2004 | Bindseil et al. |
| 2004/0249471 | A1 | 12/2004 | Bindseil et al. |
| 2006/0009856 | A1 | 1/2006 | Sherman et al. |
| 2006/0030771 | A1 | 2/2006 | Levine et al. |
| 2006/0030945 | A1 | 2/2006 | Wright |
| 2006/0047283 | A1 | 3/2006 | Evans, III et al. |
| 2006/0111777 | A1 | 5/2006 | Chen |
| 2006/0142670 | A1 | 6/2006 | Disilvestro et al. |
| 2006/0200121 | A1 | 9/2006 | Mowery |
| 2006/0224088 | A1 | 10/2006 | Roche |
| 2006/0229730 | A1 | 10/2006 | Railey et al. |
| 2006/0271199 | A1 | 11/2006 | Johnson |
| 2007/0004994 | A1 | 1/2007 | Sherman |
| 2007/0005141 | A1 | 1/2007 | Sherman |
| 2007/0089518 | A1 | 4/2007 | Ericson et al. |
| 2007/0233065 | A1 | 10/2007 | Donofrio et al. |
| 2007/0239282 | A1 | 10/2007 | Caylor, III et al. |
| 2007/0265662 | A1 | 11/2007 | Ufford |
| 2008/0027679 | A1 | 1/2008 | Shklarski |
| 2008/0033527 | A1 | 2/2008 | Nunez et al. |
| 2008/0076972 | A1 | 3/2008 | Dorogusker et al. |
| 2008/0172106 | A1 | 7/2008 | McGinnis et al. |
| 2008/0255556 | A1 | 10/2008 | Berger |
| 2008/0300597 | A1 | 12/2008 | Morgan et al. |
| 2008/0306325 | A1 | 12/2008 | Burnett et al. |
| 2009/0012372 | A1 | 1/2009 | Burnett et al. |
| 2009/0048524 | A1 | 2/2009 | Wildau et al. |
| 2009/0088756 | A1 | 4/2009 | Anderson |
| 2009/0118804 | A1 | 5/2009 | Moffitt et al. |
| 2009/0157146 | A1 | 6/2009 | Linder et al. |
| 2009/0192533 | A1 | 7/2009 | Dlugos, Jr. et al. |
| 2009/0253587 | A1 | 10/2009 | Fernandez |
| 2010/0191100 | A1 | 7/2010 | Anderson et al. |
| 2010/0204551 | A1 | 8/2010 | Roche |
| 2010/0204802 | A1 | 8/2010 | Wilson et al. |
| 2011/0004076 | A1 | 1/2011 | Janna et al. |
| 2011/0019595 | A1 | 1/2011 | Magar et al. |
| 2011/0054272 | A1 | 3/2011 | Derchak |
| 2011/0087306 | A1 | 4/2011 | Goossen |
| 2011/0208161 | A1 | 8/2011 | Ivri |
| 2011/0288436 | A1 | 11/2011 | Stone |
| 2011/0319755 | A1 | 12/2011 | Stein et al. |
| 2012/0123498 | A1 | 5/2012 | Gross |
| 2012/0226360 | A1 | 9/2012 | Stein et al. |
| 2013/0079675 | A1 | 3/2013 | Stein et al. |
| 2013/0079679 | A1 | 3/2013 | Roche et al. |
| 2013/0123684 | A1 | 5/2013 | Giuffrida et al. |
| 2013/0144379 | A1 | 6/2013 | Najafi et al. |
| 2013/0225949 | A1 | 8/2013 | Roche |
| 2014/0135589 | A1 | 5/2014 | Osorio |
| 2014/0275849 | A1 | 9/2014 | Acquista |
| 2014/0275861 | A1 | 9/2014 | Kroh et al. |
| 2014/0296663 | A1 | 10/2014 | Boyden et al. |
| 2014/0379090 | A1 | 12/2014 | Diomidis et al. |
| 2015/0238304 | A1 | 8/2015 | Lamraoui |
| 2016/0101281 | A1 | 4/2016 | Chen |
| 2016/0128573 | A1 | 5/2016 | Wilder et al. |
| 2016/0310066 | A1 | 10/2016 | Wiedenhoefer et al. |
| 2017/0035593 | A1 | 2/2017 | Chen et al. |
| 2017/0119566 | A1 | 5/2017 | Chen et al. |
| 2018/0228428 | A1 | 8/2018 | Anker et al. |
| 2019/0150882 | A1 | 5/2019 | Maharbiz et al. |
| 2019/0231555 | A1 | 8/2019 | Neubardt |
| 2019/0247197 | A1 | 8/2019 | Jagannathan et al. |
| 2020/0054215 | A1 | 2/2020 | Roche |
| 2020/0155327 | A1 | 5/2020 | Suh et al. |
| 2021/0077241 | A1 | 3/2021 | Hunter |
| 2022/0387186 | A1 | 12/2022 | Golemon, Jr. et al. |
| 2023/0301802 | A1 | 9/2023 | Trousdale et al. |
| 2024/0156396 | A1 | 5/2024 | Amiot et al. |

FOREIGN PATENT DOCUMENTS

| | | |
|---|---|---|
| CN | 101495025 A | 7/2009 |
| CN | 101773387 A | 7/2010 |
| CN | 202036215 U | 11/2011 |
| CN | 102740803 A | 10/2012 |
| CN | 102885626 A | 1/2013 |
| CN | 103313661 A | 9/2013 |
| CN | 103458830 A | 12/2013 |
| CN | 103735303 A | 4/2014 |
| CN | 103957992 A | 7/2014 |
| DE | 4322619 C1 | 9/1994 |
| DE | 10342823 A1 | 4/2005 |
| JP | 2009505751 A | 2/2009 |
| JP | 2022128381 A | 9/2022 |
| WO | 2006108065 A2 | 10/2006 |
| WO | 2008032316 A2 | 3/2008 |
| WO | 2012095784 A1 | 7/2012 |
| WO | 2015021807 A1 | 2/2015 |
| WO | 2015200720 A2 | 12/2015 |
| WO | 2015200722 A2 | 12/2015 |
| WO | 2017030900 A1 | 2/2017 |

OTHER PUBLICATIONS

International Preliminary Report on Patentability for International Application No. PCT/US2015/050789, mailed Mar. 30, 2017, 07 Pages.

International Preliminary Report on Patentability for International Application No. PCT/US2021/018892, mailed Sep. 1, 2022, 24 Pages.

(56) References Cited

OTHER PUBLICATIONS

International Search Report and Written Opinion for International Application No. PCT/US2015/050789, mailed Feb. 1, 2016, 10 Pages.

Partial Supplementary European Search Report for European Application No. 15842678.3, mailed Oct. 16, 2018, 15 Pages.

Xiang X., et al., "A Review of the Implantable Electronic Devices in Biology and Medicine," China Academic Journal Electronic Publishing House, vol. 32 (3), Mar. 3, 2004, pp. 462-467.

Yiming L., et al., "Application of Wireless Sensor Networks in Healthcare," Chinese Journal of Medical Instrumentation, vol. 37, No. 5, Dec. 31, 2013, pp. 351-354 and Figure 1.

International Search Report and Written Opinion dated Jul. 16, 2021, for International Application No. PCT/US2021/018892.

European Search Report for European Patent Application No. 24205658.8, dated Feb. 28, 2025, 9 Pages.

Supplementary European Search Report for European Patent Application No. 21756273.5, dated Sep. 23, 2024, 10 Pages.

\* cited by examiner

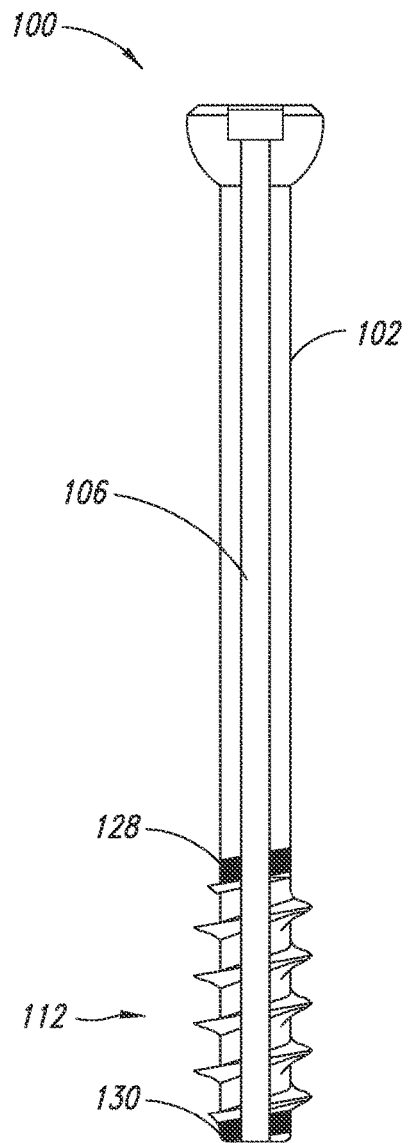
FIG. 1A
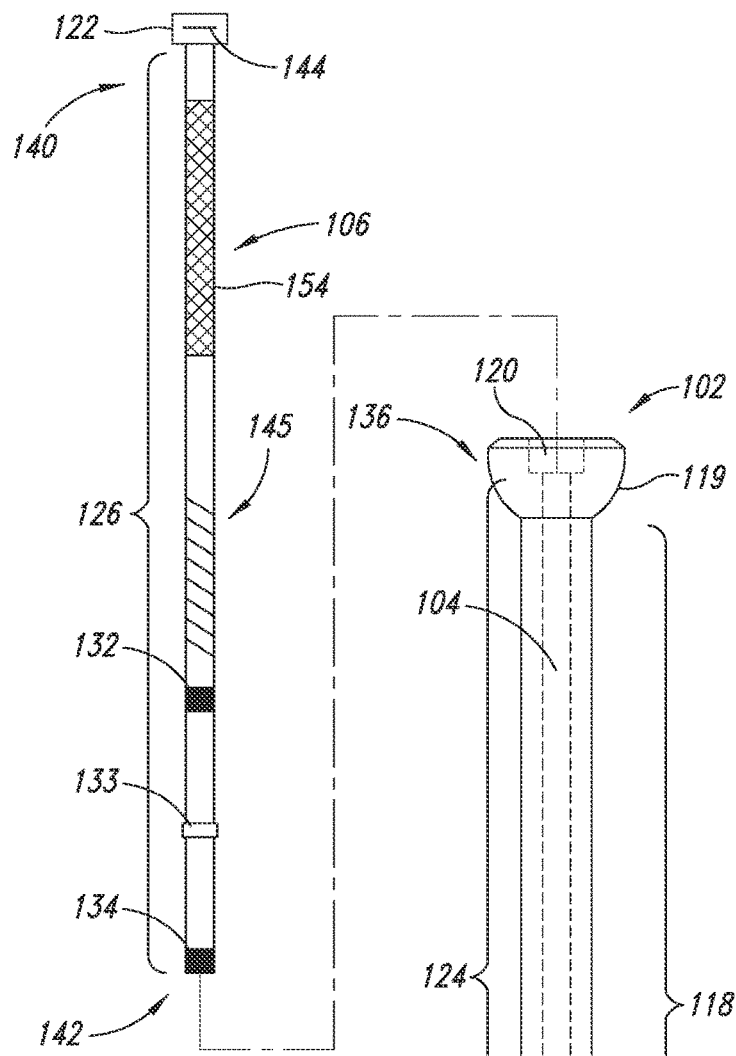
FIG. 1C
FIG. 1B

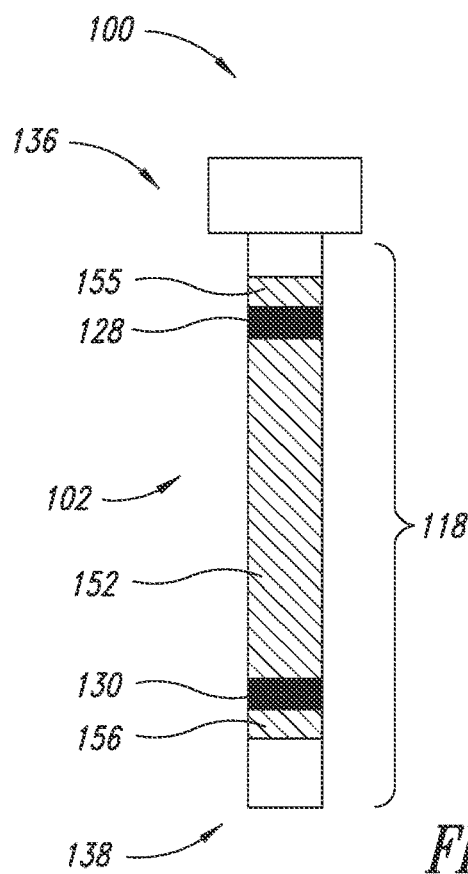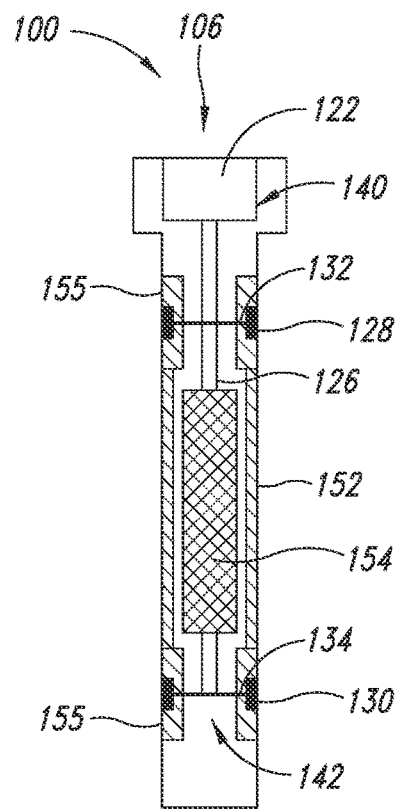
FIG. 7A  FIG. 7B
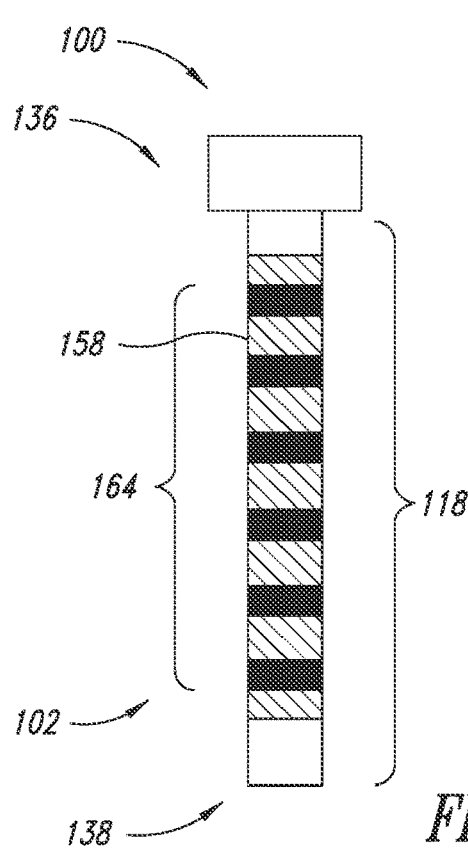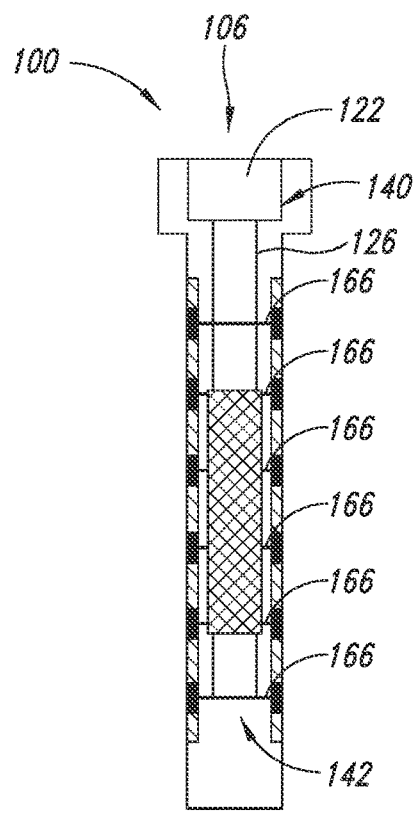
FIG. 8A  FIG. 8B

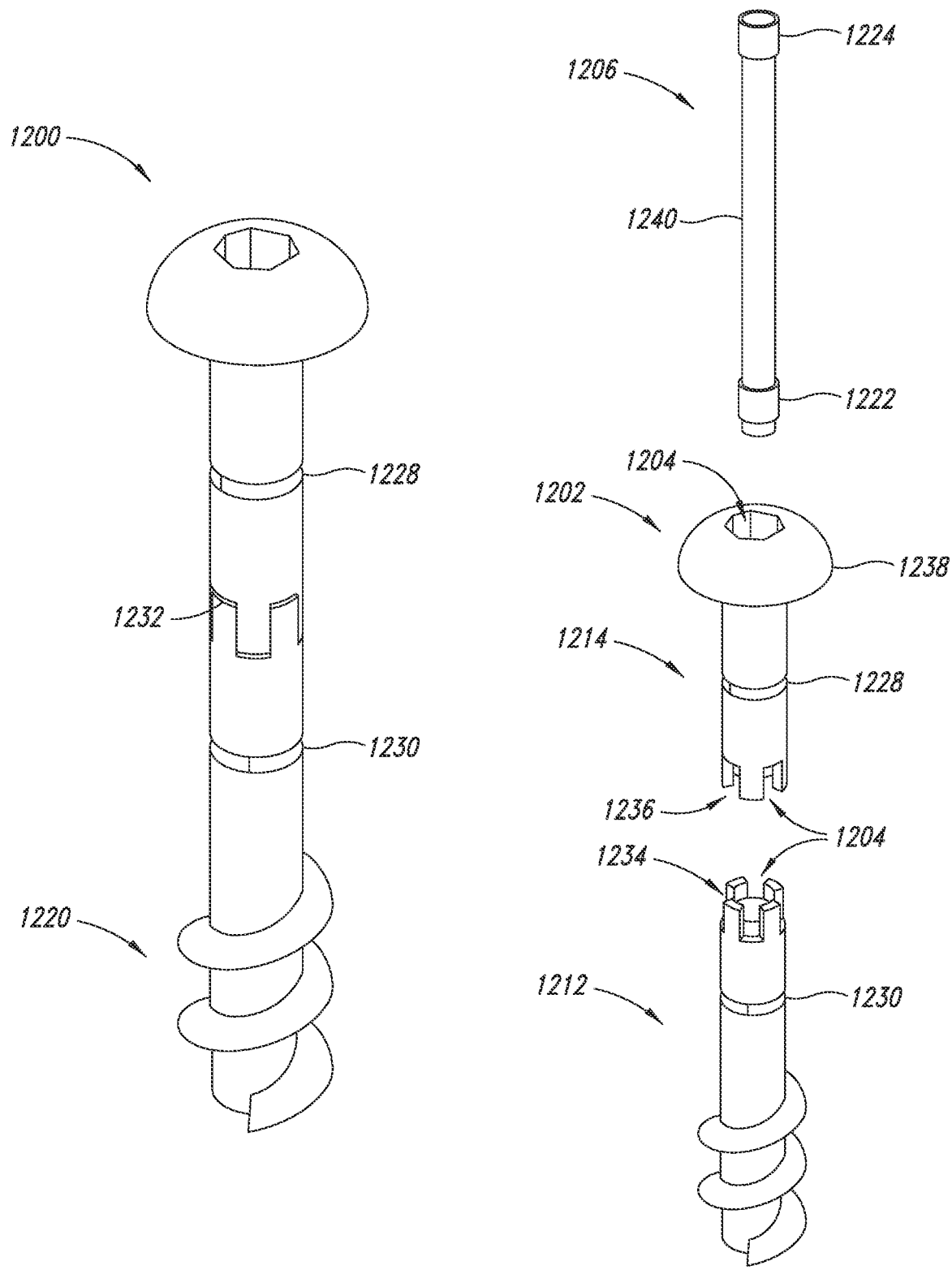
*FIG. 12A*  *FIG. 12B*

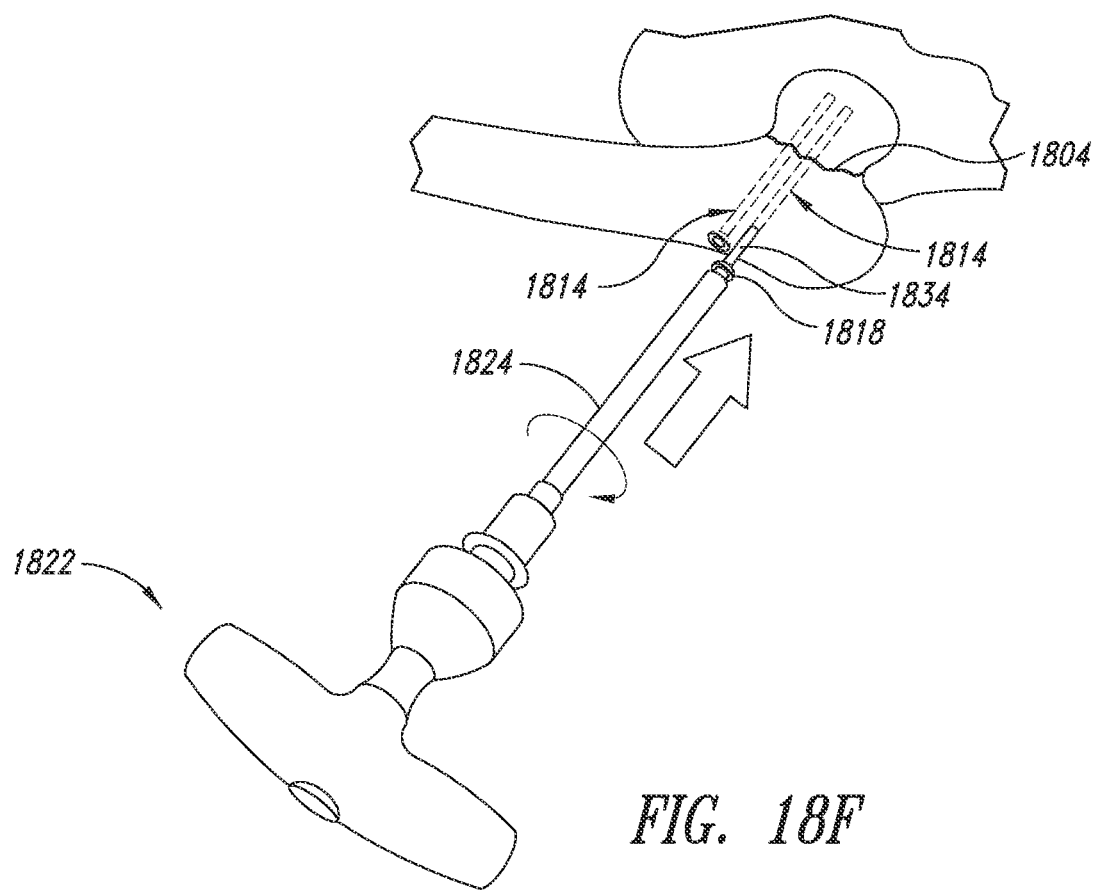
FIG. 18F
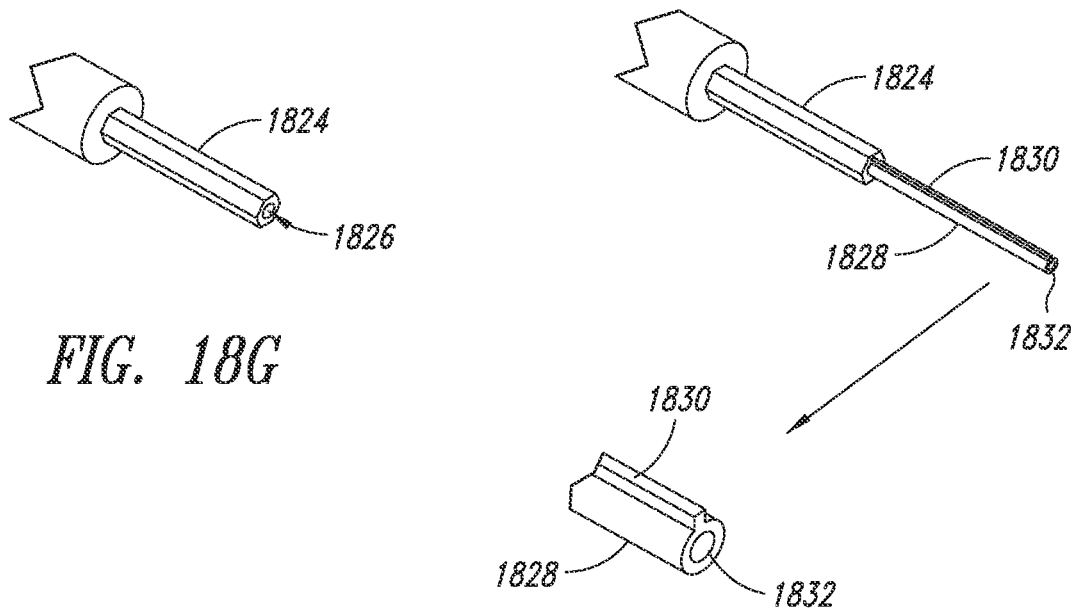
FIG. 18G
FIG. 18H

MEDICAL DEVICE FOR IMPLANTING IN BONEY TISSUE AND CHARACTERIZATION OF BONE FRACTURES

CROSS-REFERENCE TO RELATED APPLICATIONS

This application claims the benefit under 35 U.S.C. § 119 (e) of U.S. Provisional Patent Application No. 63/120,158 filed Dec. 1, 2020, and of U.S. Provisional Patent Application No. 62/979,349, filed Feb. 20, 2020, where these provisional applications are incorporated herein by reference in their entirety for all purposes.

TECHNICAL FIELD

The present disclosure relates generally to medical devices having a structure configured to extend at least partially into boney tissue. For example, the structure may be a screw, a pin, a rod, a nail, a part of a joint replacement implant (e.g., hip, shoulder, knee, etc.), a part of a spinal fixation device, or a part of other orthopedic devices. The medical device includes a sensor for obtaining measurements indicative of the healing state of fractured boney tissue within which the device is implanted, and communication circuitry for communicating such measurements to an external device.

BACKGROUND

A reliable assessment of bone healing is fundamental for the successful treatment of bone fractures. Delayed or non-union fractures have a high incidence, up to 5-10%, and can be very painful and dangerous for the patient health and furthermore lead to unavoidable high costs. Current techniques for monitoring fracture healing rely on non-invasive imaging modalities, such as X-ray, CT scans, ultrasound, and magnetic resonance imaging (MRI). Traditional reliance on radiographs to monitor union has limitations as bridging callus of long bone fractures can take three or more months to occur. Computed tomographic (CT) scanning is a popular modality and can evaluate bridging callus in the late stages of healing to confirm union. The use of dynamic contrast enhanced MRI and advances in nuclear imaging may yield benefits in the assessment of the infected nonunion. Emerging evidence supports the use of ultrasound to detect bridging callus prior to radiographic confirmation and it may be of use to predict patients at high risk of nonunion. Each of these techniques, however, tends to be most useful at later stages of healing and their effectiveness depends on patient compliance in presenting themselves for periodic imaging.

It is therefore desirable to provide a technique for characterizing the state of a bone fracture throughout all stages of healing and in an automatic way that does not depend on imaging or patient compliance. The concepts disclosed herein address these needs and others.

SUMMARY

Briefly stated, the present disclosure relates to a medical device, optionally referred to herein as an implantable and/or smart medical device or the like, a method of manufacture of the medical device, a method of use of the medical device including, e.g., a method of treatment with the medical device and a method of characterizing a healing with the medical device, and other aspects as disclosed herein. The medical device generally has a structure configured to extend at least partially into boney tissue. For example, the structure may be a screw, a pin, a rod, a nail, a part of a joint replacement implant (e.g., hip, shoulder, knee, etc.), a part of a spinal fixation device, or a part of other orthopedic devices. In one embodiment, the medical device is a screw. The implantable smart medical device includes a sensor for obtaining one or more measurements indicative, e.g., of the healing state of fractured boney tissue within which the device is implanted, and communication circuitry for communicating such measurements to an external device.

For example, in one aspect the present disclosure provides a smart medical device that includes a structure configured to be at least partially implanted in a body, and an electronics cartridge that is configured to be inserted into the structure after the structure is implanted in the body. The structure may be a cannulated screw for use in treating bone fractures. The medical device includes an impedance sensor for monitoring and reporting on the healing state of bone fractures. The sensor includes components of the electronics cartridge and electrodes that are either associated with the cannulated screw or with the insertable electronics cartridge.

In one aspect, the present disclosure relates to a medical device that includes a structure having a lumen extending at least partially therethrough and an insertable electronics cartridge including electronics. The structure is configured to be at least partially implanted in a body, and the electronics cartridge is configured to be inserted into the lumen after implant of the structure.

The present disclosure also relates to a medical device that includes a cannulated structure having a plurality of electrodes at an outer surface of the structure, and an insertable electronics cartridge. The cannulated structure has a lumen extending therethrough and is configured to be at least partially implanted in a body. The electronics cartridge includes electronics and is configured to be inserted into the lumen of the cannulated structure such that one or more electrical couplings between the electronics and the plurality of electrodes are established upon such insertion.

The present disclosure also relates to a medical device that includes a cannulated structure having least one aperture through a sidewall of the structure, and an insertable electronics cartridge. The cannulated structure has a lumen extending therethrough and is configured to be at least partially implanted in a body. The electronics cartridge includes a plurality of electrodes and electronics electrically coupled to the electrodes. The electronics cartridge is configured to be inserted into the lumen, and to provide alignment between the plurality of electrodes and the at least one aperture upon such insertion.

The present disclosure also relates to a medical device that includes a cannulated structure having a distal end opening and a proximal end opening, and an insertable electronics cartridge. The cannulated structure has a lumen extending therethrough and is configured to be at least partially implanted in a body. The electronics cartridge includes a plurality of electrodes and electronics electrically coupled to the electrodes. The electronics cartridge is configured to be inserted into the lumen, and to position a first electrode of the plurality of electrodes at the distal end opening of the cannulated structure and a second electrode of the plurality of electrodes at the proximal end opening upon such insertion.

The present disclosure also relates to a medical device that includes a short, cannulated structure having a distal end opening and a proximal end opening, and an insertable electronics cartridge. The cannulated structure has a lumen extending therethrough and is configured to be at least partially implanted in a body. The electronics cartridge includes a plurality of electrodes and electronics electrically coupled to the electrodes. The electronics cartridge is configured to be inserted into the lumen, and to position the plurality of electrodes beyond the distal end opening of the cannulated structure upon such insertion.

The present disclosure also relates to a medical device that is preloaded with electronics. The medical device is configured to be at least partially implanted in a body, and includes a structure having a head and a shaft, each respectively defining a head cavity and a shaft cavity. The preloaded medical device also includes electronics located in one or more of the head cavity and the shaft cavity, and at least one electrode that is associated with the shaft and is electrically coupled to the electronics.

The present disclosure also relates to a medical device that includes a cannulated structure preloaded with an electronics cartridge. The cannulated structure is configured to be implanted in a body and includes a lumen extending at least partially therethrough. The electronics cartridge is at least partially within the lumen and is permanently secured therein. The cannulated structure has a plurality of apertures through a sidewall, and a plurality of electrodes each associated with one of the plurality of apertures. The electronics cartridge includes electronics, and a plurality of electrical contacts each aligned with one of the apertures to establish an electrical coupling between the electronics and each of the plurality of electrodes.

In one aspect, the medical device of the present disclosure may be used to assist in treating a fracture in boney tissue. For example, the medical device may be in the form of a screw that is placed across a fracture in boney tissue, where the screw aids in holding together the bone tissue adjacent to the boney fraction and thus provides a stability function for the healing bone. Optionally, the medical device has little or no stability function but instead is implanted in fractured boney tissue, optionally across a fracture in boney tissue, primarily or solely in order to characterize the bone fracture during the healing process, and thus provides a characterization function. Optionally, the implanted medical device provides both stability function and characterization function. Particularly in the case where the medical device of the present disclosure provides little or no stability function, the medical device of the present disclosure may be utilized in association with other medical devices, e.g., standard orthopedic screws which do not contain a sensor, which primarily provide a stability function. Thus, in one aspect, the present disclosure provides a set of medical devices, where at least one member of the set is a smart medical device of the present disclosure which provides characterization function (and optionally some stability function), and at least one member of the set is utilized to provide primarily or exclusively stability function. In use, the smart medical device of the present disclosure may be placed in boney tissue at a location where stability function is not necessary, i.e., at a non-loaded location. The medical devices that are utilized to provide primarily or exclusively stability function, may be placed at loaded locations in the boney tissue.

The present disclosure also relates to an implantable medical device for characterizing a bone fracture in a bone. The medical device includes an implant configured to be at least partially implanted in the bone and across the bone fracture. The implant includes an impedance sensor that includes a first electrode and a second electrode, and a sensing module configured to obtain impedance measurements between the first electrode and the second electrode. The implant also includes a controller and memory that are configured to process and store the impedance measurements, and communication circuitry that is configured to transmit the impedance measurements to an external device.

The present disclosure also relates to an implantable medical device for characterizing a bone fracture in a bone. The medical device includes a first implant and a second implant, each configured to be at least partially implanted in the bone, and a third implant configured to be placed adjacent the bone across the bone fracture and secured in place by the first implant and the second implant. The first implant has a first electrode, and the second implant has a second electrode. The medical device also has an impedance sensor that includes the first electrode and the second electrode and a sensing module. The sensing module is included in one or more of the first, second, or third implants and is configured to obtain impedance measurements between the first electrode and the second electrode. The medical device also includes a controller and memory that is configured to process and store the impedance measurements, and communication circuitry that is configured to transmit the impedance measurements to an external device. The controller, memory, and communication circuitry may be included in one or more of the first, second, or third implants.

The present disclosure also relates to a method of characterizing a bone fracture through electrodes on opposite sides of the bone fracture. The method includes obtaining a plurality of measures of an electrical property of tissue overtime through a plurality of electrodes associated with a single implant and located in a boney tissue and across the bone fracture. The plurality of electrodes include a first electrode and a second electrode on opposite sides of the bone fracture. The method also includes processing the measures to determine a characterization of the bone fracture, the characterization corresponding to a healing state of the bone fracture.

The present disclosure also relates to a method of characterizing a bone fracture through electrodes within a gap of the bone fracture. The method includes obtaining a plurality of measures of an electrical property of tissue overtime through a plurality of electrodes associated with a single implant and located in a boney tissue at the bone fracture. The plurality of electrodes include a first electrode and a second electrode, each within a gap of the bone fracture. The method also includes processing the measures to determine a characterization of the bone fracture, the characterization corresponding to a healing state of the bone fracture.

The present disclosure also relates to a method of characterizing a bone fracture through electrodes that span a gap of the bone fracture. The method includes obtaining a plurality of measures of an electrical property of tissue overtime through a plurality of electrodes located in a boney tissue at the bone fracture. The plurality of electrodes including a first electrode and a second electrode, each spanning a gap of the bone fracture. The method also includes processing the measures to determine a characterization of the bone fracture, the characterization corresponding to a healing state of the bone fracture.

The present disclosure also relates to a method of manufacturing an implantable medical device. The method includes creating a plurality of apertures through a sidewall of a cannulated structure configured to be at least partially implanted in a body and having a lumen extending therethrough. The method also includes associating an electrode with each of the plurality of apertures, and associating an electronics cartridge with the lumen of the cannulated structure. The electronics cartridge includes electronics and a plurality of electrical contacts, wherein the association aligns each of the plurality of electrical contacts with one of the apertures to establish an electrical coupling between the electronics and each electrode.

The present disclosure also relates to a method of implanting a medical device. The method includes implanting an implant structure at least partially in a body. The structure has a lumen extending at least partially therethrough. The method also includes inserting an electronics cartridge into the lumen after implanting the implant structure.

The present disclosure also relates to a tool for implanting an implant structure having a proximal end having a head, a shaft extending from the head to a distal end of the implant structure, and a lumen extending through the shaft. The tool includes a drill bit, and a mechanism for applying rotational torque to the drill bit. The drill bit includes a first portion configured to directly couple to the head of the implant structure, and a second portion extending from the first portion. The second portion is configured to extend at least partially into the lumen of the implant structure.

The present disclosure also relates to a coupling device for implanting an implant structure having a proximal end having a head, and a shaft extending from the head to a distal end of the implant structure. The coupling device includes a body having a proximal end region and a distal end region. The distal end region is configured to establish a mechanical coupling to a distal end portion of the implant structure. The coupling device may also include a cap configured to the couple to the proximal end region of the body without directly coupling to the implant structure.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which:

FIGS. 1A, 1B, and 1C are illustrations of a configuration of a smart medical device that includes a partially threaded cannulated screw (FIG. 1B) having a pair of electrodes, and an electronics cartridge (FIG. 1C) configured for insertion into the cannulated screw such that a pair of electrical contacts carried by the cartridge align with the pair of electrodes.

FIGS. 7A and 7B are schematic illustrations of a smart medical device that includes a cannulated screw having a pair of electrodes, and an electronics cartridge (shown in the cross-section of FIG. 7B) configured for insertion into the cannulated screw such that a pair of electrical contacts carried by the cartridge align with the electrodes.

FIGS. 8A and 8B are schematic illustrations of a smart medical device that includes a cannulated screw having an array of electrodes, and an electronics cartridge (shown in cross-section of FIG. 8B) configured for insertion into the cannulated screw such that a number of electrical contacts carried by the cartridge align with the electrodes.

FIGS. 12A, 12B, and 12C are illustrations of a smart medical device that includes a split cannulated screw having a distal portion and a proximal portion, each with an electrode, and an electronics cartridge configured for insertion into the cannulated screw such that electrical contacts carried by the cartridge align with the electrodes.

FIGS. 18A, 18B, 18C, 18D, 18E, 18F, 18G, 18H, 18I, and 18J are illustrations of tools and techniques for implanting a smart medical device.

FIGS. 24A, 24B, 25C, 24D, and 24E are illustrations of smart medical devices implanted relative to various types of bone fractures.

DETAILED DESCRIPTION

Figure 1D:
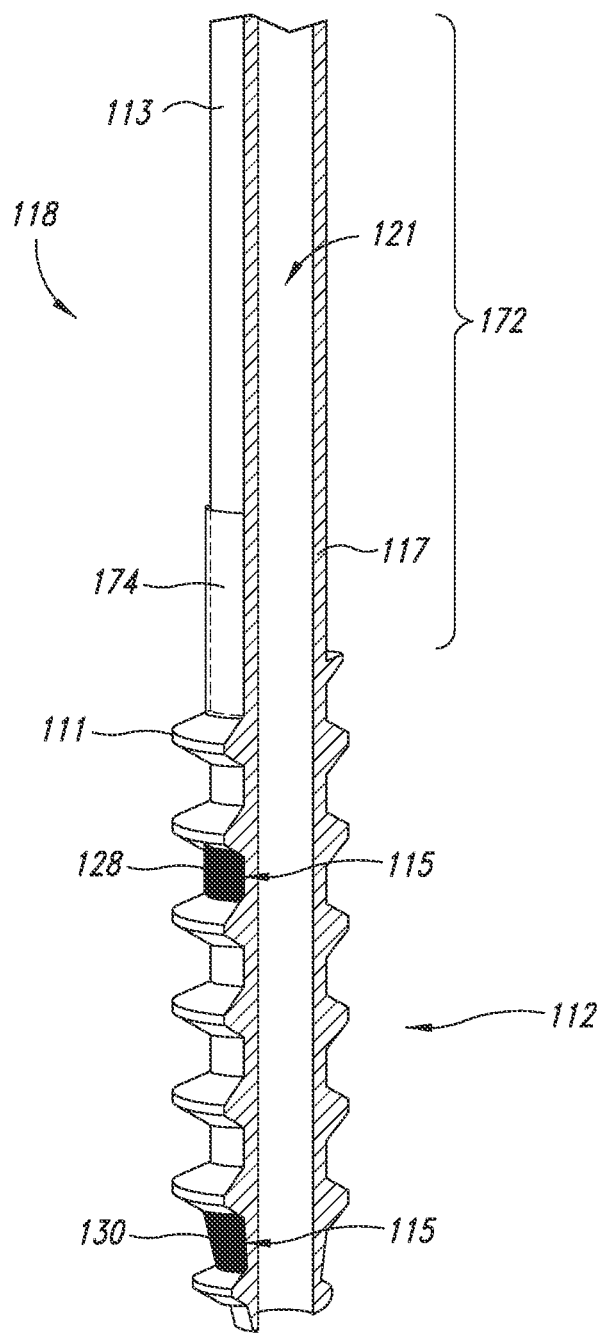
FIG. 1D is an illustration of a partially threaded cannulated screw wherein the non-threaded portion is coated with a material.

The smart medical devices disclosed herein includes electronics, e.g., application specific integrated circuit (ASIC) chips containing memory, microprocessors, and a radio telemetry component, a power supply (battery or super capacitor), radio and antenna environmental tuning (MICS or Bluetooth), sensors that validate bone healing measurement in vivo, and sensors that detect movement relative to a first placement location of the sensor. The smart medical device finds applications, for example, in orthopedic trauma and spine products, such as hip fracture screws, long bone fractures (in concert with plates), and spinal pedicle screws.

Two configurations of the smart medical device are contemplated. One is referred to herein as a cartridge configuration and the other as a preloaded configuration.

Cartridge Configuration

With reference to FIGS. 1A-1C, a cartridge configuration of a smart medical device 100 includes a structure 102 or outer body characterized by a tubular body having a lumen 104 extending at least partially therethrough. The structure 102 is configured to be at least partially implanted in a body. The medical device 100 also includes an electronics cartridge 106 or inner body having electronics, e.g., ASIC chips, power supply, antenna, etc. In some embodiments the electronics cartridge 106 may include a shell that houses the electronics. In other embodiments the electronics may be secured together or supported by a core element extending along the axis of the cartridge. The electronics cartridge 106 is configured to be inserted and seated into the lumen 104 of the structure 102 after implant of the structure.

In some embodiments the entirety of the structure 102 is formed of a single biocompatible, implantable grade material. Example implantable grade materials include: titanium, stainless steel cobalt chrome moly alloy, Nitinol, ceramic, alumina zirconia carbon hydroxyapatite, or a composite, e.g., carbon fiber reinforced PEEK.

In some embodiments, the structure 102 may be segmented into different portions being of a combination of different materials. For example, the structure 102 may have a distal body, section, or portion being of a metallic material; a center body, section, or portion being of a material different than the distal portion; and a proximal body, section, or portion being of a metallic material similar to the distal portion. In one example configuration, the metallic material of the distal portion and proximal portion may be an implantable grade material having a Young's Modulus between 100-200 gigapascals (GPa), tensile strength for either similar or dissimilar material interaction, while the material of the center portion may be of the same material as the distal portion or the proximal portion with a same or different Young's Modulus, or a different implantable grade material, e.g., a polymeric material. By having a segmented structure 102, different portions of the structure may have different properties for strength and performance for particular applications. For example, the material for different portions, whether they be dissimilar materials or similar materials, may be such that the strength of materials enable the structure 102 to penetrate and seat into a fractured bone to pull together the fracture for healing. A structure 102 configured in this way may support sensing operations of the medical device 100. For example, electrochemical impedance spectroscopy (EIS) measurements across a bone fracture site may be supported.

In configurations where the electronics cartridge 106 includes a shell or a core element, the shell or core element may be formed of an electrically insulated, non-conductive implantable grade material. In some embodiments, the electronics cartridge 106 may be configured to enhance a healing response at an implant site. To this end, the electronics cartridge 106 includes a mechanism that delivers a catalyst material that produces a gaseous oxygen reaction and heighten oxygen zone at the implant site by a chemical reaction. In some configurations, the mechanism is a reservoir that releases the catalyst material at one or more times after implant under the control of a time release controller. In other configurations, the mechanism is a coating of catalyst material that is added to the cartridge during the electronic processing of the cartridge. In either configuration, the material released by the cartridge mechanism creates an energy reaction to release a oxygen enriched environment to the localized zone about the implant for healing improvement.

In the embodiment of FIGS. 1A-1C, the structure 102 is a cannulated screw configured to be implanted into boney tissue. In one configuration, the lumen 104 of the cannulated screw 102 is configured to receive an implant tool during implant of the screw 102 into boney tissue. In another configuration, the lumen 104 may be configured to receive a support element, e.g., a "blank" cartridge, that temporarily fills the lumen to provide support to the cannulated screw 102 and reduce the possibility of breakage of the screw 102 as it is implanted into bone.

With continued reference to FIGS. 1A-1C, the cannulated screw 102 comprises a shaft 118 having an outer diameter in the range of 4 millimeters or greater and a head 119. The length of the shaft 118 varies depending on the application of the medical device 100. For example, for applications related to femoral head hip fracture, the length of the shaft 118 may be about 115 millimeters. The cannulated screw 102 includes a shaft 118 having a contiguous thread 111 around a portion thereof that defines a threaded portion 112 of the screw configured to secure the screw into bone. The lumen 104 comprises a shaft portion having an inner diameter sized to receive the electronics cartridge 106, and a volume sized to accommodate the electronics cartridge. The electronics cartridge 106 includes a proximal end 140, a distal end 142, a head 122 at the proximal end, and a shaft 126 extending from the head toward the distal end.

Each of the electronics cartridge 106 and the lumen 104 have a respective form factor that enables placement of the electronics cartridge 106 into the lumen 104. With reference to FIG. 1B, in one embodiment, the form factor of the lumen 104 of the cannulated screw 102 includes a head portion 120 and a shaft portion 124, wherein the inner diameter of the head portion is greater than the inner diameter of the shaft. The head portion 120 of the lumen 104 may correspond to a sunken pocket in a head 119, e.g., a polygon head, of the cannulated screw 102. The sunken pocket may be configured to receive a corresponding hex head of an implant tool and to transfer an application of torque to the implant tool to the screw during implant of the device into bone. With reference to FIG. 1C, the form factor of the electronics cartridge 106 includes a head 122 and a shaft 126, wherein the outer diameter of the head 122 is greater than the outer diameter of the shaft 126.

In one embodiment, the electronics cartridge 106 is configured to be secured within the lumen 104. In one embodiment, the electronics cartridge 106 is configured to be removed from the lumen without damaging the structural integrity of either the electronics cartridge or the structure.

Figure 2A:
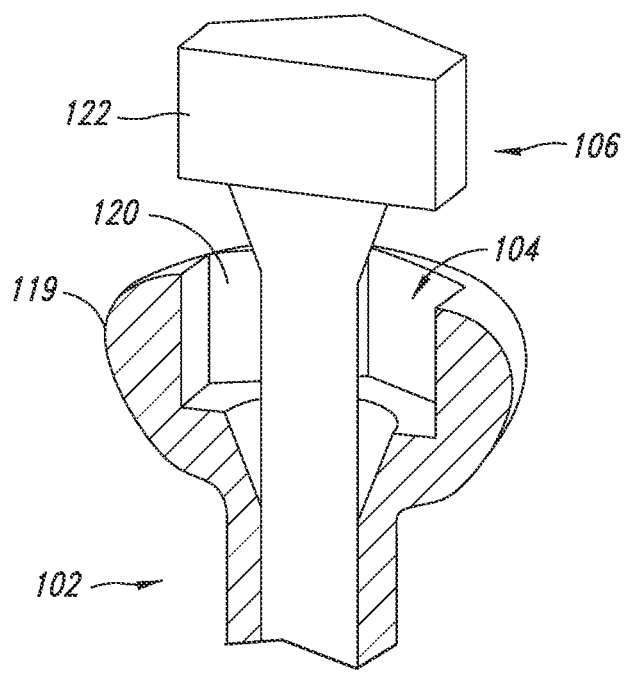
FIGS. 2A, 2B, 3A, 3B, 4, 5A, and 5B are illustrations of a various fixation mechanisms for securing an electronics cartridge in a cannulated screw.
Figure 2B:
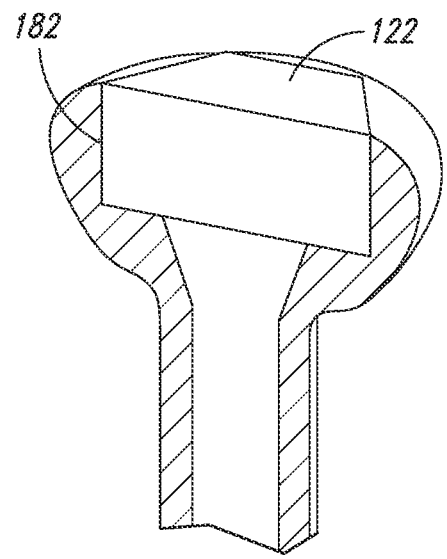

To these ends, various types of fixation mechanisms are contemplated. For example, with reference to FIGS. 2A and 2B, the head 122 of the electronics cartridge 106 and the head portion 120 of the lumen 104 of the cannulated screw 102 may be sized relative to each other such that a friction fit 182 results when the cartridge is fully inserted into the lumen 104 of the screw. In this configuration, the head 122 of the electronics cartridge 106 may be forced, e.g., hammered, into the head portion 120 of the lumen 104 of the cannulated screw 102 to establish the friction fit. In a variation of this configuration, a friction fit may be obtained based on the geometries of head portion 120 of the lumen 104 of the cannulated screw 102 and the head 122 of the electronics cartridge 106. For example, the head portion 120 of the lumen 104 may be oval shaped and a friction fit between it and the head 119 of the cannulated screw may be obtained by rotating the head 122 of the cartridge, for example, by one-quarter turn.

Figure 3A:
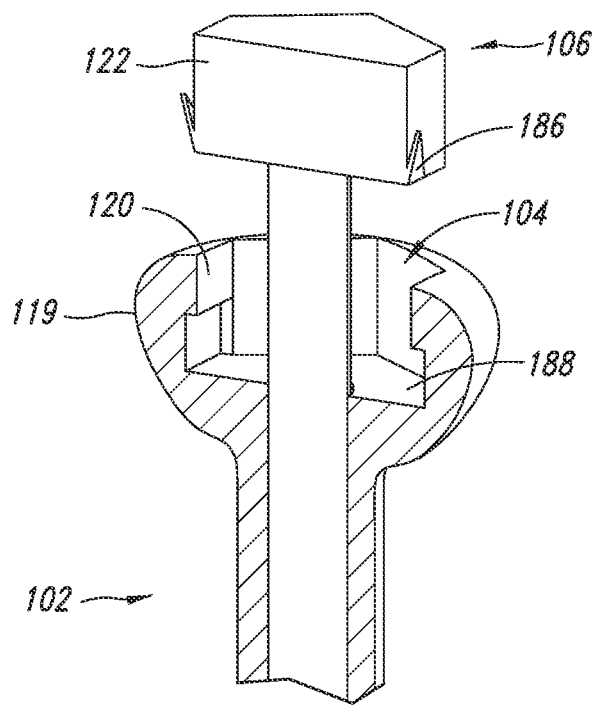
Figure 3B:
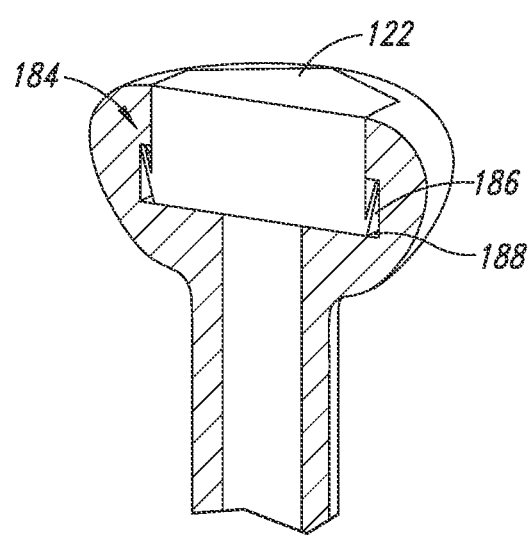

With reference to FIGS. 3A and 3B, in another embodiment, the head 122 of the electronics cartridge 106 and the head portion 120 of the lumen 104 of the cannulated screw 102 include complementary mechanical features such that a mechanical coupling 184 results when the cartridge is fully inserted into the lumen 104 of the screw. In one configuration, the mechanical feature of the electronics cartridge 106 is a tooth projection 186 and the mechanical feature of the cannulated screw 102 is an enlarged ring region 188 of the head portion 120 of the lumen 104 of the screw. In this configuration, the head 122 of the electronics cartridge 106 may be pushed into the head portion 120 of the lumen 104 of the cannulated screw 102 until tooth projection 186 clicks into place in the ring region 188 to thereby establish the mechanical coupling 184 to retain the electronics cartridge 106 is place in the cannulated screw by preventing movement of the cartridge outward from the cannulated screw. In a variation of this configuration, a snap fit feature, e.g., round or hexagonal ring, may extend around the entirety of the head 122 of the electronics cartridge 106 and snap fit into the ring region 188.

Figure 4:
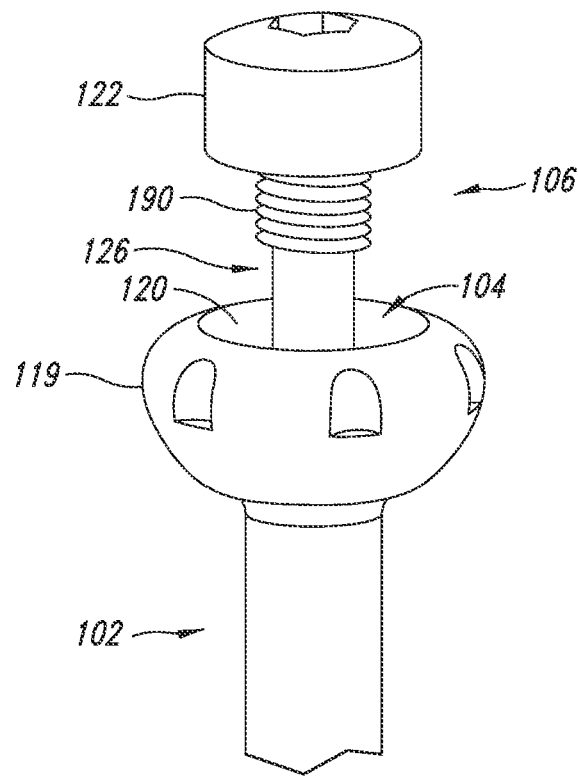

With reference to FIG. 4, in another embodiment, a section of the shaft 126 of the electronics cartridge 106 beneath the head 122 includes a thread portion 190 configured to engage a complementary threaded portion (not shown) in the lumen 104 of the cannulated screw 102. In this configuration, the electronics cartridge 106 has a circular cross-section along its length. The lumen 104 of the cannulated screw 102 also has a circular cross-section; thus allowing for rotation of the electronics cartridge 106 within the lumen 104 and threaded engagement of the components 102, 106. In this configuration, the electronics cartridge 106 may be subsequently removed from the cannulated screw 102 if needed by unscrewing it. In a variation of this configuration, the complementary threads may be located in the outer wall of the head 122 of the electronics cartridge and the inner wall of the head 119 of the cannulated screw 102. In this configuration, the head 119 of the cannulated screw includes features in its outer surface that couple with an implant tool to enable rotation of the screw during implant of the screw.

Figure 5A:
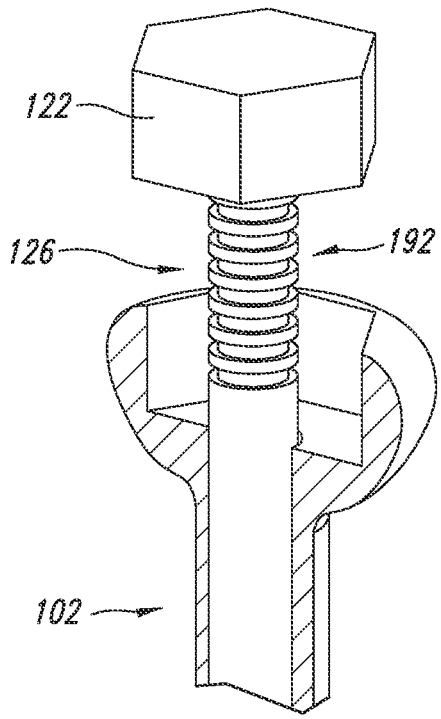
Figure 5B:
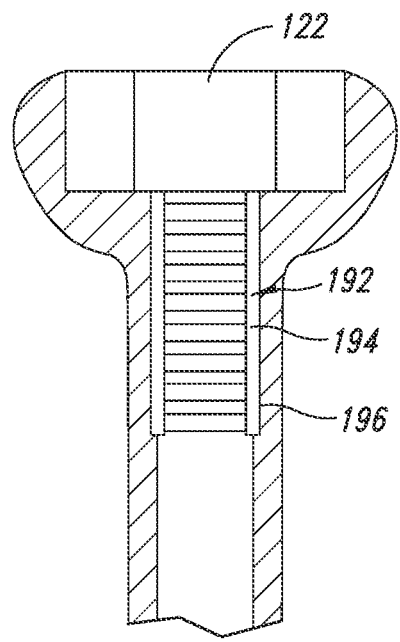

With reference to FIGS. 5A and 5B, in another embodiment, a section of the shaft 126 of the electronics cartridge 106 beneath the head 122 includes an interlock feature 192 comprising a number of grooves around the circumference of the shaft. In this configuration, an adhesive is applied to the interlock feature 192 prior to insertion of the electronics cartridge 106 into the lumen 104 of the cannulated screw 102. The adhesive 194 may be, for example, a biocompatible epoxy, such as polymethyl methacrylate (PMMA), or a silicone. Upon full insertion of the electronics cartridge 106 into the lumen 104 of the cannulated screw 102, an adhesive interface 194 forms between the interlock feature 192 and the inner wall 196 of the cannulated screw 102.

Other contemplated fixation mechanisms include a peel away surface at the underside of the head 122 of the electronics cartridge 106, which when peeled away exposes a tacky surface. Upon full insertion of the electronics cartridge 106 into the lumen 104 of cannulated screw, the tacky surface abuts the bottom surface of the head portion 120 of the lumen to thereby secure the electronics cartridge 106 in place.

With reference to FIGS. 1B and 1D, in some embodiments, the cannulated screw 102 includes an exterior surface 113 and one or more electrodes 128, 130 at the exterior surface. The electrodes 128, 130 may be arcuate pad electrodes having a radius of curvature similar to the radius of curvature of the shaft 118, and may extend along a groove between adjacent windings of the thread 111 that defines the threaded portion 112. For example, each electrodes 128, 130 may extend between 30 degrees and 180 degrees around the shaft 118. The electrodes 128, 130 are made of an electrically conductive implantable grade material having low resistivity. Example materials include: platinum, platinum iridium, gold, gold platted copper, silver or other low resistivity materials used in electron connection paths. The electrodes 128 130 are electrically isolated from the shaft 118 of the cannulated screw 102. To this end, an electrically insulative material may be between the surfaces of the electrodes 128, 130 that would otherwise contact the exterior surface 113 of the shaft 118. A hermitic feedthrough 115 extends through the sidewall 117 of the cannulated screw 102 and provides an electrical coupling between the electrodes 128, 130 and the interior 121 of the cannulated screw. The feedthrough 115 may be a conventional ceramic feedthrough with gold-brazed conductor, a glass feedthrough, or cofired ceramic feedthrough.

With reference to FIG. 1D, in embodiments having a partially threaded cannulated screw 102, such as the embodiment of FIGS. 1A-1C, a layer 174 of electrically insulative material may be applied to the non-threaded portion 172 of the screw to form a coated region. The material may be, for example, titanium dioxide or aluminum oxide applied to the non-threaded portion 172 using anodization. Titanium dioxide resistance is similar to cobalt chrome oxide, which is an excellent electrical insulator. The material may be a diamond material applied to the non-threaded portion 172 using chemical vapor deposition to obtain a highly insulating coating. The material may be a ceramic material applied to the non-threaded portion 172 using vapor deposition of chemical plating to initiate the coating bond, and conductive or non-conductive metallic liquid metal reflow caused by Eutectic attachment methods.

To minimize coating shear, the minor diameter of the threaded portion 112 of the cannulated screw 102 is increased by an amount substantially equal to the thickness of the layer 174 of material. Accordingly, the outer diameter of the coated region of the cannulated screw 102 is generally equal to the minor diameter of the threaded portion 112 of the cannulated screw 102.

The electrodes 128, 130, in combination with other electronics of the medical device 100, may define a sensor or sensor system configured to monitor electrical properties of tissue. In some embodiments, the sensor system is an impedance sensor that functions as an EIS sensor to detect the location of a bone fracture and monitor the healing status of such fracture. Details of the EIS sensor are disclosed further below. The electrodes 128, 130, in combination with other electronics of the medical device 100, may define a communications interface. Details of the communication interface are disclosed further below.

With reference to FIG. 1C, in some embodiments, the electronics cartridge 106 comprises an exterior surface and one or more electrical contacts 132, 134 at the exterior surface configured to electrically couple to the one or more electrodes 128, 130 when the electronics cartridge is inserted into the lumen. A insulating seal 133 between the electrical contacts 132, 134 prevents detrimental electrical contact between the two electrodes 128, 130 or the two electrical contacts 132, 134 if the space between them fills with conductive fluid. The insulating seal 133 may be an O-ring or a compliant over-molded silicone wiper. Each of the cannulated screw 102 and the electronics cartridge 106 comprise a respective feature for aligning the one or more electrodes 128, 130 with the one or more electrical contacts 132, 134 when the electronics cartridge is inserted into the lumen 104. The features may be complementary mechanical features, such as a groove in a surface of either of the cannulated screw 102 and the electronics cartridge 106 and a protrusion extending from the other of the screw and electronics cartridge.

With reference to FIGS. 1B and 6A-6C, the cannulated screw 102 includes a proximal end 136, a distal end 138, and one or more electrodes along the shaft 118 between the proximal end and the distal end. Different numbers and arrangements of electrodes are contemplated.

Figure 6A:
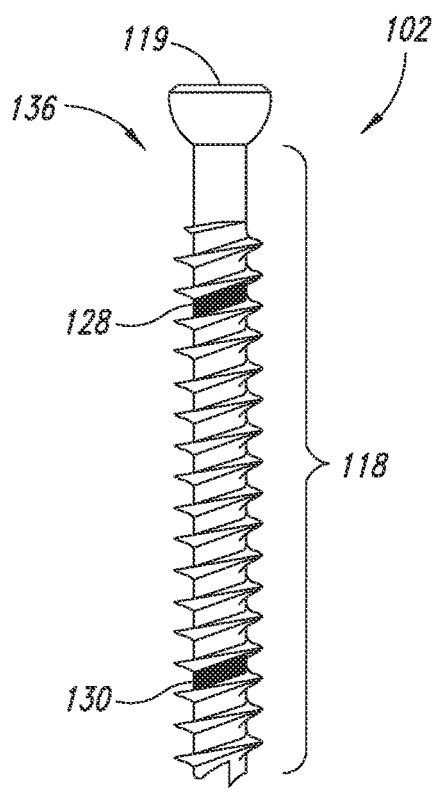
FIGS. 6A, 6B, and 6C are illustrations of different configurations of a fully threaded cannulated screw that may be used in the medical device of FIGS. 1A-1C, including a configuration having a single pair of electrodes (FIG. 6A), a configuration having two pairs of electrodes (FIG. 6B), and a configuration having an array of electrodes (FIG. 6C).

For example, with reference to FIGS. 1B and 6A, in some configurations, the cannulated screw 102 may have a single pair of spaced apart electrodes on the shaft 118, including a distal electrode 130 near the distal end 138 and a proximal electrode 128 near the proximal end 136. In the configuration of FIG. 1B, the electrodes 128, 130 are located on the shaft 118 on either side of the threaded portion 112 of the cannulated screw 102 and may be spaced apart by a distance of between 20-30 mm or more. In the configuration of FIG. 6A, each of the electrodes 128, 130 is located on the shaft 118 between adjacent windings of the thread 111 of the shaft and may be spaced apart by a distance of between 20-30 mm or more. The electrodes 128, 130 may be arcuate pad electrodes having a radius of curvature similar to the radius of curvature of the shaft 118, and may extend along a groove between adjacent windings of the thread 111. For example, each electrodes 128, 130 may extend between 30 degrees and 180 degrees around the shaft 118.

Figure 6B:
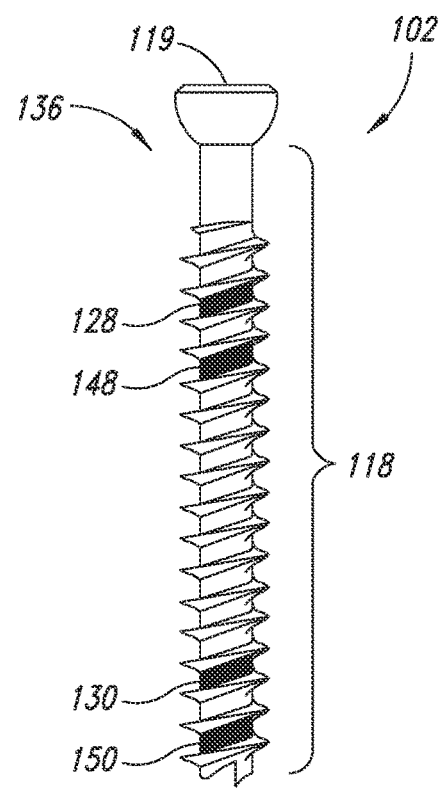

With reference to FIG. 6B, in some embodiments, the cannulated screw 102 may have two pairs of electrodes along the shaft 118. A pair of distal electrodes 130, 150 is located near the distal end 138 and a pair of proximal electrodes 128, 148 is located near the proximal end 136. In one configuration, the electrodes 128, 130, 148, 150 may be located between adjacent windings of the thread 111 of the shaft 118. The electrodes 128, 130, 148, 150 within a pair may be spaced apart by a distance between 2-10 mm, and the pairs of electrodes may be spaced apart by a distance of between 20-30 mm or more. The electrodes 128, 130, 148, 150 may be arcuate pad electrodes having a radius of curvature similar to the radius of curvature of the shaft 118, and may extend along a groove between adjacent windings of the thread 111. For example, each electrodes 128, 130, 148, 150 may extend 30 degrees and 180 degrees around the shaft 118.

Figure 6C:
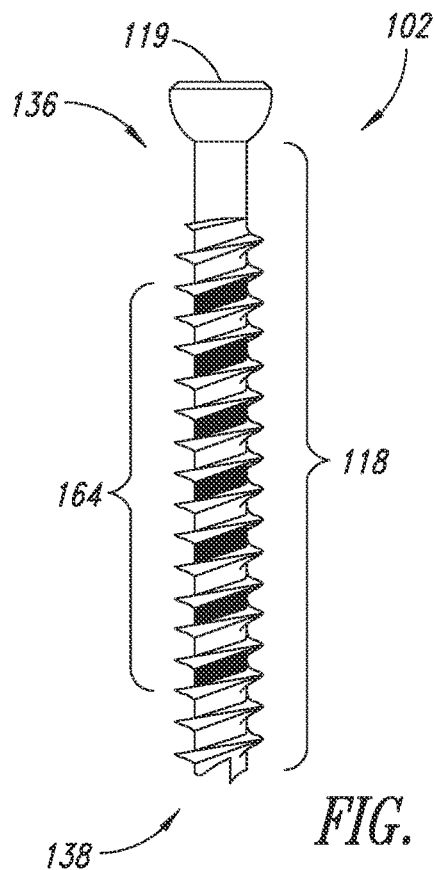

With reference to FIG. 6C, in some embodiments, the cannulated screw 102 may have an array of electrodes 164 along the shaft 118 between the distal end 138 and the proximal end 136 of the cannulated screw 102. In one configuration, each electrode in the array of electrodes 164 may be located between adjacent windings of the thread 111 on the shaft 118 and may be spaced apart by a distance of between 2-10 mm. The electrodes of the array of electrodes 164 may be arcuate pad electrodes having a radius of curvature similar to the radius of curvature of the shaft 118, and may extend along a groove between adjacent windings of the thread 111. For example, each electrode in the array of electrodes 164 may extend between 30 degrees and 180 degrees around the shaft 118.

With reference to the schematic illustrations of FIGS. 7A and 7B, in a configuration of a medical device 100 having a single pair of electrodes 128, 130, the electrodes are electrically isolated from each other. For example, the shaft 118 extending between the proximal end 136 and the distal end 138 of the cannulated screw 102 may be formed of a material that does not conduct electricity or it may be coated with an electrically insulating material. In either case, the one or more electrodes 128, 130 are separated by an insulation region 152. Additional insulation regions 155, 156 at the sides of the electrodes 128, 130 electrically isolate the electrodes 128, 130 from the surface of the cannulated screw 102, which may be electrically conductive.

With reference to the schematic illustrations of FIGS. 8A and 8B, in a configuration of a medical device 100 having an array of electrodes 164, the electrodes are electrically isolated from each other. For example, the shaft 118 extending between the proximal end 136 and the distal end 138 of the cannulated screw 102 may be formed of a material that does not conduct electricity or it may be coated with an electrically insulating material. In either case, the one or more electrodes 128, 130 are separated by insulation regions 158.

With reference to FIGS. 1C, 7B, and 8B, as previously described, the electronics cartridge 106 includes a proximal end 140, a distal end 142, a head 122 at the proximal end, and a shaft 126 extending from the head toward the distal end. The electronics cartridge 106 is configured to electrically couple the electrodes 128, 130, 148, 150, 164 of the cannulated screw 102 with electronics housed within the cartridge.

To this end, and with reference to FIGS. 1C and 7B, in some embodiments the electronics cartridge 106 includes an exterior surface and a pair of electrical contacts 132, 134 at the exterior surface configured to electrically couple to the pair of electrodes 128, 130 of the cannulated screw when the electronics cartridge is inserted into the lumen of the cannulated screw. The pair of electrical contacts 132, 134 extend through a wall of the shell of the electronics cartridge 106 to electrically couple to electronics within the cartridge. As previously mentioned, the shell is formed of a non-conductive material. Accordingly, the pair of electrical contacts 132, 134 are electrically isolated from each other.

With reference to FIG. 8B, in some embodiments the electronics cartridge 106 includes an exterior surface and an array of electrical contacts 166 at the exterior surface configured to electrically couple to the array of electrodes 164 when the electronics cartridge is inserted into the lumen of the cannulated screw. Each electrical contact 166 included in the array of electrical contacts extends through a wall of the shell of the electronics cartridge 106 to electrically couple to electronics within the cartridge. As previously mentioned, the shell is formed of a non-conductive material. Accordingly, the electrical contacts 166 are electrically isolated from each other.

With reference to FIGS. 1C, 7B, and 8B, electronics included in the electronics cartridge 106 may be associated with one or more electronics assemblies located in either one or both of the head 122 and the shaft 126. The electronics of the electronics cartridge 106 comprise an implantable reporting processor (IRP), details of which are provided further below with reference to FIGS. 22A and 22B. Regarding the structure of the IRP, in some embodiments, the IRP includes one or more antenna 144, 145, one or more rechargeable power supplies 154, and one or more electronics assemblies comprising:

Communications circuitry that enables communication between the device and another device (either implanted in the body or external the body);

One or more sensors that can be utilized to do one or more of: 1) detect, measure and/or monitor one or more different aspects of a body tissue (anatomy, physiology, metabolism, and/or function), 2) detect, measure and/or monitor one or more aspects of body or body segment/joint condition or function (fracture healing, motion including measurement of the positions, angles, velocities, and accelerations of body segments and joints), and/or 3) detect, measure and/or monitor one or more aspects of the orthopedic device or implant; and Various other components, e.g., memory, switches, processors, etc., that enable operation of the medical device 100.

The electronics are positioned within the electronics cartridge 106 to minimize loading on the electronic components, including in particular the more sensitive electronics, such as the processor, CPU, communications circuitry, and ASIC or power supply, e.g., capacitor, battery, or storage cell. To this end, electronics are generally placed away from high stress zones of the medical device 100 and instead in minimally loading portions of the device. For example, in the case of a medical device 100 for use in treating a bone fracture, high stress zones include: a) the interface change from the head to the shaft body, due to the load of torque during implant and compression upon implant, b) the distal transition from the screw threads to the shaft body due to diametric change, and the load of torque during implant and compression upon implant, and c) the center of the shaft body itself because of torque, moment and axial stress concentrations in this zone. Accordingly, sensitive electronics, such as the processor, CPU, communicator circuitry and ASIC, are located at the proximal end of the electronics cartridge 106, while less sensitive electronics, like the power supply 154, are located at the mid-region of the cartridge. In some embodiments, electronics may be placed in high stress areas of the medical device 100, but may be configured to withstand the stress, by for example, being flexible to allow for some deformation under loading conditions of the device.

In applications involving multiple medical devices, the device at the implant location that will be the least loaded, i.e., the location that is least subject to stress on the implanted medical implant, may be selected to be a smart medical device 100. For example, in the case of a medical device 100 for use in treating a femoral neck fracture with an inverted triangle approach, such as shown in FIG. 24B, the least loaded location corresponds to the point of the inverted triangle. Accordingly, the medical device 100 may be placed at the point of the inverted triangle, where it will serve primarily a characterization function to characterize the fraction and its healing. Medical devices that serve entirely or primarily a stability function, which optionally do not contain a sensor, may be placed at the other locations of the inverted triangle, in order to securely hold the boney tissue together during healing.

Thus, in one aspect the present disclosure provides a set of medical devices, i.e., at least two medical devices, optionally three, or four, or five, etc. medical devices, that together are used to treat a fracture in boney tissue. In one embodiment, the medical devices in the set are all screws. Particularly in the case where the medical device of the present disclosure is intended to provide little or no stability function, the medical device of the present disclosure may be utilized in association with other medical devices, e.g., standard orthopedic screws which do not contain a sensor, and which primarily provide a stability function to the healing tissue. Thus, in one aspect, the present disclosure provides a set of medical devices, where at least one member of the set is a smart medical device of the present disclosure which provides characterization function (and optionally some stability function), and at least one member of the set is utilized to provide primarily or exclusively stability function (and optionally no characterization function). For example, in one aspect, the present disclosure provides a set of three medical devices, where one member of the set is a smart medical device of the present disclosure which provides characterization function (and optionally some stability function), and two members of the set are utilized to provide primarily or exclusively stability function, where optionally each of the medical devices is a screw. Thus, in use, the smart medical device of the present disclosure may optionally be placed in boney tissue at a location where stability function is not too necessary, i.e., at a non-loaded or slightly-loaded location. The medical devices of the set that are utilized to provide primarily or exclusively stability function, may be placed at relatively highly loaded locations in the boney tissue. Thus, in one embodiment, the present disclosure provides a method of treating a femoral neck fracture with an inverted triangle approach, comprising placing a medical device of the present disclosure, e.g., the medical device 100, at the point of the inverted triangle, and placing medical devices without sensors at the other points of the triangle.

In one aspect, the present disclosure provides a set of medical devices, the set comprising at least one first medical device of the present disclosure, the set further comprising at least one second medical device configured for insertion into boney tissue, where the second medical device does not contain a sensor. Optionally, each of the first medical device and the second medical device is a screw. Optionally, the set comprises a single, i.e., only one, first medical device and a plurality, i.e., more than 1, i.e., 2 or more, of second medical devices, where optionally each member of the set is a screw.

Figure 9A:
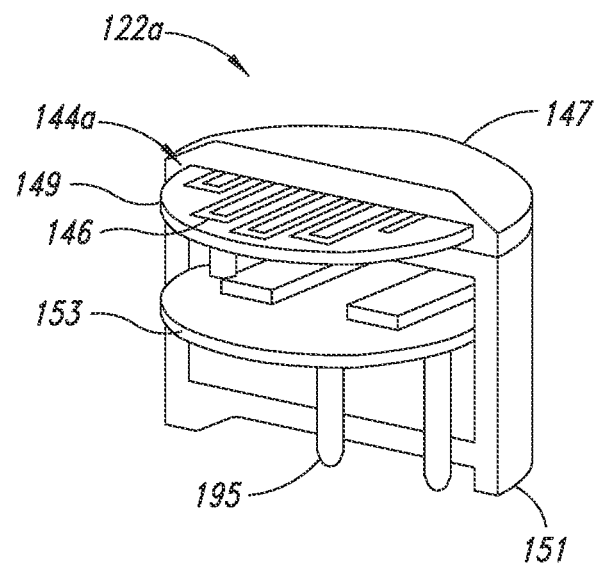
FIGS. 9A and 9B are illustrations of different configurations of the head end of the electronics cartridge of FIG. 1C.
Figure 9B:
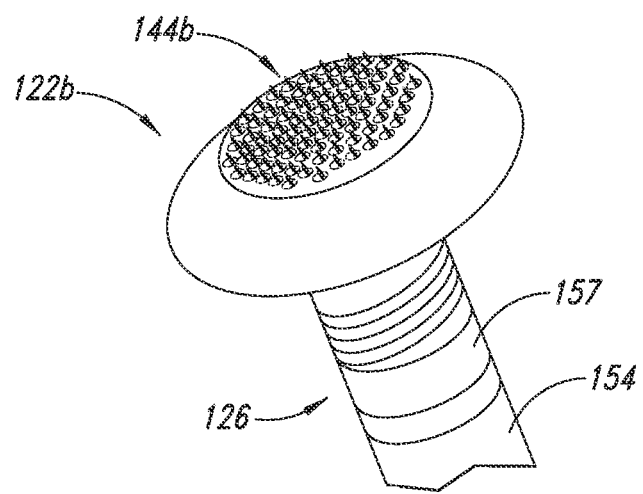

Regarding the one or more antenna 144, 145 of the electronics cartridge 106, in some embodiments the antenna 144 is entirely internal to the cartridge and may be located in the head 122 of the cartridge, or in the shaft 126 of the cartridge, or partially in the head and partially in the shaft. For example, with reference to FIG. 9A, the head 122*a* of the electronics cartridge 106 may include an antenna 144*a* encapsulated in a material 147, such as PEEK. The antenna 144*a* may be a conductive wire 146 or trace extending along an antenna board 149 parallel with a base 151 of the head 122. With reference to FIG. 9B, in another embodiment of the electronics cartridge 106, an antenna 144*b* that is configured to function as both a communications antenna and a recharge element may be located at the top of the head 122*b*. The antenna 144*b* may be configured as a multiplanar array of protruding pins.

With reference to FIG. 1C, in another embodiment of the electronics cartridge 106, the antenna 145 is associated with the shaft 126. The antenna 145 may comprise a conductive wire or trace wound around and extending along a portion of the shaft 126. For example, the antenna 145 may be a wire that extends in a helical pattern around the shaft 126. The antenna 145 is embedded in the shaft and thus electrically insulated from the outer surface of the shaft 126 to avoid contact with the interior of the cannulated screw 102 when the electronics cartridge 106 is inserted into the lumen 104 of the screw. The antenna 145 may be connected to electronics in the head 122 through an insulated trace or wire running along the shaft 126 between the antenna and the head.

In some embodiments the antenna may be entirely external to the cartridge. In some embodiments, the antenna may be partially internal to the cartridge and partially external to the cartridge.

Regarding the one or more power supplies 154 of the electronics cartridge 106, with reference to FIGS. 7B and 8B, the power supply 154 may be associated with the shaft 126 of the electronics cartridge 106, and may be located in the middle region, along the length of the shaft for structural stability purposes. The one or more power supplies 154 may be rechargeable and a recharge mechanism, e.g., coil, may be located in the head of the electronics cartridge 106. In other embodiments (not shown), the power source may be associated with the head 122 of the electronics cartridge 106 and a recharge mechanism, e.g., coil, may be co-located with the battery in the head of the electronics cartridge 106. As will be described further below, the one or more power supplies 154 may be one or more of a battery, e.g., a rechargeable battery, and a capacitor, e.g., a super capacitor. The electronics may include an energy harvesting device configured to harvest energy by one of electrostatic energy, wireless energy transfer, and IR radiation.

Regarding the communication circuitry of the electronics cartridge 106, in one embodiment the one or more communication components include a radio frequency (RF) transceiver coupled to an antenna 144, 145 and configured to receive and transmit RF signals (e.g., Bluetooth or MICS). With reference to FIG. 9A, the RF transceiver may be associated with an electronics assembly 153 in the form of a circuit board located in the head 122*a*. With reference to FIG. 9B, the RF transceiver may be associated with an electronics assembly 157 in the form of a circuit capsule located in the shaft 126. Details of RF telemetry communication are disclosed further below with reference to FIG. 22A.

In another embodiment, the one or more communication components include tissue conductive communication circuitry coupled to a pair of electrodes associated with the medical device 100 and configured and located to be placed in contact with tissue. The tissue conductive communication circuitry may include a transmitter and a receiver. The pair of electrodes may correspond to the electrodes 128, 130 of the medical device 100. Configured as such, the one or more communication components may be configured to at least one of enable capacitive coupling between the medical device 100 and another device; or to enable galvanic coupling between the medical device and another device. With reference to FIG. 9A, the tissue conductive communication circuitry may be associated with an electronics assembly 153 in the form of a circuit board located in the head 122*a*. With reference to FIG. 9B, the tissue conductive communication circuitry may be associated with an electronics assembly 157 in the form of a circuit capsule located in the shaft 126. Details of capacitive and galvanic coupling communications are disclosed further below with reference to FIG. 22A.

Regarding the sensors of the electronic cartridge 106, in some embodiments, the one or more sensors may include an EIS sensor comprising electrodes 128, 130, of the medical device in combination with an electrode switch and a sensing circuitry/module of the medical device 100. With reference to FIG. 9A, the electrode switch and sensing circuitry/module may be associated with an electronics assembly 153 in the form of a circuit board located in the head 122*a*. With reference to FIG. 9B, the electrode switch and sensing circuitry/module may be associated with an electronics assembly 157 in the form of a circuit capsule located in the shaft 126. Details of the EIS sensor are disclosed further below with reference to FIGS. 22A and 22B.

In some embodiments, the one or more sensors may include an inertial measurement unit (IMU) such as an accelerometer or gyroscope configured to output a signal corresponding to motion of the medical device 100, and by association, motion of the boney structure in which the device is implanted, and motion or activity of the patient in which the device is implanted. The accelerometer may be a one-dimensional accelerometer, a two-dimensional accelerometer, a three-dimensional accelerometer, or any available dimensional accelerometer. The electronics further comprise a processor coupled to the accelerometer to receive the signal and configured to process the signal to provide an indication of one or more of patient activity, integrity of the medical device (breakage), and movement of the medical device relative to implant location (back-out). For example, the position of the accelerometer may be determined post implant and a detection of a change in that position may be used to detect a movement of the medical device at the implant location. With reference to FIG. 9A, the accelerometer or gyroscope and the processor may be associated with an electronics assembly 153 in the form of a circuit board located in the head 122*a*. With reference to FIG. 9B, the accelerometer or gyroscope and the processor may be associated with an electronics assembly 157 in the form of a circuit capsule located in the shaft 126.

In some embodiments, the one or more sensors may include a strain sensor associated with the medical device 100. The electronics further comprise a processor coupled to the strain sensor to receive the signal and configured to process the signal to provide an indication of one or more of integrity of the medical device (breakage), and movement of the medical device relative to implant location (back-out or indication of fracture healing). With reference to FIG. 9A, the strain sensor and the processor may be associated with an electronics assembly 153 in the form of a circuit board located in the head 122*a*. With reference to FIG. 9B, the strain sensor and the processor may be associated with an electronics assembly 157 in the form of a circuit capsule located in the shaft 126.

In some embodiments, the one or more sensors may include an acoustic resonance sensor associated with the medical device 100 and configured to output a signal corresponding to the level of acoustic vibration/movement of the medical device. The electronics further comprise a processor coupled to the acoustic resonator to receive the signal and configured to process the signal to provide an indication of the degree of fixation of the medical device within the boney structure at the implant site, which in turn may provide an indication of the healing state of the bone. The acoustic resonance sensor may be a single device associated with the medical device 100 that vibrates or it may a pair of devices comprising an acoustic transmitter at one end of the medical device 100 and an acoustic receiver at the other end of the device. The acoustic transmitter outputs an acoustic signal through the medical device 100. The acoustic receiver senses the acoustic signal and outputs an electrical signal having an amplitude indicative of the strength of the acoustic signal it received. The processor may analyze the amplitude to determine the state of healing of the fracture, wherein progression of acoustic signals toward a lower amplitude (meaning less vibration of the medical device) overtime is indicative of bone healing. With reference to FIG. 9A, the acoustic resonance sensor and the processor may be associated with an electronics assembly 153 in the form of a circuit board located in the head 122*a*. With reference to FIG. 9B, the acoustic resonance sensor and the processor may be associated with an electronics assembly 157 in the form of a circuit capsule located in the shaft 126.

In some embodiments, the one or more sensors may include a stress sensor associated with the medical device 100 and configured to output a signal corresponding to the level of stress in the medical device. The electronics further comprise a processor coupled to the stress sensor to receive the signal and configured to process the signal to provide an indication of the degree of fixation of the medical device within the boney structure at the implant site, which in turn may provide an indication of the healing state of the bone. The stress sensor may be a single device associated with the medical device 100 that senses local stress, or it may be a device comprising a stress sensor in or on the medical device 100. The stress sensor senses the mechanical stress in a section of the medical device 100 and outputs an electrical signal having an amplitude indicative of the magnitude of the stress. The processor may analyze the amplitude to determine the state of healing of the fracture, wherein progression of stress magnitudes toward a lower amplitude (meaning stress of the medical device) overtime is indicative of bone healing. With reference to FIG. 9A, the stress sensor and the processor may be associated with an electronics assembly 153 in the form of a circuit board located in the head 122*a*. With reference to FIG. 9B, the stress sensor and the processor may be associated with an electronics assembly 157 in the form of a circuit capsule located in the shaft 126.

In some embodiments, the one or more sensors may include a temperature sensor configured to output a signal corresponding to a temperature of the medical device 100 at the implant location. With reference to FIG. 9A, the temperature sensor and the processor may be associated with an electronics assembly 153 in the form of a circuit board located in the head 122*a*. With reference to FIG. 9B, the temperature sensor and the processor may be associated with an electronics assembly 157 in the form of a circuit capsule located in the shaft 126. In some embodiments, the temperature sensor may be associated with the cannulated screw 102.

With reference to FIG. 9A, the electronics in the head 122*a* may also include other components, e.g., memory, power switches, fuses, etc., associated with an electronics assembly 153 in the form of a circuit board beneath the antenna board 149. The electronics in the head 122*a* may also include battery contacts 195 that extend to a power supply (not shown) located in the shaft 126 of the electronics cartridge 106. In other embodiments, some of the electronics may be mounted on a printed circuit board located in the shaft 126. With reference to FIG. 9B, the electronics in the shaft 126 may include a power supply 154 and other components, e.g., memory, power switches, fuses, etc., associated with an electronics assembly 157 in the form of a circuit capsule located in the shaft 126. Details of these components are disclosed further below with reference to FIG. 22A.

In some embodiments the electronics cartridge 106 includes a mechanism configured to deliver a catalyst material that produces a gaseous oxygen reaction at the implant site by a chemical reaction. The mechanism may be a reservoir that releases the catalyst material at one or more times after implant under the control of a time release controller of the processor. The mechanism may be a coating of catalyst material on the cartridge that passively elutes into the body. Reaction of the catalyst material with the body may be enhanced by delivery of electrical stimulation through electrodes of the medical device.

Figure 10A:
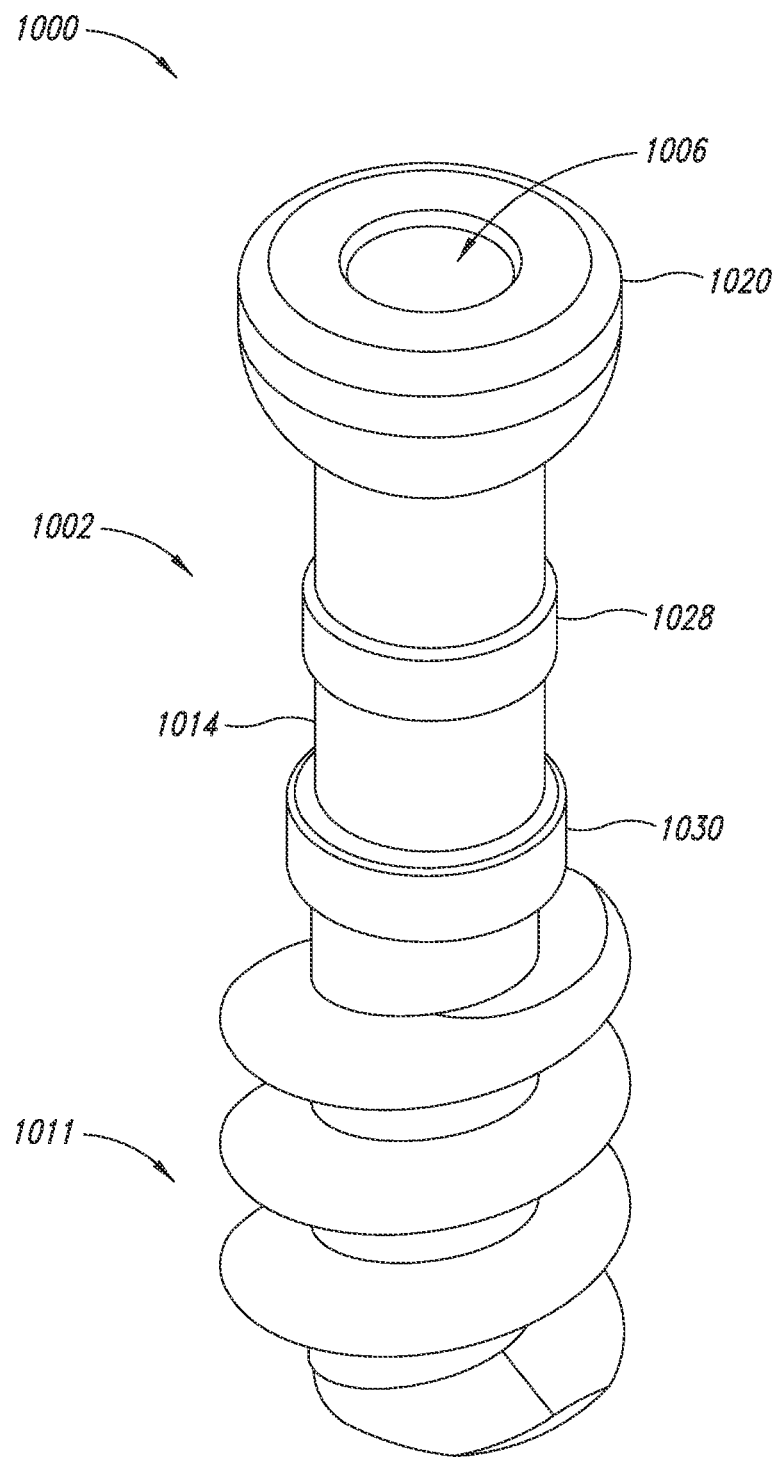
FIGS. 10A and 10B are illustrations of a smart medical device that includes a cannulated screw having a pair of electrodes masked onto the surface of the screw, and an electronics cartridge configured for insertion into the cannulated screw such that a pair of electrical contacts carried by the cartridge align with the electrodes.
Figure 10B:
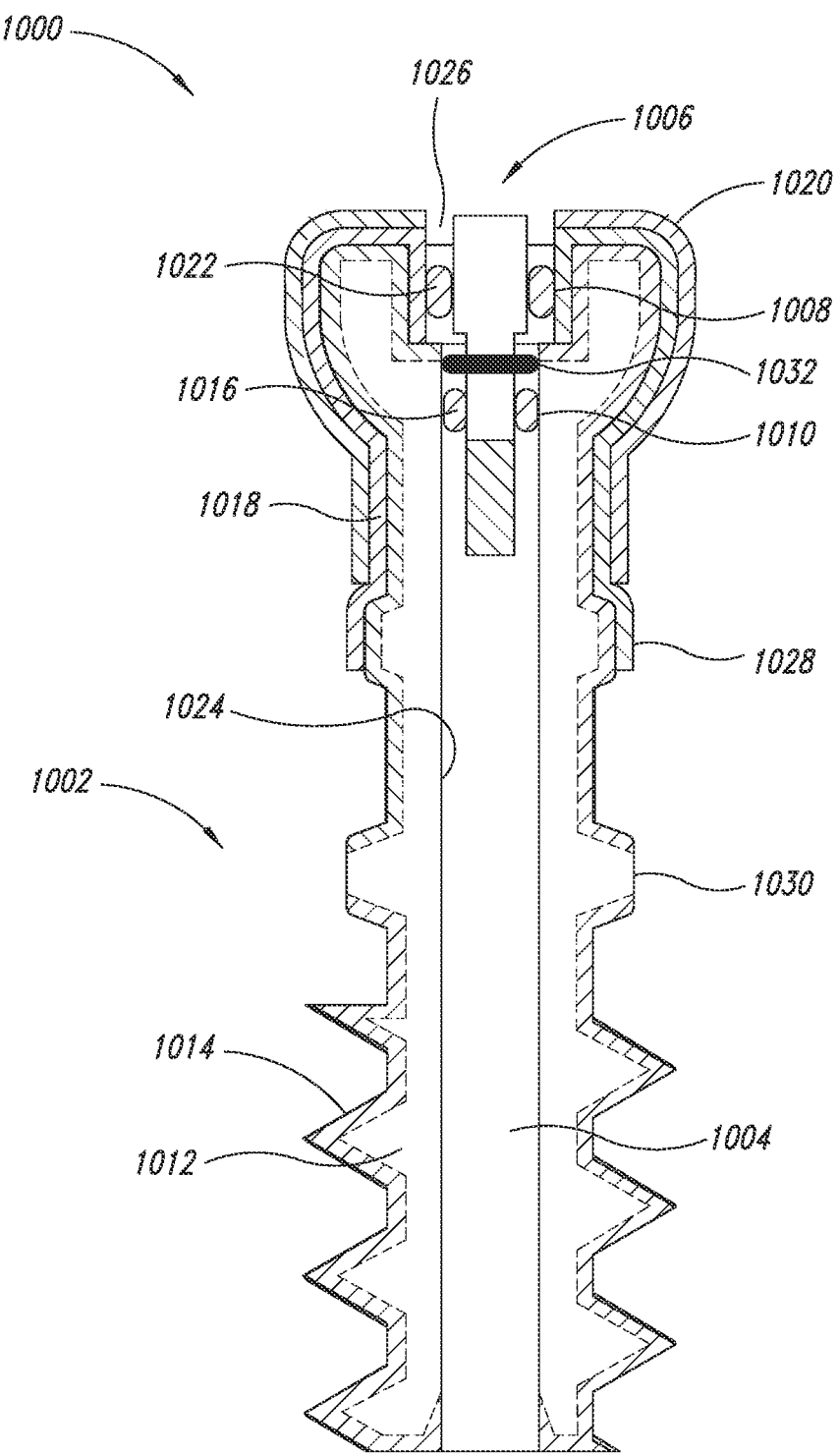

With reference to FIGS. 10A and 10B, in some embodiments a cartridge configuration of a smart medical device 1000 includes a cannulated structure 1002 having a lumen 1004 extending therethrough, and a plurality of electrodes 1028, 1030 at an outer surface of the structure. As with other embodiments of medical devices, the cannulated structure 1002 is configured to be at least partially implanted in a body. The medical device 1000 also includes an electronics cartridge 1006 including electronics. The electronics cartridge 1006 is configured to be inserted into the lumen 1004 of the cannulated structure 1002. Upon insertion, the electronics cartridge 1006 establishes one or more electrical couplings 1008, 1010 between the electronics of the cartridge and the plurality of electrodes 1028, 1030.

The cannulated structure 1002 includes an electrically conductive substrate 1012 having a threaded portion 1011.

The electronics cartridge 1006 includes a first electrical contact 1016 and a second electrical contact 1022. The first electrical contact 1016 is positioned to contact an inner surface 1024 of the electrically conductive substrate 1012 to thereby establish an electrical coupling 1010 between the electronics and the first electrode 1030. The second electrical contact 1022 is positioned to contact a portion of the second electrode 1028 to thereby establish an electrical coupling 1008 between the electronics and the second electrode 1028.

The exterior surface of the conductive substrate 1012 is at least partially treated or coated with an electrically insulative material 1014. For example, a titanium conductive substrate 1012 may be anodized to make the surface electrically insulated. A first electrode 1030 of the plurality of electrodes corresponds to an exposed portion of the electrically conductive substrate 1012 that is connected to the electronics cartridge 1006 through the first electrical contact 1016 of the cartridge. The first electrical contact 1016 may be for example, a leaf spring, press fit metal ring, contacting metal surface, etc. The surface of first electrode 1030 and the surface contacting the first electrical contact 1016 do not have surface treatment or coating. This allows an electrical connection to the electronics cartridge 1006 through the conductive substrate 1012.

A second electrode 1028 of the plurality of electrodes overlies a portion of the electrically insulative material 1014 at the proximal end of the cannulated structure 1002 and is connected to the electronics cartridge 1006 through the second electrical contact 1022 of the electronics cartridge 1006. The second electrical contact 1022 may be for example, a leaf spring, press fit metal ring, contacting metal surface, etc.

The second electrode 1028 is constructed by coating or treating the conductive substrate 1012 to form a conductive surface layer 1018 on top of the insulative material 1014. The coating forming the conductive surface layer 1018 is thin to maintain strength of the cannulated structure 1002 and to maintain an outer diameter similar to conventional cannulated structures. Electrical contact with the patient outside of the areas of the second electrode 1028 may be prevented by a thin insulating treatment or coating 1020 and/or by slightly reducing the diameter of the cannulated structure 1002 in the area of the second electrode to reduce contact with bone. The insulating treatment or coating 1020 may be added by several processes, for example: vapor deposition, electroplating, silk screening, or powder coating. In this embodiment, the conductive surface layer 1018 wraps around the insulated head of the conductive substrate 1012 and coats the inside of the drive socket 1026.

The two electrical contacts 1016, 1022 of the electronics cartridge 1006 are separated from each other by an insulating seal 1032. The insulating seal 1032 prevents detrimental electrical contact between the two electrodes 1028, 1030 or the two electrical contacts 1016, 1022 if the space between them fills with conductive fluid. The insulating seal 1032 may be an O-ring or a compliant over-molded silicone wiper. The second electrode 1028 may be protected from abrasion during insertion by a sacrificial lubricious coating. The second electrode 1028 may also be protected mechanically by placing the conductive and insulating coatings in a recessed channel cut into the screw wall. With this construction technique, any placement, shape, and size of electrode is possible.

The embodiment of FIGS. 10A and 10B employs layers or coatings of insulative, non-conductive material 1014 and conductive material 1018 to create multiple electrodes 1028, 1030 without altering the conductive substrate 1012 of the cannulated structure 1002. Using masking, coatings can be applied to various dimensions along the length of the cannulated structure 1002 to create different electrodes. An area of the conductive substrate 1012 acts as one electrode.

Figure 11A:
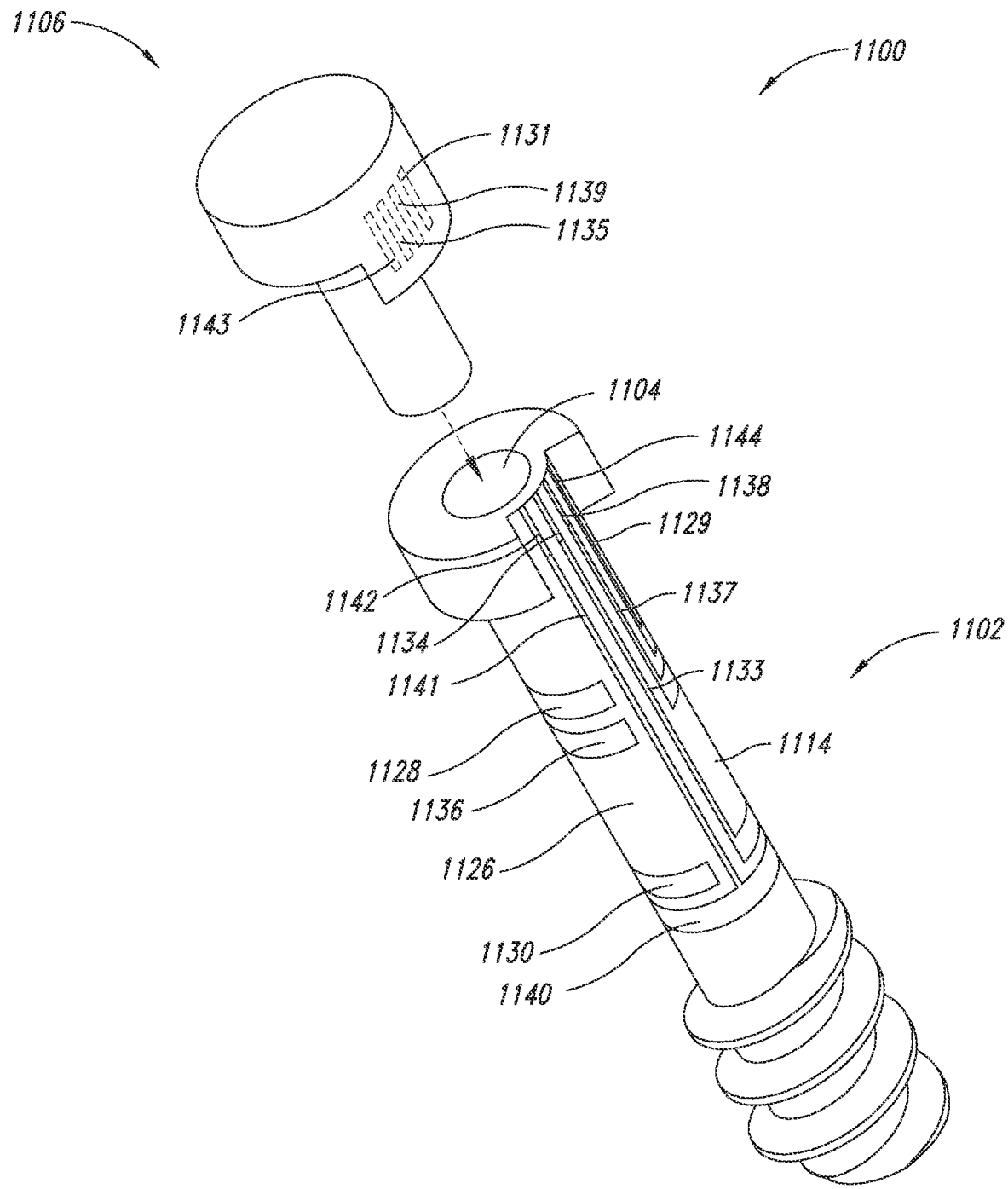
FIGS. 11A and 11B are illustrations of a smart medical device that includes a cannulated screw having four electrodes masked onto the surface of the screw, and an electronics cartridge configured for insertion into the cannulated screw such that four electrical contacts carried by the cartridge align with conductive traces of the electrodes.
Figure 11B:
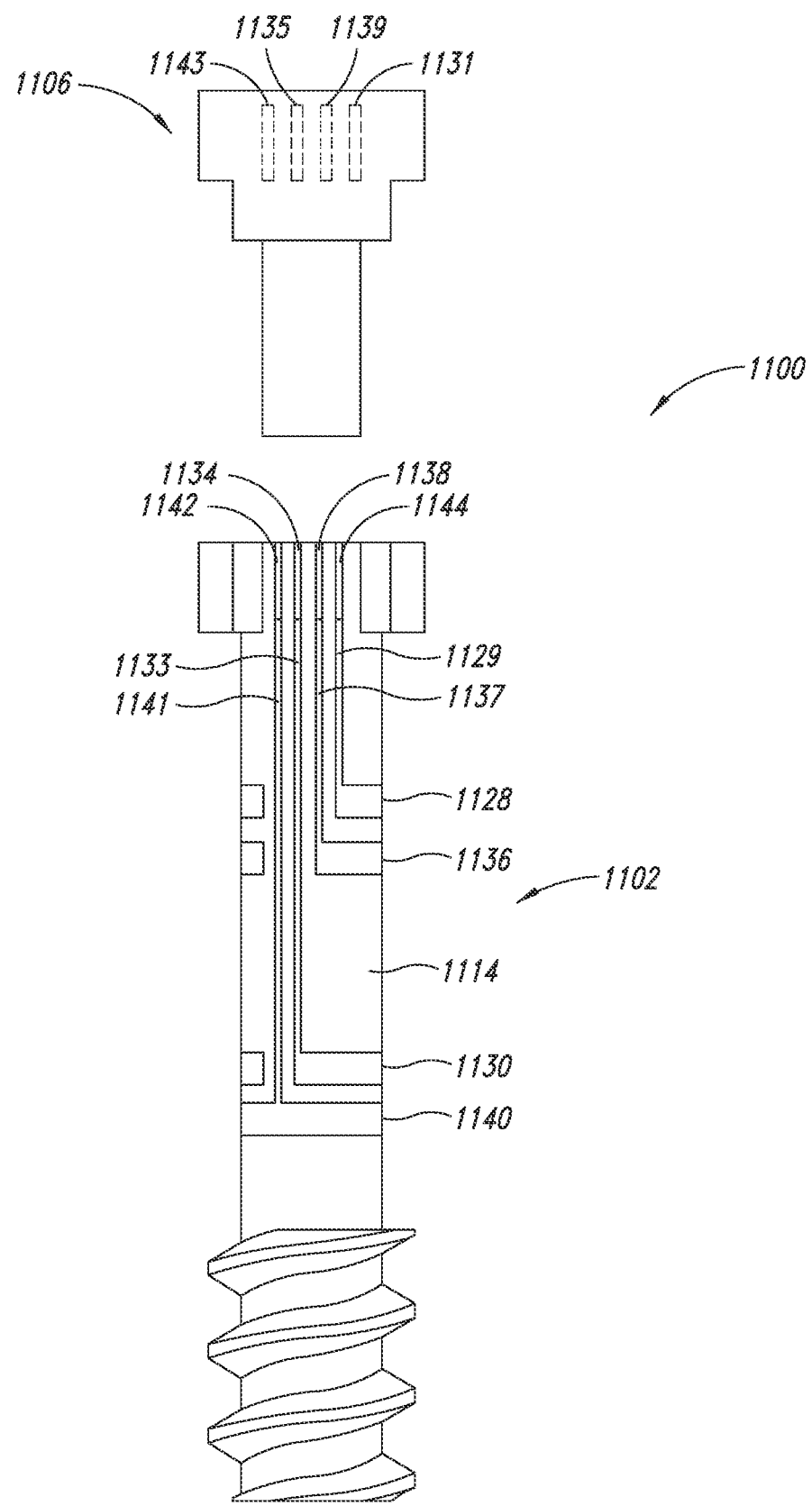

With reference to FIGS. 11A and 11B, in some embodiments a cartridge configuration of a smart medical device 1100 includes a cannulated structure 1102 having a lumen 1104 extending therethrough, and a plurality of electrodes 1128, 1130, 1136, 1140 at an outer surface of the structure, each with a corresponding electrical contacts 1134, 1138, 1142, 1144 also at the outer surface of the structure. As with other embodiments of medical devices, the cannulated structure 1102 is configured to be at least partially implanted in a body. The medical device 1100 also includes an electronics cartridge 1106 including electronics. The electronics cartridge 1106 is configured to be inserted into the lumen 1104 of the cannulated structure 1102. Upon insertion, the electronics cartridge 1106 establishes one or more electrical couplings (not shown) between the electronics of the cartridge and the plurality of electrodes 1128, 1130, 1136, 1140.

The electronics cartridge 1106 includes a plurality of electrical contacts 1131, 1135, 1139, 1143 equal in number to the plurality of electrodes 1128, 1130, 1136, 1140. Each of the electrical contacts 1131, 1135, 1139, 1143 of the electronics cartridge 1106 is positioned to contact a corresponding one of the electrical contacts 1134, 1138, 1142, 1144 of the cannulated structure 1102 upon insertion into the lumen 1104 to thereby establish electrical couplings between the electronics of the cartridge and the electrodes 1128, 1130, 1136, 1140. The electrical contacts 1131, 1135, 1139, 1143 of the electronics cartridge 1106 may be for example, a leaf spring, press fit metal ring, contacting metal surface, etc.

The cannulated structure 1102 includes an electrically conductive substrate having an exterior surface that is at least partially treated or coated with an electrically insulative material 1114. For example, the cannulated structure 1102 may have a titanium substrate that is anodized to make the surface electrically insulated. The plurality of electrodes 1128, 1130, 1136, 1140, e.g., four in the example of FIG. 11, are formed by a conductive coating on the electrically insulative material 1114. A trace 1129, 1133, 1137, 1141, also formed by a conductive coating, extends from each electrode 1128, 1130, 1136, 1140 to a notch formed in the head 1119 of the cannulated structure 1102, where the trace terminates at a respective electrical contact 1134, 1138, 1142, 1144. An insulative coating covers the portion of each trace 1129, 1133, 1137, 1141 that extends between its respective electrode 1128, 1130, 1136, 1140 and respective electrical contact 1134, 1138, 1142, 1144 of the cannulated structure 1102.

Three of the four electrodes 1128, 1132, 1136 are C-shaped and do not fully wrap around the shaft 1126 of the cannulated structure 1002. This allows one or more of the traces 1133, 1137, 1141 of the three more distal electrodes 1130, 1136, 1140 to pass through the gap in the C-shaped electrodes 1128, 1130, 1136 on a single conductive layer. However, by adding an additional insulating layer, all four electrodes 1128, 1132, 1136, 1140 could wrap fully around the shaft 1126 and could cross over top of the conductive connections to other electrodes.

The embodiment of FIGS. 11A and 11B utilizes electroplating on conductive and non-conductive materials on the exterior surface of the substrate of the cannulated structure 1102. First, a non-conductive layer insulates most or all of the substrate. Second, the substrate is masked off and a conductive coating is applied to create the electrical contact 1134, 1138, 1142, 1144, the electrical traces 1129, 1133, 1137, 1141, and the electrodes 1128, 1130, 1136, 1140. Third, a non-conductive plating is applied only to the electrical traces 1129, 1133, 1137, 1141, thereby leaving the electrical contact 1134, 1138, 1142, 1144 and the electrodes 1128, 1130, 1136, 1140 exposed.

Figure 12C:
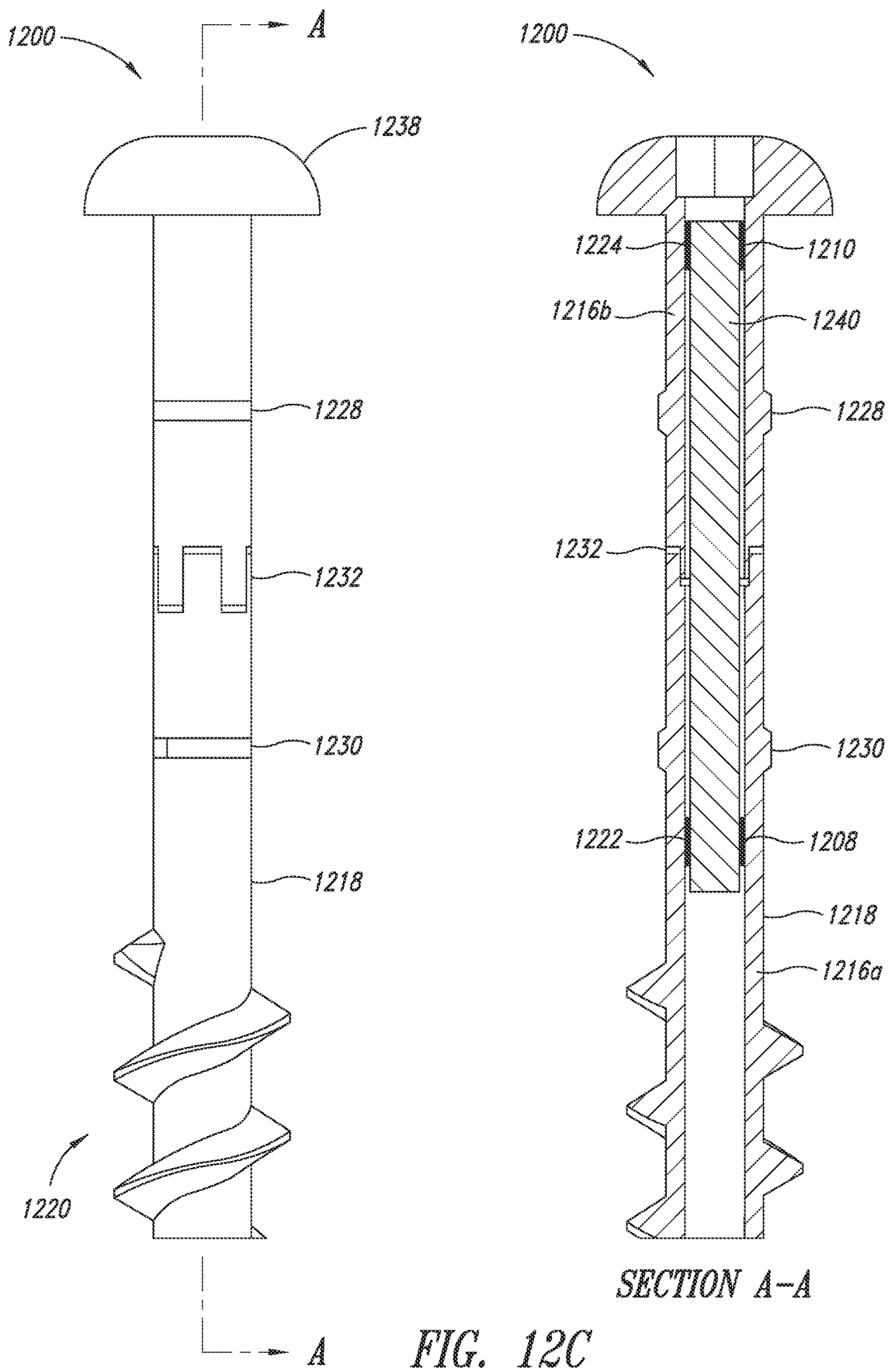

With reference to FIGS. 12A-12C, in some embodiments a cartridge configuration of a smart medical device 1200 includes a multi-piece cannulated structure 1202 having a lumen 1204 extending therethrough, and a plurality of electrodes 1228, 1230 at an outer surface of the structure. As with other embodiments of medical devices, the cannulated structure 1202 is configured to be at least partially implanted in a body. The medical device 1200 also includes an electronics cartridge 1206 including electronics. The electronics cartridge 1206 is configured to be inserted into the lumen 1204 of the multi-piece cannulated structure 1202. Upon insertion, the electronics cartridge 1206 establishes one or more electrical couplings 1208, 1210 between the electronics of the cartridge and the plurality of electrodes 1228, 1230.

The multi-piece cannulated structure 1202 includes a distal piece 1212 and a proximal piece 1214, each having an electrically conductive substrate 1216a, 1216b with an exterior surface that is at least partially coated with an electrically insulative coating 1218. For example, the distal piece 1212 and the proximal piece 1214 may have a titanium substrate 1216a, 1216b that is anodized to make the surface electrically insulated. The distal piece 1212 includes a threaded portion 1220. While the multi-piece cannulated structure 1202 described herein includes two pieces 1212, 1214, each with an electrode 1228, 1230, the cannulated structure 1202 could have more than two pieces. For example, a multi-piece cannulated structure may include four pieces, each with an electrode, and each configured to be coupled to one or more adjacent pieces.

The electronics cartridge 1206 includes a shell 1240 that houses electronics, and a first electrical contact 1222 and a second electrical contact 1224 on the exterior of the shell and that couple to the electronics. The shell 1240 is configured to electrically isolate the two electrical contacts 1222, 1224. To this end, the shell 1240 may be of an electrically non-conductive material, or it may be of an electrically conductive material that is coated with an electrically insulative material. The first electrical contact 1222 is positioned to contact an inner surface of the electrically conductive substrate 1216a of the distal piece 1212 to thereby establish an electrical coupling 1208 between the electronics and a first electrode 1230. The first electrical contact 1222 may be for example, a leaf spring, press fit metal ring, contacting metal surface, etc. The inner surface of the conductive substrate 1216a does not have surface treatment or coating. This allows an electrical connection from the first electrode 1230 to the electronics cartridge 1206 through the conductive substrate 1216a. The second electrical contact 1224 is positioned to contact an inner surface of the electrically conductive substrate 1216b of the proximal piece 1214 to thereby establish an electrical coupling 1210 between the electronics and a second electrode 1228. The second electrical contact 1224 may be for example, a leaf spring, press fit metal ring, contacting metal surface, etc. The inner surface of the conductive substrate 1216b does not have surface treatment or coating. This allows an electrical connection from the second electrode 1228 to the electronics cartridge 1206 through the conductive substrate 1216b.

The first electrode 1230 and the second electrode 1228 correspond to an exposed area of a respective conductive substrate 1216a, 1216b. The electrodes 1228, 1230 may be constructed by masking the surface of the respective conductive substrate 1216a, 1216b prior providing the electrically insulative coating 1218, or in cases where the coating is already applied, by machine surfacing the conductive substrate to remove the electrically insulative coating. The first electrode 1230 and the second electrode 1228 are electrically isolated from each other by a non-conductive joint 1232 between the distal piece 1212 and the proximal piece 1214 of the cannulated structure 1202.

The non-conductive joint 1232 may be an adhesive that is used to secure the proximal piece 1214 to the distal piece 1212 during implant of the medical device 1200. For example, during implant of the medical device 1200 the distal piece 1212 is first implanted into a portal hole drilled through boney tissue. Next, a non-conductive adhesive material is applied to the end of the proximal piece 1214 and the piece is inserted into the portal hole until it mechanically couples with the distal piece 1212. The coupling of the distal piece 1212 and the proximal piece 1214 may be provided by respective mechanical features 1234, 1236 of the pieces, such as respective sets of notches and protrusions that mate together. Next, the electronics cartridge 1206 is inserted into the lumen 1204 through the head 1238 of the proximal piece 1214. In an alternate implant procedure, the electronics cartridge 1206 may be inserted in the distal piece 1212 prior to coupling the proximal piece 1214 to the distal piece. In yet another procedure, the distal piece 1212 and the proximal piece 1214 may be assembled together outside the body, prior to implant, and then seated in the bone using any of the implant tools and techniques described below with reference to FIGS. 18A-18J. The electronics cartridge 1206 is then inserted into the assembled cannulated structure 1202.

With reference to FIGS. 13A-13D, in some embodiments a cartridge configuration of a smart medical device 1300 includes a cannulated screw 1302 and an electronics cartridge 1306 configured for insertion into the cannulated screw. In this embodiment, the electronics cartridge 1306 includes one or more electrodes and the cannulated screw 1302 includes one or more apertures. In some configurations, various electronics of the electronics cartridge 1306 are located in a head 1322 of the cartridge, and a power supply 1354 is located in a portion of a shaft 1326 of the electronics cartridge beneath the head. This and other structure and characteristics of the cannulated screw 1302 and the electronics cartridge 1306 are substantially the same as those described above for the cannulated screw 102 and an electronics cartridge 106 of the embodiment of FIGS. 1A-1C. Accordingly, such details are not repeated here. Instead further description of the smart medical device 1300 of FIGS. 13A-13D focuses on its distinct features.

Figure 13A:
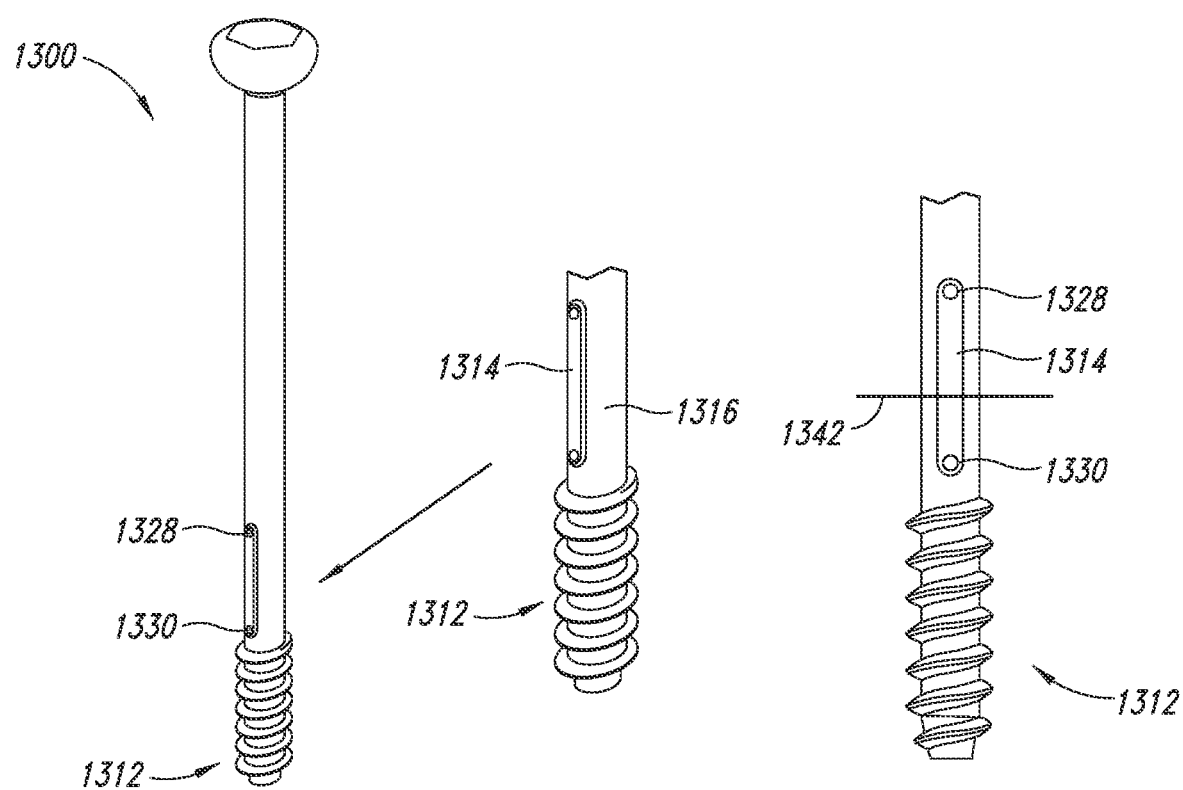
FIGS. 13A, 13B, 13C, and 13D are illustrations of another configuration of a smart medical device that includes a cannulated screw (FIG. 13C) having a slot, and an electronics cartridge (FIG. 13D) configured for insertion into the cannulated screw such that electrodes carried by the cartridge align with the slot.
Figure 13B:
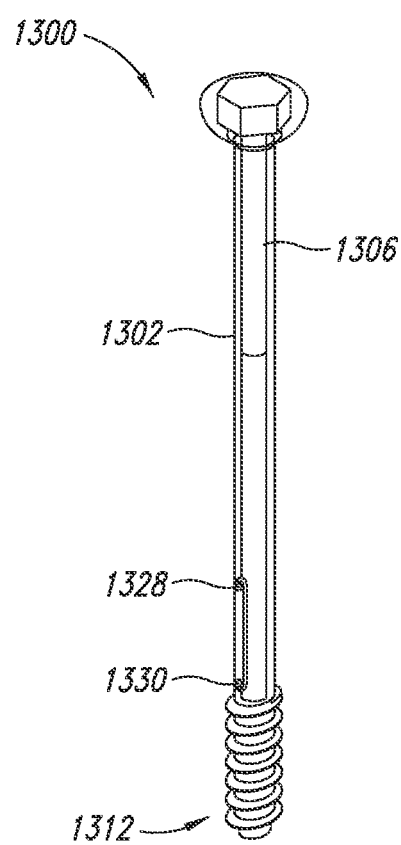
Figure 13C:
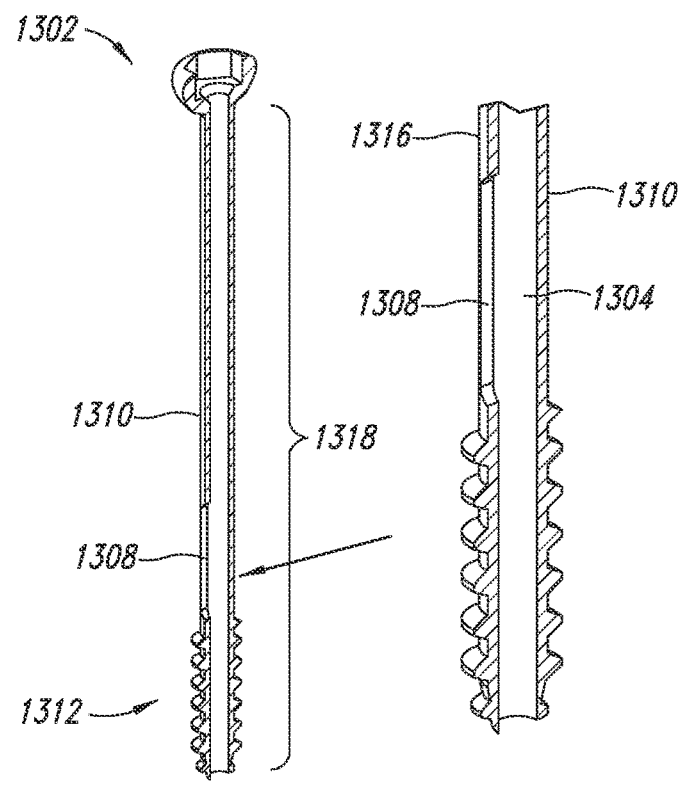

With reference to FIG. 13C, the cannulated screw 1302 includes an aperture 1308 in the form of a slot through its sidewall 1310. The slot 1308 is located in a region of the shaft 1318 of the cannulated screw 1302 proximal the threaded region 1312 of the screw. In some embodiments an electrically insulative coating is applied to the outer surface 1316 of the cannulated screw 1302 in the area of the slot 1308.

Figure 13D:
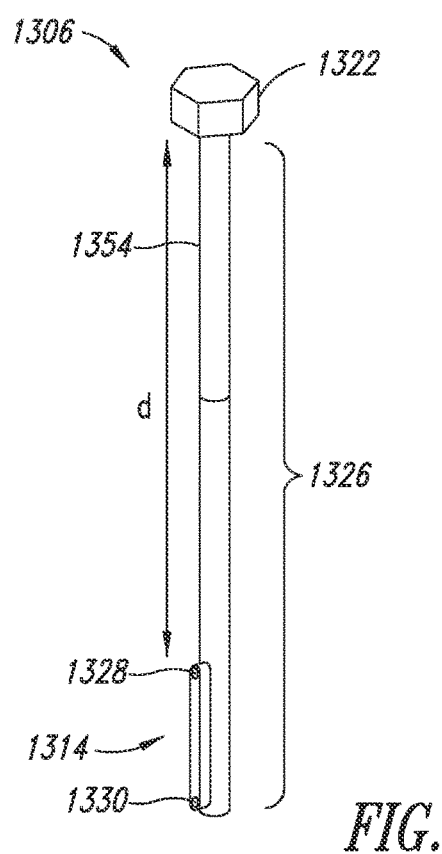

With reference to FIG. 13D, the electronics cartridge 1306 include a spring-loaded electrode assembly 1314 that extends radially outward from the surface of the shaft 1326 of the cartridge. To this end, the electrode assembly 1314 is biased relative to the surface of the shaft 1326 to enable the electronics cartridge to transition between a compressed state during which the outer surface of the electrode assembly 1314 is substantially flush with the surface of the of the shaft 1326, and an expanded state during which the outer surface of the electrode assembly 1314 is elevated or offset from the surface of the shaft 1326 to extend through the slot 1308. The electrode assembly 1314 includes a pair of electrodes 1328, 1330 that are spaced apart by a distance of at least 1 mm.

With continued reference to FIG. 13D, the form factor, e.g., geometric cross-section and thickness, of the electrode assembly 1314 and the distance d between the bottom of the head 1322 of the electronics cartridge 1306 and the top of the electrode projection are such that when the electronics cartridge is fully inserted into the lumen 1304 of the cannulated screw 1302, the electrode assembly 1314 aligns with and extends through the slot 1308 to position the electrodes 1328, 1330 outward from the outer surface 1316 of the cannulated screw.

The cannulated screw 1302 and the electronics cartridge 1306 may include one or more mechanisms similar to those described above with reference to FIGS. 2A-5B that secure the cartridge within the screw. Furthermore, extension of the electrode assembly 1314 through the slot 1308 also serves to secure the electronics cartridge 1306 within the cannulated screw 1302.

With reference to FIGS. 13A-13D, during implant of the medical device 1300 for treatment of a bone fracture 1342, the cannulated screw 1302 may be implanted across the bone fracture such that the fracture is located between the opposite ends of the slot 1308, and preferably, midway between the ends. As such, when the electronics cartridge 1306 is inserted into the cannulated screw 1302, the electrodes 1328, 1330 are on opposite sides of the bone fracture 1342.

The electrodes 1328, 1330, in combination with other electronics of the medical device 1300, may define a sensor or sensor system configured to monitor electrical properties of tissue. In some embodiments, the sensor system is an impedance sensor that functions as an EIS sensor to detect the location of a bone fracture and monitor the healing status of such fractures. As describe further below, in this arrangement, the medical device 1300 enables the collection of data through the electrodes 1328, 1330 for purposes of bone fracture 1342 characterization and healing state analysis. The electrodes 1328, 1330, in combination with other electronics of the medical device 1300, may define a tissue conductive communications interface. Details of the tissue conductive communication interface are disclosed further below.

With reference to FIGS. 14A-14D, in some embodiments a cartridge configuration of a smart medical device 1400 includes a cannulated screw 1402 and an electronics cartridge 1406 configured for insertion into the cannulated screw. In some configurations, various electronics of the electronics cartridge 1406 are located in a head 1422 of the cartridge, and a power supply 1454 is located in a portion of a shaft 1426 of the electronics cartridge beneath the head. This and other structure and characteristics of the cannulated screw 1402 and the electronics cartridge 1406 are substantially the same as those described above for the cannulated screw 102 and an electronics cartridge 106 of the embodiment of FIGS. 1A-1C. Accordingly, such details are not repeated here. Instead further description of the smart medical device 1400 of FIGS. 14A-14D focuses on its distinct features.

Figure 14A:
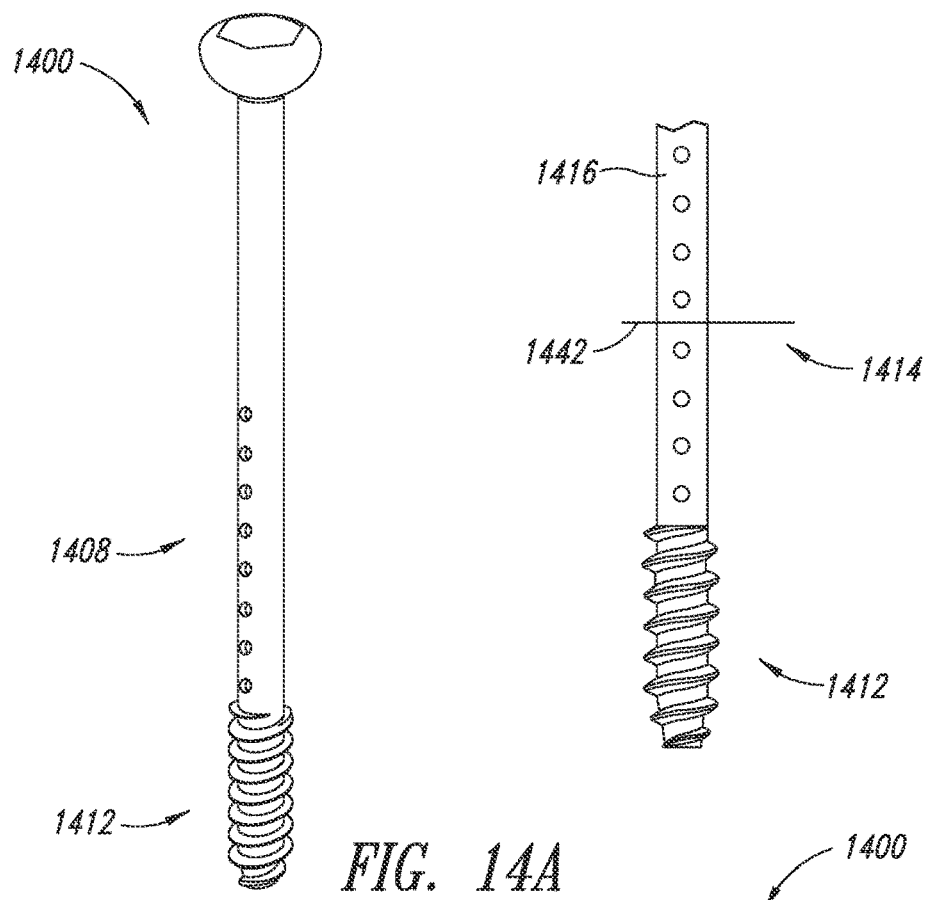
FIGS. 14A, 14B, 14C, and 14D are illustrations of another configuration of a smart medical device that includes a cannulated screw (FIG. 14C) having a number of apertures, and an electronics cartridge (FIG. 14D) configured for insertion into the cannulated screw such that electrodes carried by the cartridge align with the apertures.
Figure 14B:
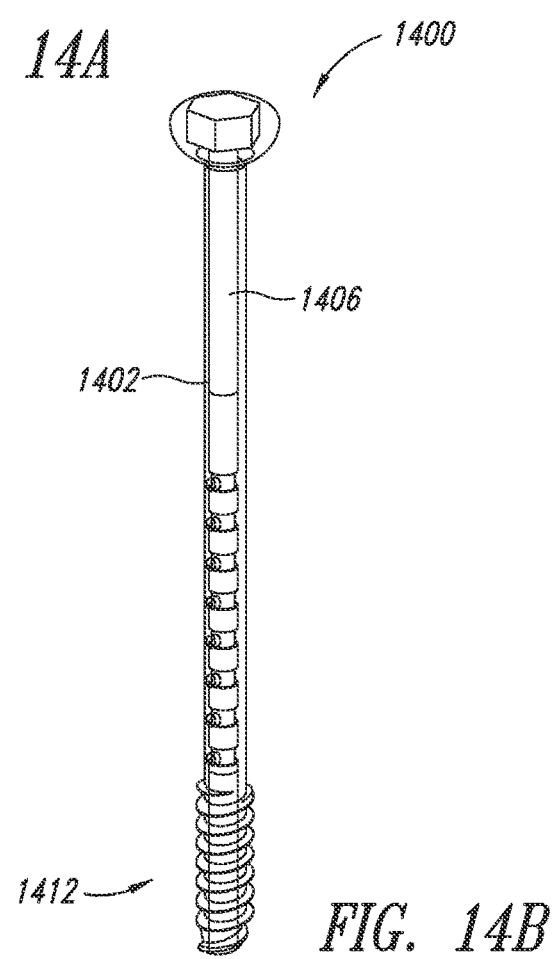
Figure 14C:
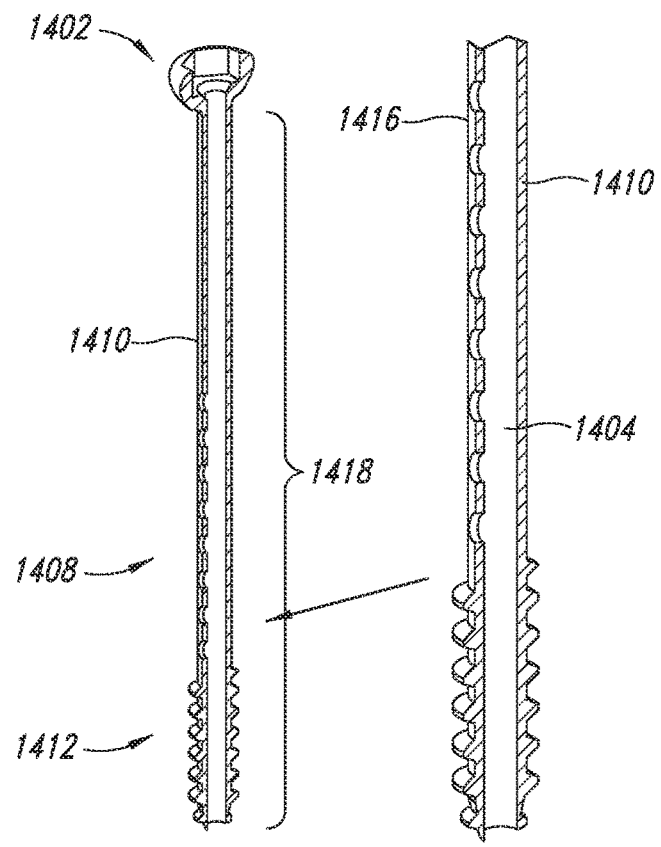

With reference to FIG. 14C, the cannulated screw 1402 includes an array of apertures 1408 through its sidewall 1410. In the cannulated screw 1402 of FIG. 14C there are eight individual apertures in the array of apertures 1408. The array of apertures 1408 is located in a region of the shaft 1418 of the cannulated screw 1402 proximal the threaded region 1412 of the screw. In some embodiments an electrically insulative coating is applied to the outer surface 1416 of the cannulated screw 1402 in the area of the array of apertures 1408. In some embodiments an electrically insulative coating is applied to the outer surface 1416 of the cannulated screw 1402 over the entire length, except for the threaded region 1412.

Figure 14D:
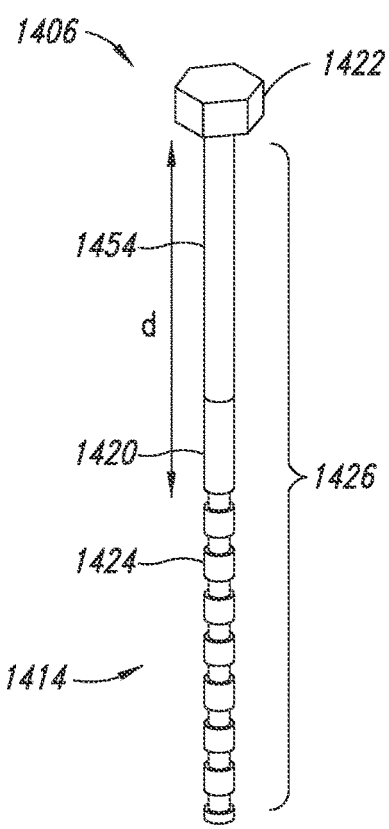

With reference to FIG. 14D, the electronics cartridge 1406 includes an array of electrodes 1414. In the electronics cartridge 1406 of FIG. 14D there are eight individual electrodes in the array of electrodes 1414. The array of electrodes 1414 includes a number of individual electrodes separated by seals 1424 that seal off and electrically isolate the individual electrodes from each other. In some embodiments, these seals 1424 correspond to regions of the hollow shell of the electronics cartridge 1406, which as previously described, is formed of an electrically insulative material. In other embodiments, these seals 1424 may be rings formed of a non-conductive metallic or polymeric material or biocompatible elastomer that is placed around the shell of the electronics cartridge 1406. The distance between adjacent individual electrodes may be at least 1 mm. These individual electrodes are recessed relative to the outer surface 1420 of the shaft 1426 of the electronics cartridge 1406. In one configuration, the individual electrodes are ring electrodes.

With continued reference to FIG. 14D, the distance d between the bottom of the head 1422 of the electronics cartridge 1406 and the top of the array of electrodes 1414 is such that when the electronics cartridge is fully inserted into the lumen 1404 of the cannulated screw 1402, each individual electrode in the array of electrodes 1414 aligns with a corresponding one of the apertures in the array of apertures 1408. Due to the recessed arrangement of the individual electrodes relative to the shaft 1426 of the electronics cartridge 1406, upon insertion of the electronics cartridge 1406 into the cannulated screw 1402, a donut shaped space is formed between the outer surface of the individual electrodes and the inner wall of the cannulated screw 1402. Electrode-tissue interfaces between the electrode surfaces and tissue are established by the ingress of issue through the apertures of the cannulated screw 1402 into the donut shaped space around the electrodes in the array of electrodes 1414.

The cannulated screw 1402 and the electronics cartridge 1406 may include one or more mechanisms similar to those described above with reference to FIGS. 2A-5B that secure the cartridge within the screw. Furthermore, one or more electrodes in the array of electrodes 1414 may be configured to expand radially to extend at least partially into, and possibly entirely through, one of the apertures in the array of apertures 1408. To this end, the electrode may be formed of a material that has shape memory, e.g., platinum, platinum iridium, such that when the electronics cartridge 1406 is placed in a defined location in the orthopedic position, the temperature change causes the electrode to change from a set configuration to another shape set configuration that extends the electrode into an aperture. Distention change of the electrode can be 0.001 inch or greater in a axial, radial or both directions to extends the electrode into and through an aperture to thereby secure the electronics cartridge 1406 in the cannulated screw 1402, and to improve contact between the electrode surface and the boney tissue interface.

With reference to FIGS. 14A-14D, during implant of the medical device 1400 for treatment of a bone fracture 1442, the cannulated screw 1402 may be implanted across the bone fracture such that the fracture is located between the opposite ends of the array of apertures 1408, and preferably, midway between the ends. As such, when the electronics cartridge 1406 is inserted into the cannulated screw 1402, one or more of the electrodes are on opposite sides of the bone fracture 1442.

At least two select electrodes of the array of electrodes 1414, in combination with other electronics of the medical device 1400, may define a sensor or sensor system configured to monitor electrical properties of tissue. In some embodiments, the sensor system is an impedance sensor that functions as an EIS sensor to detect the location of a bone fracture and monitor the healing status of such fractures. As describe further below, in this arrangement, the medical device 1400 enables the collection of data through select electrodes on opposite sides of the bone fracture 1442 for purposes of bone fracture characterization and healing state analysis. The two select electrodes of the array of electrodes 1414, in combination with other electronics of the medical device 1400, may define a tissue conductive communications interface. Details of the tissue conductive communication interface are disclosed further below.

With reference to FIGS. 15A-15D, in some embodiments a cartridge configuration of a smart medical device 1500 includes a cannulated screw 1502 and an electronics cartridge 1506 configured for insertion into the cannulated screw. In some configurations, various electronics of the electronics cartridge 1506 are located in a head 1522 of the cartridge, and a power supply 1554 is located in a portion of a shaft 1526 of the electronics cartridge beneath the head. This and other structure and characteristics of the cannulated screw 1502 and the electronics cartridge 1506 are substantially the same as those described above for the cannulated screw 102 and an electronics cartridge 106 of the embodiment of FIGS. 1A-1C. Accordingly, such details are not repeated here. Instead further description of the smart medical device 1500 of FIGS. 15A-15D focuses on its distinct features.

Figure 15A:
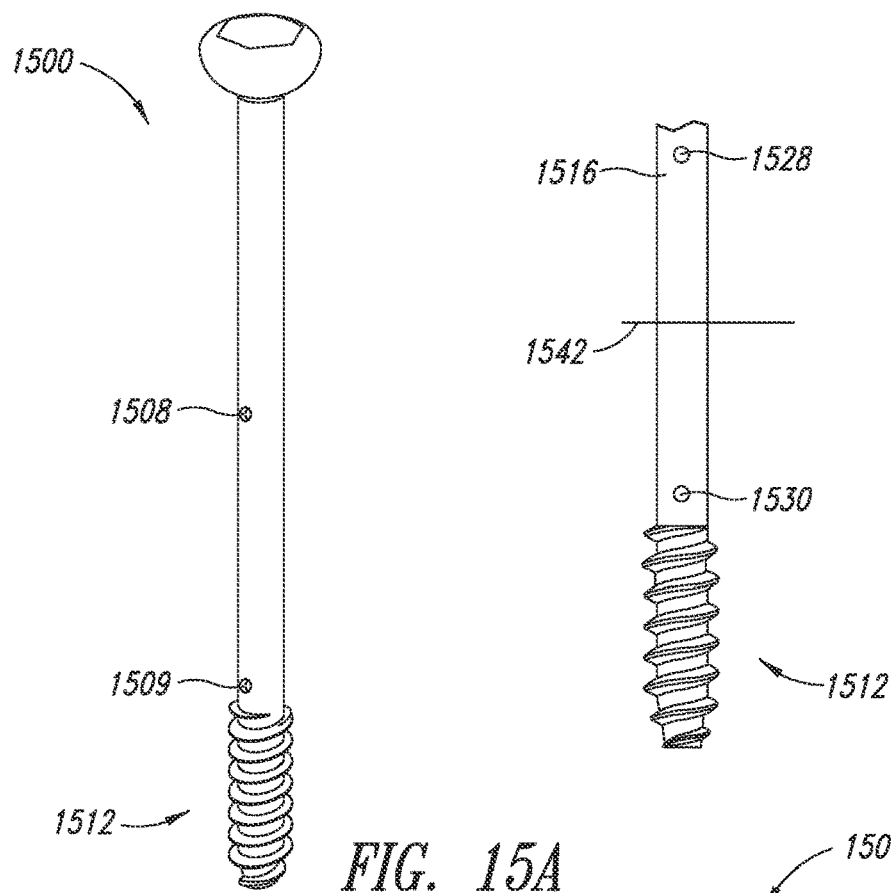
FIGS. 15A, 15B, 15C, and 15D are illustrations of another configuration of a smart medical device that includes a cannulated screw (FIG. 15C) having a pair of apertures, and an electronics cartridge (FIG. 15D) configured for insertion into the cannulated screw such that a pair of electrodes carried by the cartridge align with the pair of apertures.
Figure 15B:
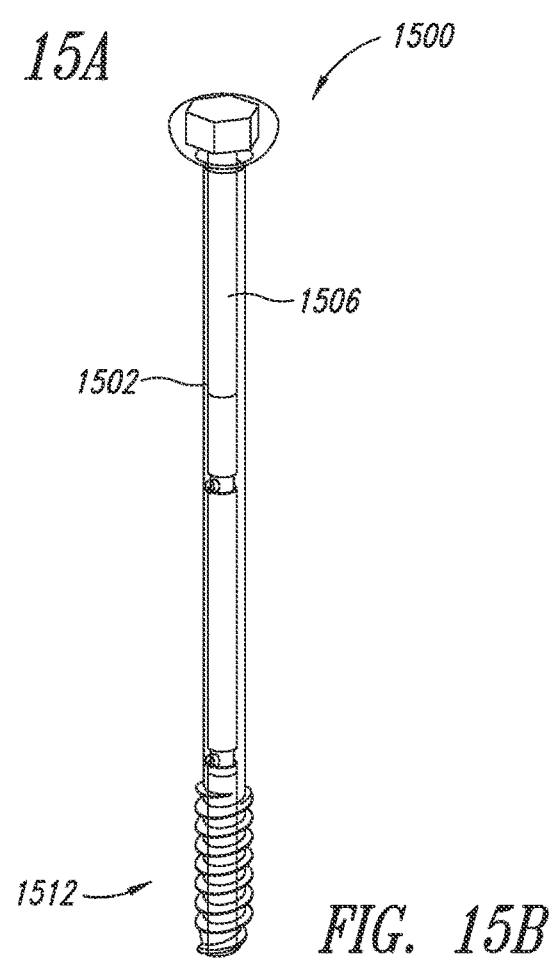
Figure 15C:
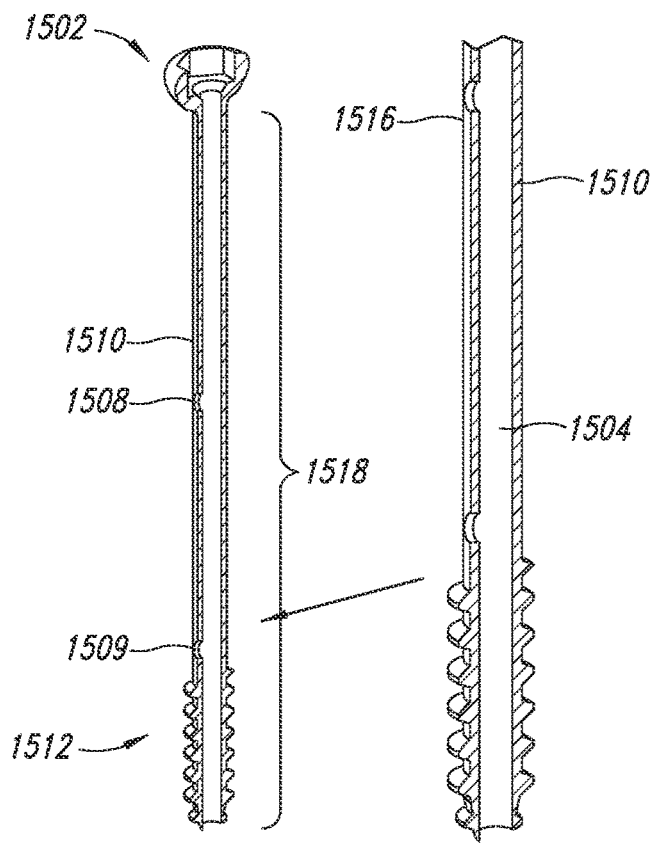

With reference to FIG. 15C, the cannulated screw 1502 includes a pair of apertures 1508, 1509 through its sidewall 1510. The pair of apertures 1508, 1509 is located in a region of the shaft 1518 of the cannulated screw 1502 proximal the threaded region 1512 of the screw. In some embodiments an electrically insulative coating is applied to the outer surface 1516 of the cannulated screw 1502 in the area of the pair of apertures 1508, 1509. In some embodiments an electrically insulative coating is applied to the outer surface 1516 of the cannulated screw 1502 over the entire length, except for the threaded region 1512.

Figure 15D:
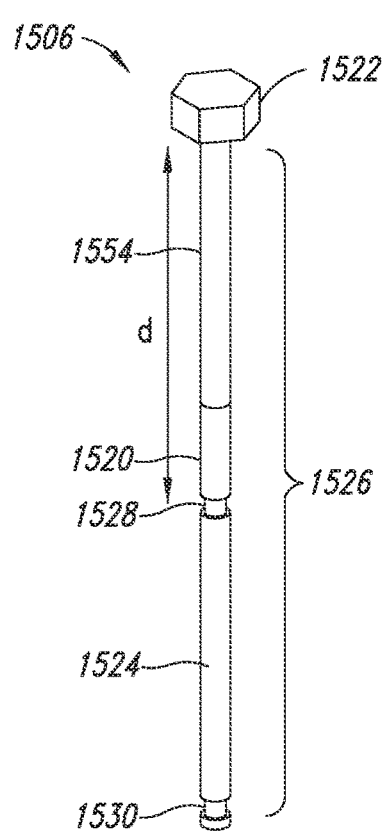

With reference to FIG. 15D, the electronics cartridge 1506 includes a pair of electrodes 1528, 1530. The electrodes 1528, 1530 are separated by a seal 1524 that seals off and electrically isolates the individual electrodes from each other. In some embodiments, this seal 1524 correspond to a region of the hollow shell of the electronics cartridge 1506, which as previously described, is formed of an electrically insulative material. In other embodiments, this seal 1524 may be a ring formed of a non-conductive metallic or polymeric material or biocompatible elastomer that is placed around the shell of the electronics cartridge 1506. The distance between the electrodes 1528, 1530 may be at least 1 mm. The electrodes 1528, 1530 are recessed relative to the outer surface 1520 of the shaft 1526 of the electronics cartridge 1506. In one configuration, the individual electrodes 1528, 1530 are ring electrodes.

With continued reference to FIG. 15D, the distance d between the bottom of the head 1522 of the electronics cartridge 1506 and the proximal electrode 1528 is such that when the electronics cartridge is fully inserted into the lumen 1504 of the cannulated screw 1502, each electrode 1528, 1530 aligns with a corresponding aperture 1508, 1509. Due to the recessed arrangement of the individual electrodes 1528, 1530 relative to the shaft 1526 of the electronics cartridge 1506, upon insertion of the electronics cartridge 1506 into the cannulated screw 1502, a donut shaped space is formed between the outer surface of individual electrodes and the inner wall of the cannulated screw 1502. Electrode-tissue interfaces between the electrode surfaces and tissue is established by the ingress of issue through the apertures 1508, 1509 of the cannulated screw 1502 into the donut shaped space around the electrodes 1528, 1530.

The cannulated screw 1502 and the electronics cartridge 1506 may include one or more mechanisms similar to those described above with reference to FIGS. 2A-5B that secure the cartridge within the screw. Furthermore, one or more of the electrodes 1528, 1530 may be configured to expand radially to extend at least partially into, and possibly entirely through, one of the apertures 1508, 1509 as described above with reference to FIG. 14D.

With reference to FIGS. 15A-15D, during implant of the medical device 1500 for treatment of a bone fracture 1542, the cannulated screw 1502 may be implanted across the bone fracture such that the fracture is located between the pair of apertures 1508, 1509 and preferably, midway between the apertures. As such, when the electronics cartridge 1506 is inserted into the cannulated screw 1502, the electrodes 1528, 1530 are on opposite sides of the bone fracture 1542.

The electrodes 1528, 1530, in combination with other electronics of the medical device 1500, may define a sensor or sensor system configured to monitor electrical properties of tissue. In some embodiments, the sensor system is an impedance sensor that functions as an EIS sensor to detect the location of a bone fracture and monitor the healing status of such fractures. As describe further below, in this arrangement, the medical device 1500 enables the collection of data through these electrodes for purposes of bone fracture characterization and healing state analysis. The electrodes 1528, 1530, in combination with other electronics of the medical device 1500, may define a tissue conductive communications interface. Details of the tissue conductive communication interface are disclosed further below.

With reference to FIGS. 16A-16D, in some embodiments a cartridge configuration of a smart medical device 1600 includes a cannulated screw 1602 and an electronics cartridge 1606 configured for insertion into the cannulated screw. In some configurations, various electronics of the electronics cartridge 1606 are located in the head 1622, and a power supply 1654 is located in a portion of the shaft 1626 of the electronics cartridge beneath the head. This and other structure and characteristics of the cannulated screw 1602 and the electronics cartridge 1606 are substantially the same as those described above for the cannulated screw 102 and an electronics cartridge 106 of the embodiment of FIGS. 1A-1C. Accordingly, such details are not repeated here. Instead, further description of the smart medical device 1600 of FIGS. 16A-16D focuses on its distinct features.

Figure 16A:
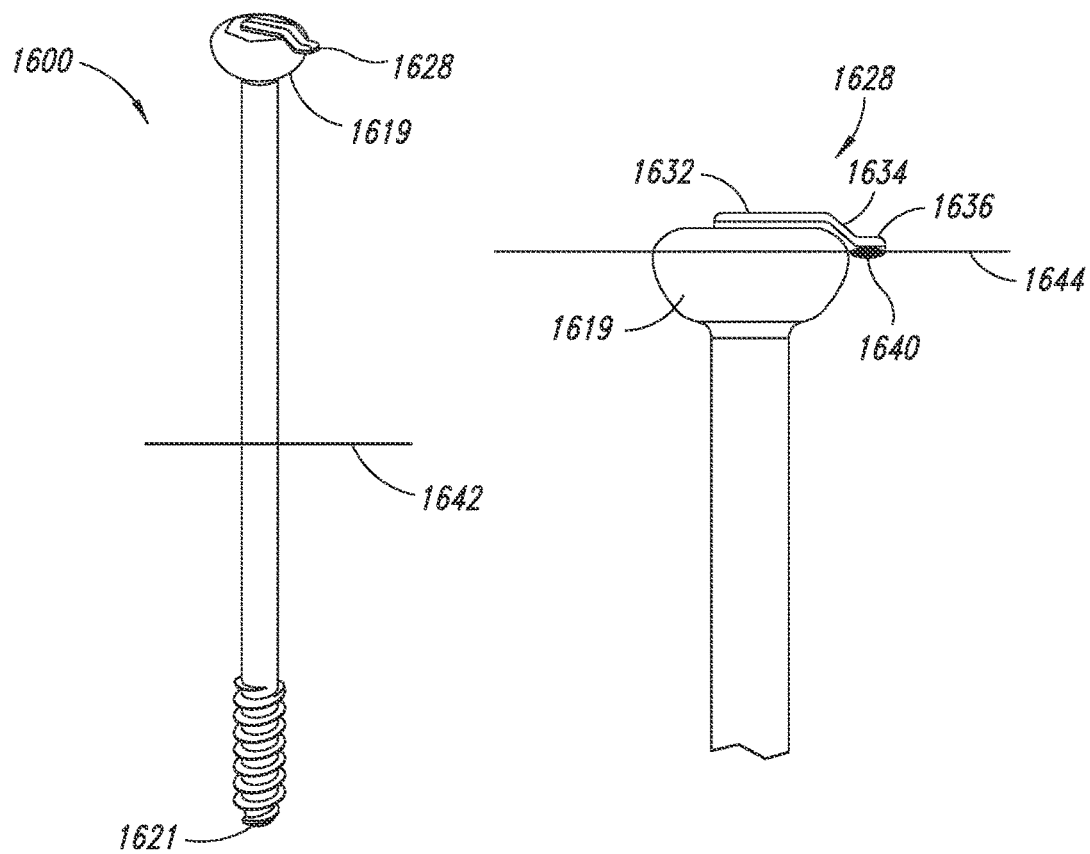
FIGS. 16A, 16B, 16C, and 16D are illustrations of another configuration of a smart medical device that includes a cannulated screw (FIG. 16C), and an electronics cartridge (FIG. 16D) configured for insertion into the cannulated screw such that a tip electrode aligns with the distal end of the cannulated screw, and a cap electrode also carried by the cartridge is exposed at the head of the screw.
Figure 16B:
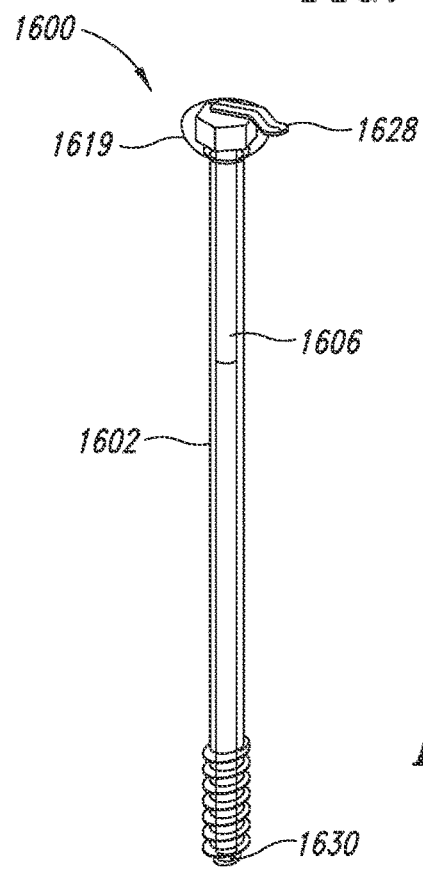
Figures 16C, 16D:
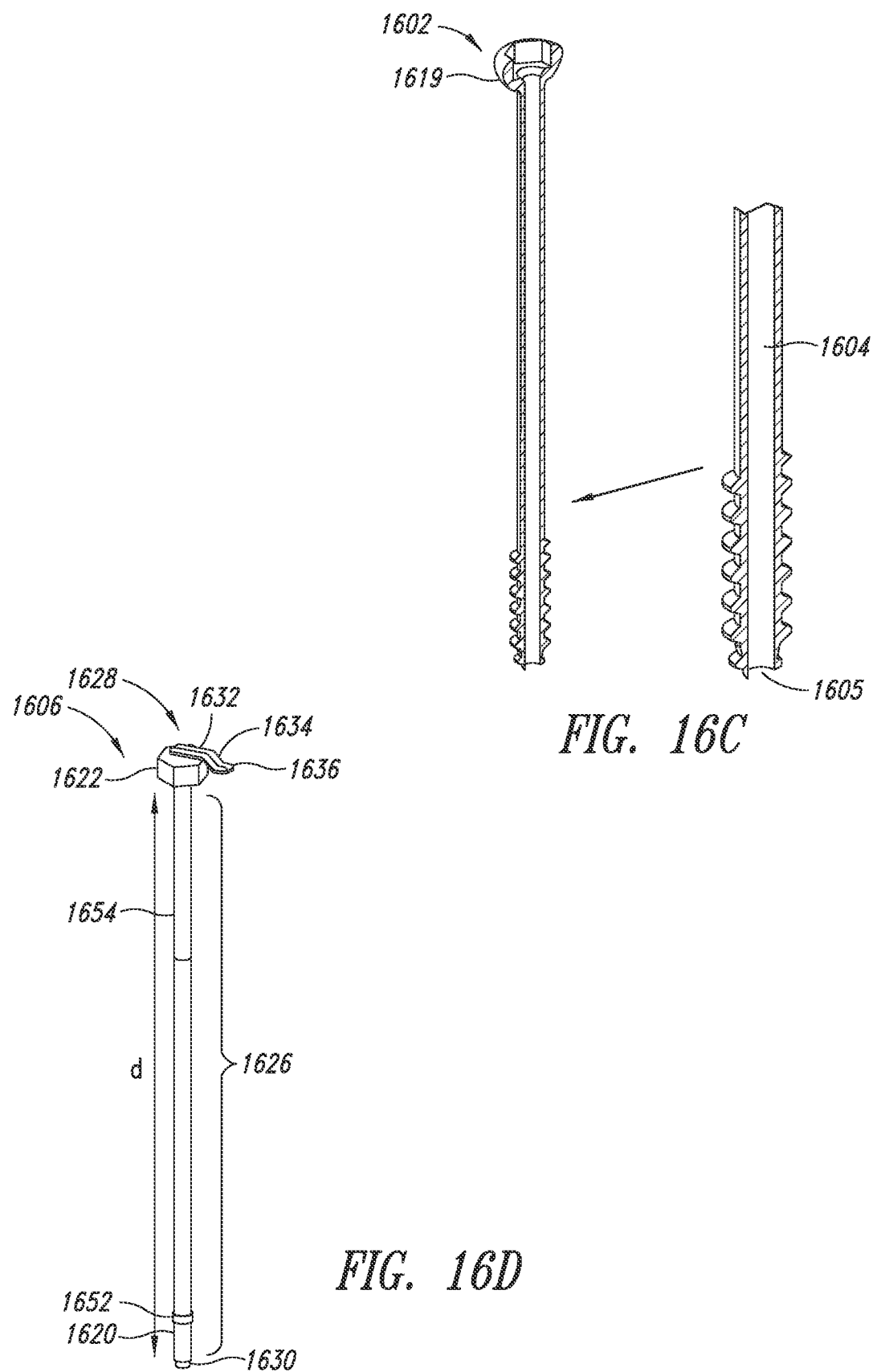

With reference to FIG. 16D, the electronics cartridge 1606 includes a cap electrode 1628 associated with the head 1622 of the cartridge and a tip electrode 1630 at the distal end of the cartridge. The distance d between the bottom of the head 1622 of the electronics cartridge 1606 and the top of the tip electrodes 1630 is such that when the electronics cartridge is fully inserted into the lumen 1604 of the cannulated screw 1602 (as shown in FIG. 16B), the tip electrode 1630 is adjacent to an exposed at the distal end 1605 of the lumen 1604 of the cannulated screw, and the cap electrode 1628 is exposed at the head 1619 of the screw. In this embodiment, exposure of the cap electrode 1628 and the tip electrode 1630 is provided without the need for a sidewall slot or apertures, as included for example, in the embodiments of FIGS. 13A-15D.

With continued reference to FIG. 16D, in some embodiments the cap electrode 1628 includes a first portion 1632 that lies in a plane parallel with the top surface of the head 1622, a second portion 1634 that bends downward from the end of the first portion and extends in a plane different from the plane of the first portion and away from the side of the head, and a third portion 1636 that bends upward from the end of the second portion and extends in a plane substantially parallel with the plane of the first portion 1632 and further away from the side of the head.

With reference to FIG. 16A, exposure of the cap electrode 1628 at the head 1619 of the cannulated screw 1602 allows for an electrode-tissue interface 1640 to be formed between the third portion 1636 of the cap electrode 1628 and a surface of boney tissue 1644 upon insertion of the electronics cartridge 1606 in the cannulated screw 1602. In this embodiment, because a portion of the cap electrode 1628, e.g., the first portion 1632 and possibly the second portion 1634, contacts the head 1619 of the cannulated screw 1602, the head of the cannulated screw 1602 may be coated with an electrically insulative material, or the entire cannulated screw 1602 may be coated with an electrically insulative material.

In other embodiments (not shown), rather than having a cap electrode 1628 that is exposed on the head 1622 of the electronics cartridge 1606, the cartridge may include an upper electrode internal to the cartridge (either at the head 1622 or an upper region of the shaft 1626) that is exposed at a side surface of the cartridge to make electrical contact with an electrically conductive portion of the cannulated screw 1602. In this embodiment, the entire screw, except for the portion that makes contact with the upper electrode, would be coated with an electrically insulative material.

Returning to FIG. 16D, the tip electrode 1630 is recessed relative to the outer surface 1620 of the shaft 1626 of the electronics cartridge 1606. In one configuration, the tip electrode 1630 is a ring electrode. Due to the recessed arrangement of the tip electrode 1630 relative to the shaft 1626 of the electronics cartridge 1606, upon insertion of the electronics cartridge 1606 into the cannulated screw 1602, a donut shaped space is formed between the outer surface of the tip electrode 1630 and the inner wall of the cannulated screw 1602. An electrode-tissue interface between the tip electrode 1630 and tissue is established by the ingress of issue through the distal end 1605 of the cannulated screw 1602 into the donut shaped space around the tip electrode. A seal 1652 located around the shaft 1626 and proximal the tip electrode 1630 prevents the ingress of tissue and body fluids to parts of the medical device 1600 proximal the seal, including in particular, the cap electrode 1628. The seal 1652 may be formed of a biocompatible elastomer or a polymeric material with a 20 A durometer or greater, or a polymeric fiber doped material or a polymeric encased material that can swell when exposed to a solution, or a metallic material that is non-conductive.

The cannulated screw 1602 and the electronics cartridge 1606 may include one or more mechanisms similar to those described above with reference to FIGS. 2A-5B that secure the cartridge within the screw. Furthermore, the tip electrode 1630 may be configured to expand radially and axially to extend at least partially into, and possibly entirely through, the distal end 1605 of the cannulated screw, as described above with reference to FIG. 14D. Such expansion may serve to secure the electronics cartridge 1606 within the cannulated screw 1602.

With reference to FIGS. 16A-16D, during implant of the medical device 1600 for treatment of a bone fracture 1642, the cannulated screw 1602 may be implanted across the bone fracture such that the fracture is located between the head 1619 and the distal end 1621 of the screw, and preferably, midway between the head and end. As such, when the electronics cartridge 1606 is inserted into the cannulated screw 1602, the electrodes 1628, 1630 are on opposite sides of the bone fracture 1642.

The electrodes 1628, 1630, in combination with other electronics of the medical device 1600, may define a sensor or sensor system configured to monitor electrical properties of tissue. In some embodiments, the sensor system is an impedance sensor that functions as an EIS sensor to detect the location of a bone fracture and monitor the healing status of such fractures. As describe further below, in this arrangement, the medical device 1600 enables the collection of data through these electrodes for purposes of bone fracture characterization and healing state analysis. The electrodes 1628, 1630, in combination with other electronics of the medical device 1600, may define a tissue conductive communications interface. Details of the tissue conductive communication interface are disclosed further below.

Figure 17A:
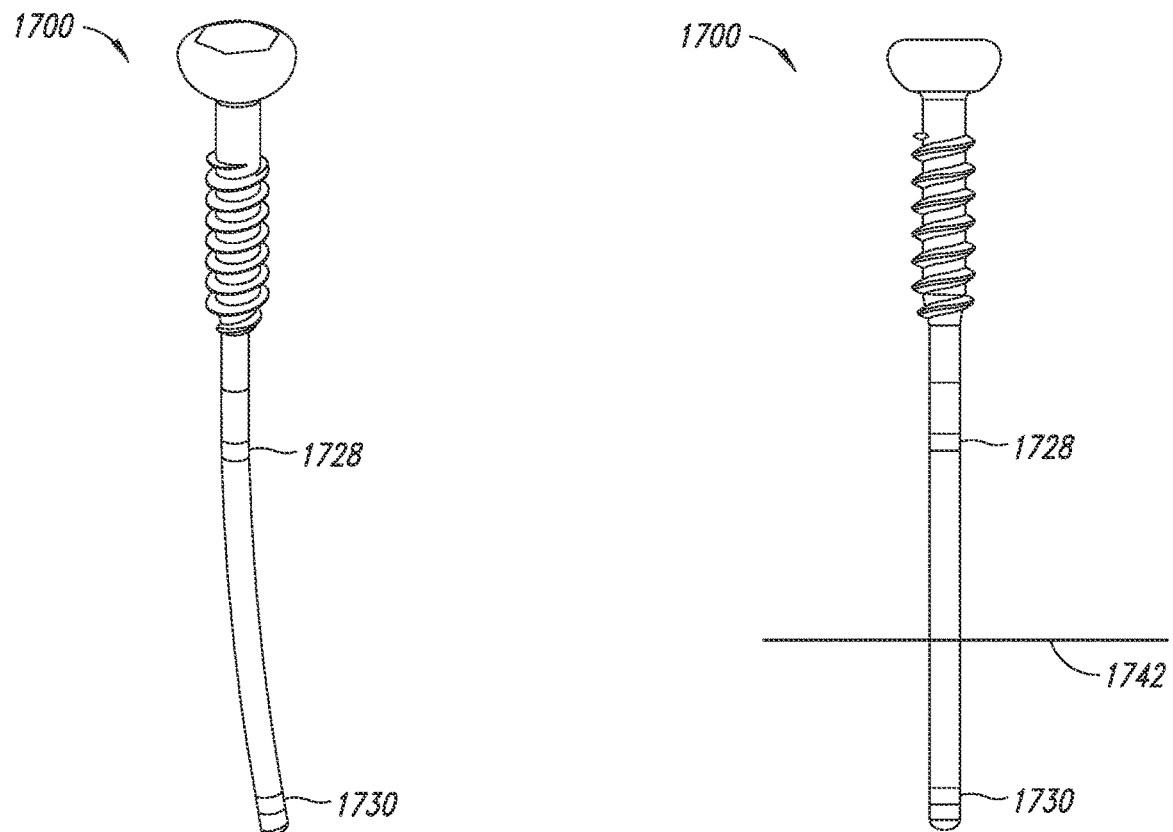
FIGS. 17A, 17B, and 17C are illustrations of another configuration of a smart medical device that includes a cannulated screw (FIG. 17B), and an electronics cartridge (FIG. 17C) configured for insertion into the cannulated screw such that a portion of the cartridge that carries a distal electrode and a proximal electrode extends through the distal end of the cannulated screw.
Figure 17B:
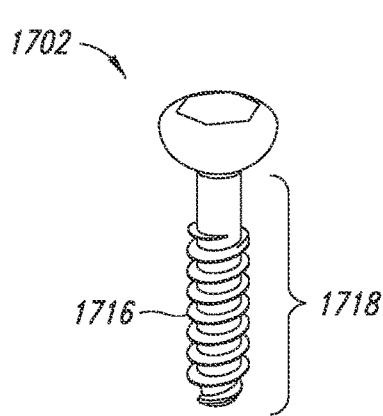
Figure 17C:
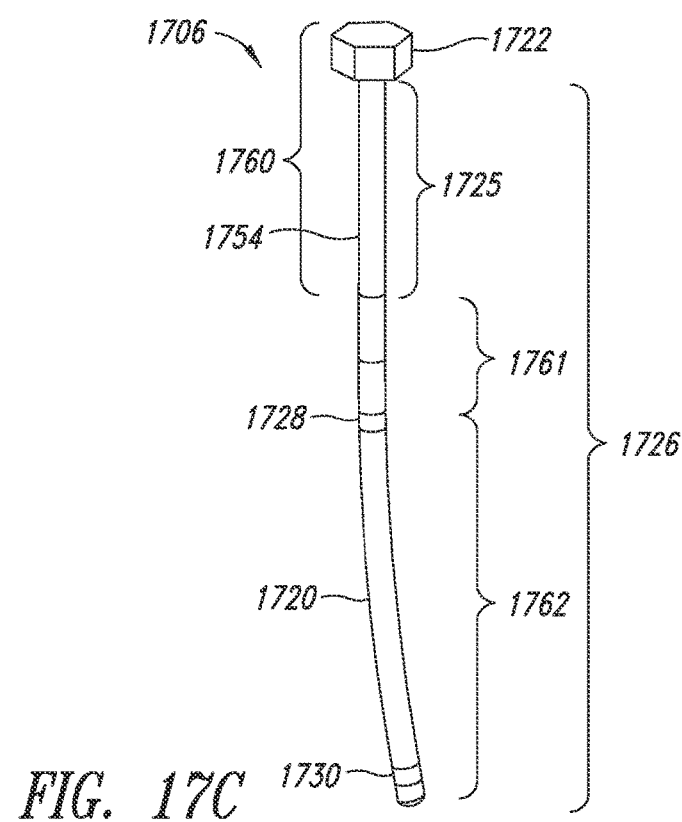

With reference to FIGS. 17A-17C, in some embodiments a cartridge configuration of a smart medical device 1700 includes a cannulated screw 1702 and an electronics cartridge 1706 configured for insertion into the cannulated screw such that a part of the electronics cartridge extends through and beyond the distal end of the cannulated screw. In some configurations, various electronics of the electronics cartridge 1706 are located in a head 1722 of the electronics cartridge and a power supply 1754 is located in a first portion 1725 of the shaft 1726 of the electronics cartridge beneath the head. This and other structure and characteristics of the cannulated screw 1702 and the electronics cartridge 1706 are similar those described above for the cannulated screw 102 and an electronics cartridge 106 of the embodiment of FIGS. 1A-1C. Accordingly, such details are not repeated here. Instead further description of the smart medical device 1700 of FIGS. 17A-17D focuses on its distinct features.

With reference to FIG. 17C, the electronics cartridge 1706 includes a rigid proximal portion 1760, a rigid middle portion 1761, and a non-load bearing, flexible distal portion 1762. The proximal portion 1760 includes the head 1722 and the first portion 1725 of the shaft 1726 where the power supply 1754 is located. In some embodiments, the different portions 1760, 1761, 1762 of the electronics cartridge 1706 are made of a same implantable grade material, with similar or varying hardness. For example, the proximal portion 1760 may be formed of a metallic material with hardness of RA 25 or polymer of Durometer of 95A or harder. The middle portion 1761 may be formed of the same material and with a hardness similar to the proximal portion 1760. The flexible distal portion 1762 may be formed of the same material as the proximal portion 1760 and the middle portion 1761 but with a hardness less than those regions to enable flexing of the distal region. In some embodiments, the different portions 1760, 1761, 1762 of the electronics cartridge 1706 are made of a dissimilar implantable grade materials, with similar or varying hardness. In some embodiments the flexible distal portion 1762 is formed of matrix polymer.

The proximal portion 1760, the middle portion 1761, and the flexible distal portion 1762 are joined together to form a contiguous shaft 1726. To this end, the first portion 1725 of the shaft 1726, and the middle portion 1761 of shaft, and the flexible distal portion 1762 of the shaft can be joined together by a method of Morse taper connection, single lock threaded mechanism, or a keyway and single thread lock developing an interconnected section with a specific axial load capability and maintain a flexible deflection from the center axis of 1 degree of more. The flexible distal portion 1762 of the shaft includes a pair of electrodes 1728, 1730. The distance between the electrodes may be at least 1 mm. The electrodes 1728, 1730 are generally flush with the outer surface of the shaft 1726 of the electronics cartridge 1706. In one configuration, the electrodes 1728, 1730 are ring electrodes.

With reference to FIG. 17B, in this embodiment the cannulated screw 1702 has a length substantially less than the length of the electronics cartridge 1706 and functions to secure the electronics cartridge in place. In some embodiments the cannulated screw 1702 includes a shaft 1718 with a length substantially equal to the length of the first portion 1725 of the shaft 1726 of the electronics cartridge 1706, such that the when the cartridge is inserted into the screw the middle portion 1761 and the flexible distal portion 1762 of the shaft 1726 extend through the end of the screw. In some embodiments an electrically insulative coating is applied to the outer surface 1716 of the cannulated screw 1702. In some embodiments no electrically insulative coating is applied to the cannulated screw 1702 over the entire length.

With reference to FIGS. 17A-17C, during implant of the medical device 1700 for treatment of a bone fracture 1742, a portal hole sized to receive the electronics cartridge 1706 is formed across the bone fracture. The depth of the portal hole is such that upon later insertion of the electronics cartridge 1706 into and through the cannulated screw 1702, the bone fracture 1742 is located between the electrodes 1728, 1730, and preferably, midway between the electrodes. During implant, the cannulated screw 1702 is implanted into the portal hole, after which the electronics cartridge 1706 is inserted into and partially through the screw. To this end, the electronics cartridge 1706 may include a closed-end lumen for receiving a stylet to push the middle portion 1761 and the flexible distal portion 1762 beyond the cannulated screw 1702 and further into the portal hole. When the electronics cartridge 1706 is inserted into and through the cannulated screw 1702, the electrodes 1728, 1730 are on opposite sides of the bone fracture 1742.

The cannulated screw 1702 and the electronics cartridge 1706 may include one or more mechanisms similar to those described above with reference to FIGS. 2A-5B that secure the cartridge within the screw. Furthermore, a region 1720 of the flexible distal portion 1762 of the electronics cartridge 1706 can be configured to swell or expand upon exposure to fluid. To this end, the flexible distal portion 1762 may be made from a matrix polymer that swells with exposure to a flush of sterile water or saline after being implanted. The radial expansion and/or axial expansion of the region 1720 of the flexible distal portion 1762 serves to the secure the electronics cartridge 1706 in place and to cause intimate contact between the electrodes 1728, 1730 and boney tissue interface.

The electrodes 1728, 1730, in combination with other electronics of the medical device 1700, may define a sensor or sensor system configured to monitor electrical properties of tissue. In some embodiments, the sensor system is an impedance sensor that functions as an EIS sensor to detect the location of a bone fracture and monitor the healing status of such fractures. As describe further below, in this arrangement, the medical device 1700 enables the collection of data through these electrodes for purposes of bone fracture characterization and healing state analysis. The electrodes 1728, 1730, in combination with other electronics of the medical device 1700, may define a tissue conductive communications interface. Details of the tissue conductive communication interface are disclosed further below.

Method of Implant of Cartridge Configuration

A method of implanting a medical device like the one shown in FIGS. 1A and 1B includes implanting a structure 102 at least partially in a body, and after implanting the structure, inserting an electronics cartridge 106 into the lumen 104. The method further includes securing the electronics cartridge 106 to the structure 102. Later, after securing the electronics cartridge 106 to the structure 102, the cartridge may be removed from the lumen 104 without affecting the structural integrity of the structure or the cartridge. During implanting of the structure 102 in a body, a support element may be inserted into the lumen 104 to provide physical support along the length of the shaft of the structure 102. After the structure 102 is secure in the body, the support element is removed and the cartridge is inserted into the lumen 104.

With reference to FIGS. 18A-18G, further details of method of implanting a medical device like the one shown in FIGS. 1A and 1B relative to a fractured bone are provided. The method includes a two stage insertion process during which one or more cannulated screws is implanted into boney tissue, and an electronics cartridge is inserted into at least one of the cannulated screws.

Figure 18A:
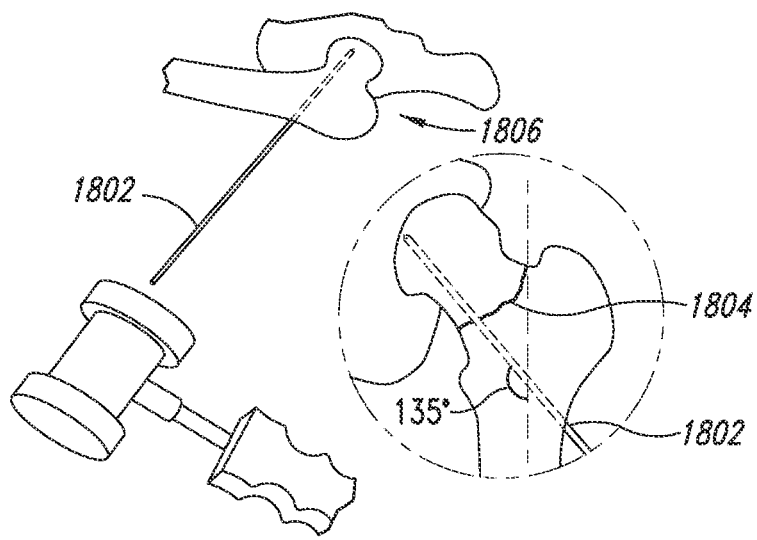
Figure 18B:
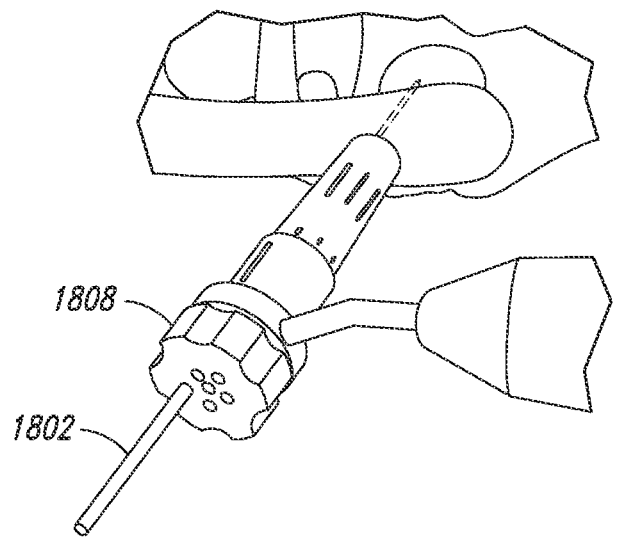
Figure 18C:
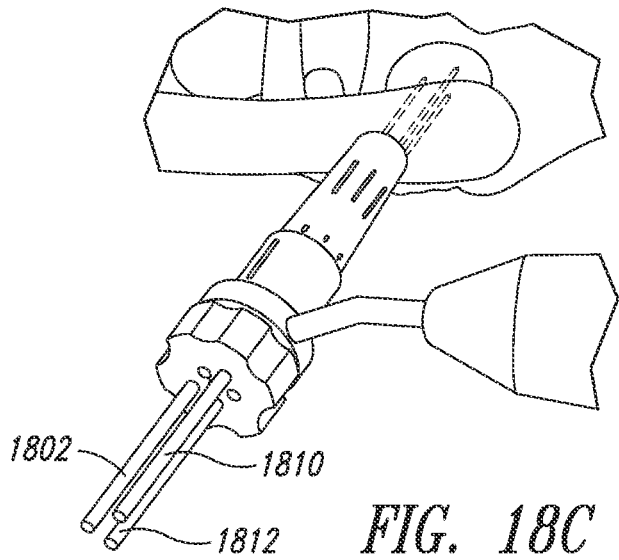
Figure 18D:
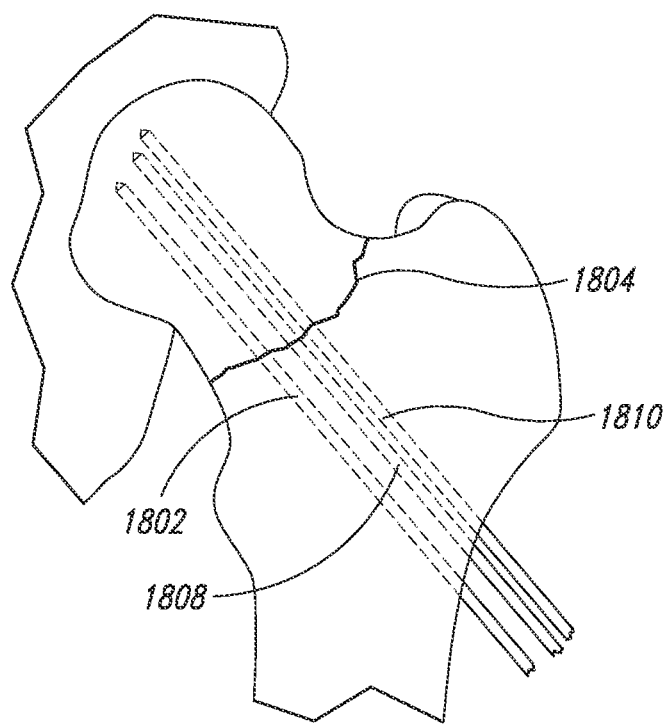

With reference to FIG. 18A, a first guidewire 1802 is driven across the bone fracture 1804 of the bone 1806 to within a distance, e.g., 5 mm of the subchondral bone, which is the outer area of the bone that encases the bone marrow, i.e., the outer surface of the bone. The first guidewire 1802 has an outer diameter less than the inner diameter of the cannulated screws to be implanted. With reference to FIG. 18B, a parallel drill guide 1808 is engaged with the first guidewire 1802 for purposes of creating parallel guidewire paths or portal holes. With reference to FIGS. 18C and 18D, three portal holes are drilled into the bone 1806 using the parallel drill guide 1808. A second guidewire 1810 and a third guidewire 1812 are inserted into the portal holes, and the drill guide is removed.

Figure 18E:
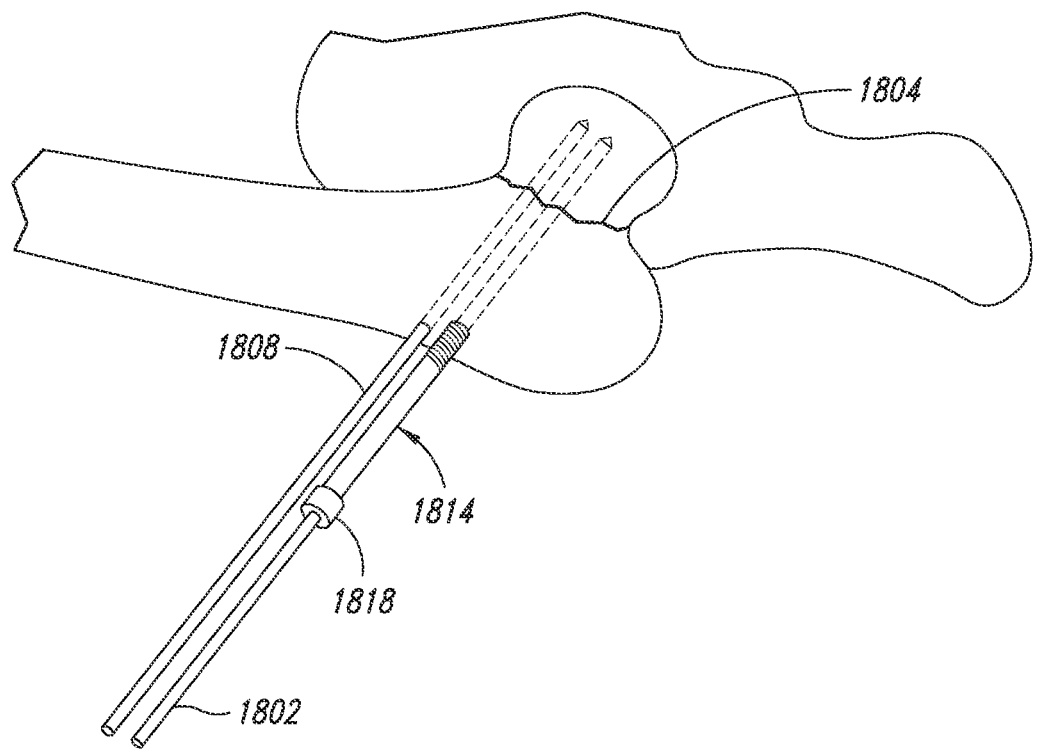

With reference to FIG. 18E, the length of the cannulated screw 1814 to be implanted in each portal hole may be measured using a depth gauge (not shown). If the head 1818 of a cannulated screw 1814 is to be countersunk, the head is included in the measure. Each of the cannulated screws 1814 is placed over a respective guidewire 1802, 1810, 1812 and slide over the guidewire until the tip of the screw is abutting the opening end of its respective portal hole.

With reference to FIG. 18F, a cannulated screw 1814 is screwed into each of the portal holes using an insertion tool 1822. The tool includes a drill bit 1824 configured to engage the head 1818 of the cannulated screw 1814, and has a lumen 1826 (shown in FIG. 18G) size to receive and slide over a guidewire 1802, 1810, 1812.

With reference to FIG. 18G, in some embodiments the drill bit 1824 may have a hexagonal cross-section sized to fit into a corresponding hexagonal socket of the head 1818. In this embodiment, the drill bit 1824 is place over a guidewire 1802, 1810, 1812 and slid toward the head 1818 of the cannulated screw 1814 and into engagement with the head. The drill bit 1824 is then rotated to advance the cannulated screw 1814 through the portal hole and across the bone fracture 1804. The drill bit 1824 is disengaged from the head 1818 of the cannulated screw 1814 and the guidewire 1802, 1810, 1812 is then removed, leaving the cannulated screw in place.

With reference to FIG. 18H, in some embodiments the drill bit 1824 may have a hexagonal cross-section sized to fit into a corresponding hexagonal socket of the head 1818 and a support shaft 1828 extending from the drill bit, and configured to fit in the lumen of the cannulated screw 1814. The support shaft 1828 may include a feature 1830, e.g., a linear projection along all or a portion of the shaft, configured to engage a corresponding feature, e.g., a linear slot or groove along at least a portion of the inner sidewall of the shaft 1834 of the cannulated screw 1814. Each of the drill bit 1824 and the support shaft 1828 also includes a lumen 1832 sized to receive and slide over a guidewire 1802, 1810, 1812.

In this embodiment, the support shaft 1828 and drill bit 1824 is place over a guidewire 1802, 1810, 1812 and slid toward the head 1818 of the cannulated screw 1814. The support shaft 1828 is positioned relative to the cannulated screw 1814 to align the projection 1830 of the support shaft with the slot of the shaft 1834 of the cannulated screw. The support shaft 1828 is slid into the lumen of the cannulated screw 1814 until the drill bit 1824 engages the head 1818 of the screw. The drill bit 1824, together with the support shaft 1828 are rotated to advance the cannulated screw 1814 through the hole and across the bone fracture 1804. The drill bit 1824 and support shaft 1828 are disengaged from the cannulated screw 1814 and the guidewire 1802, 1810, 1812 is then removed, leaving the cannulated screw in place. The support shaft 1828 provides support along the length of the shaft 1834 of the cannulated screw 1814 during insertion and functions to distribute the application of torque during rotation to both the head 1818 region of the screw and the shaft 1834 of the screw. Distribution of torque in this manner reduces the possibility of breakage of the cannulated screw 1814 during implant.

In alternate configurations, the support shaft 1828 may be smooth along its length and not include a feature, e.g., linear projection or key. This configuration supports the shaft 1834 of the cannulated screw during implant but does not function to transfer torque. In another alternate configuration, the support shaft 1828 may be a separate component that is inserted into the lumen of the cannulated screw 1814 prior to engagement of the drill bit 1824. In this configuration, the support shaft 1828 may include a feature, e.g., linear projection or key, that engages a corresponding feature, e.g., groove or channel, of the shaft 1834 of the cannulated screw 1814. In this case, the drill bit 1824 includes a feature, e.g., hex socket, configured to engage a hex end of the support shaft 1828 for purposes of torque transfer along the support shaft during rotation of the drill bit.

Figure 18I:
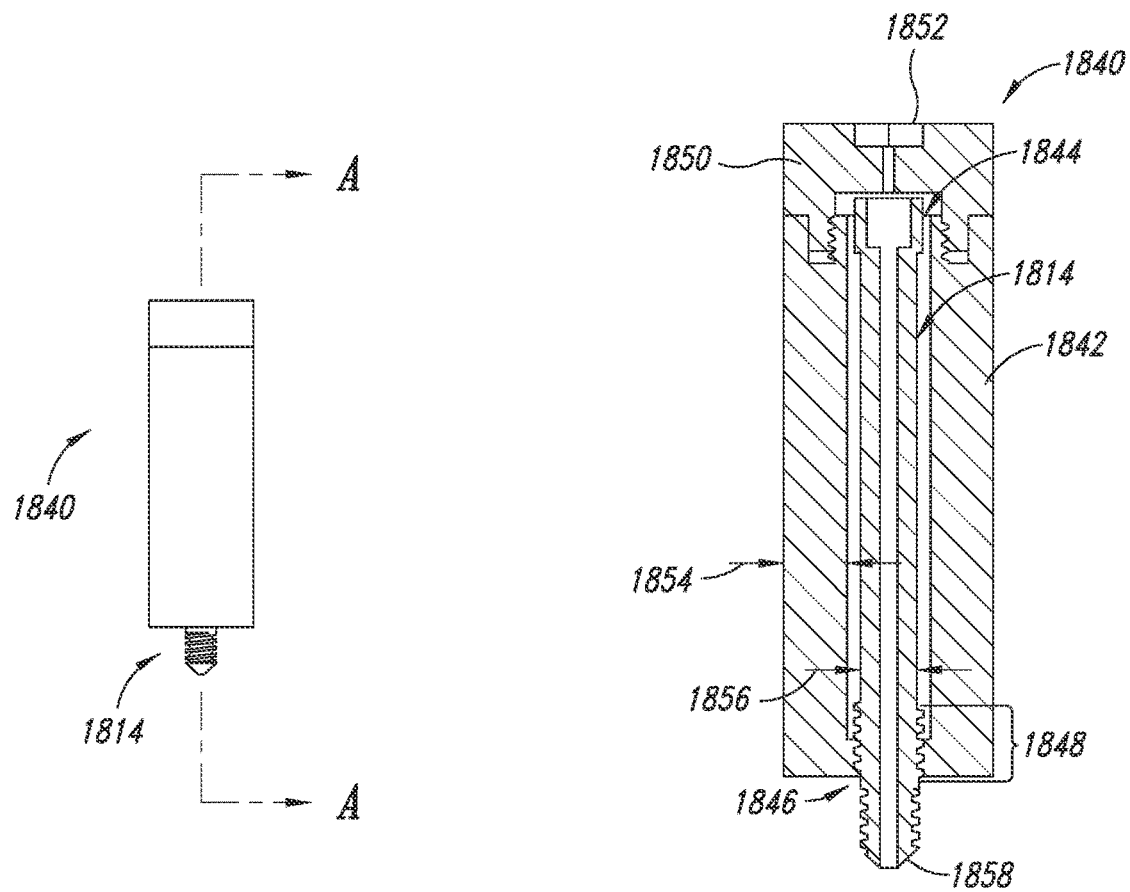

With reference to FIG. 18I, in some embodiments a cannulated screw 1814 may be configured to be placed within a coupling device 1840 as part of the implant procedure. The coupling device 1840 includes an annular body 1842 having a proximal end region with a proximal opening 1844 sized to receive the cannulated screw 1814, and a distal end region with a distal opening 1846 configured to receive and engage a distal portion 1848 of the cannulated screw 1814. The engagement may be through thread features on the outer diameter of the distal portion 1848 of the cannulated screw, and thread features on an inner diameter of the annular body 1842. The engagement may also be through a lock mechanism. The coupling device 1840 may also include a cap 1850 configured to engage the proximal end of the annular body 1842. The engagement may be through respective thread features of the cap 1850 and the annular body 1842. The cap 1850 also includes a feature 1852, e.g., a hex socket, configured to engage a drill bit. During implant, the portal holes through the bone are of a size sufficient to receive the annular body 1842 of the coupling device 1840. In FIG. 18I, the size of the annular body 1842 relative to the size of the cannulated screw 1814 is not to scale for purposes of clarity in illustration. Generally, the thickness 1854 of the annular body 1842 is less than the diameter 1856 of the cannulated screw 1814, and may be, for example, one quarter to one half the diameter of the cannulated screw.

In this embodiment, a cannulated screw 1814 is secured within a coupling device 1840, e.g., the distal portion 1848 of the cannulated screw is threaded into the distal opening 1846 of the annular body 1842 and the cap 1850 is coupled to the proximal end of the annular body. The coupling device 1840 and cannulated screw 1814 are placed over a respective guidewire 1802, 1810, 1812 and slide over the guidewire until the tip 1858 of the screw is abutting the opening end of its respective hole. With additional reference to FIG. 18G, the drill bit 1824 may have a hexagonal cross-section sized to fit into a corresponding hexagonal socket of the cap 1850 of the coupling device 1840. The drill bit 1824 is place over the guidewire 1802, 1810, 1812 protruding from the cap 1850 of the coupling device 1840 and slid toward the cap and into engagement with the cap.

The drill bit 1824 is then rotated to advance the coupling device 1840 and the cannulated screw 1814 through the portal hole and across the bone fracture 1804. The drill bit 1824 is rotated in the opposite direction to disengage the coupling device 1840 from the cannulated screw 1814 and the coupling device is removed from the portal hole, leaving the cannulated screw in place. At this stage, the cannulated screw 1814 may be further rotated as needed through direct engagement with a drill bit to fully seat the screw. For example, the cannulated screw 1814 may be rotated to place the screw head in abutting contact with bone to force the portions of the fractured bone together. The guidewire 1802, 1810, 1812 is then removed from the cannulated screw 1814. During rotation of the coupling device 1840, energy transmission of the torque applied at the proximal end of the device is along the length of the annular body 1842 to the distal end of the annular body 1842 and to distal portion 1848 of the cannulated screw, where the annular body couples to the screw. In this way, torque transfer along the length of the shaft of the cannulated screw 1814 is avoided. Distribution of torque in this manner reduces the possibility of breakage of the cannulated screw 1814 during implant.

In an alternate implant procedure, the annular body 1842 may be used without the cap 1850 to implant the cannulated screw 1814. In this embodiment, the proximal end of the annular body 1842 is configured to engage a drill bit 1824.

Figure 18J:
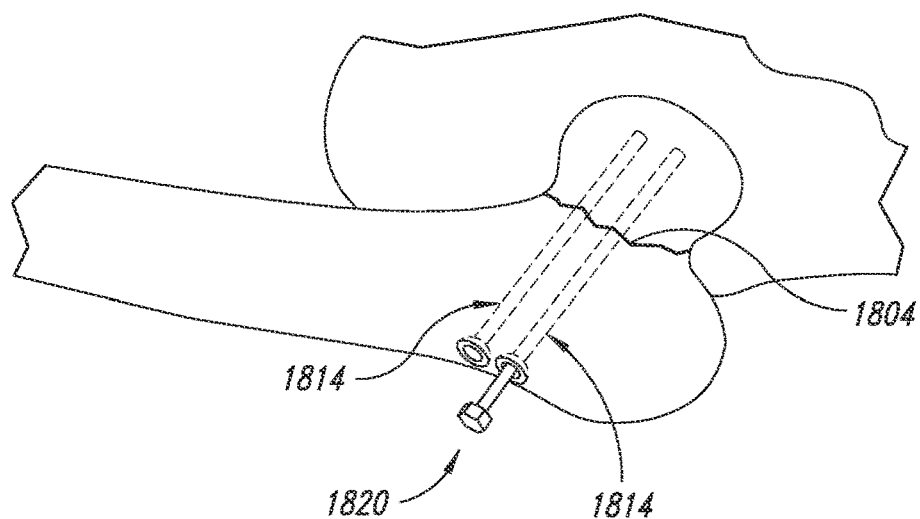
Figure 19A:
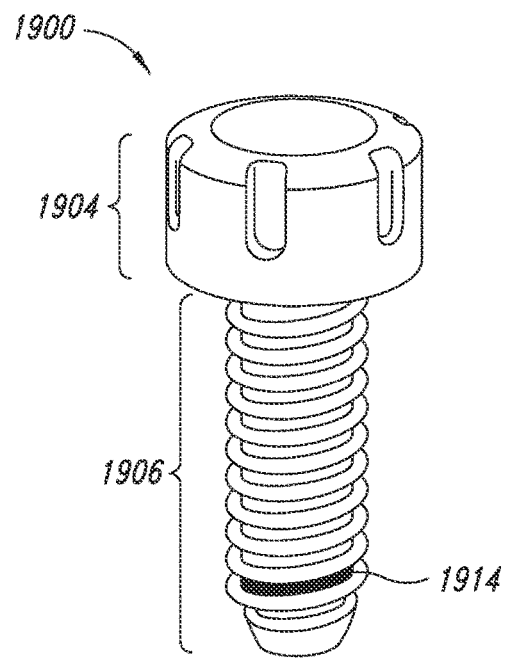
FIGS. 19A, 19B, 19C, and 19D are illustrations of a preloaded configuration of a smart medical device that includes a screw with an integrated electronics package.
Figure 19B:
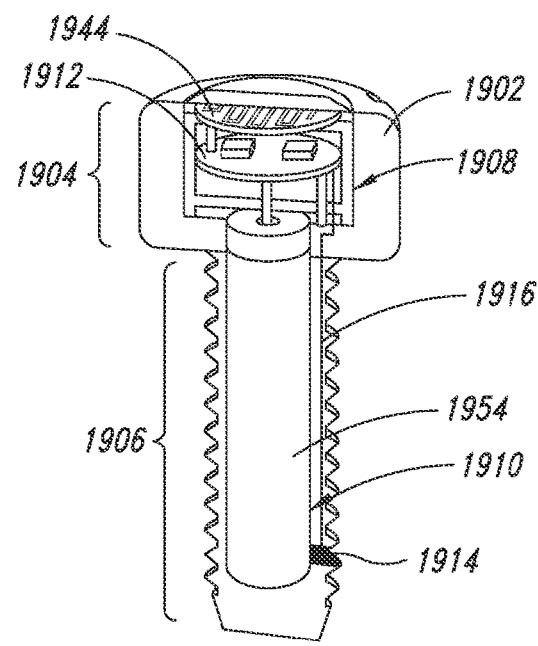
Figure 19C:
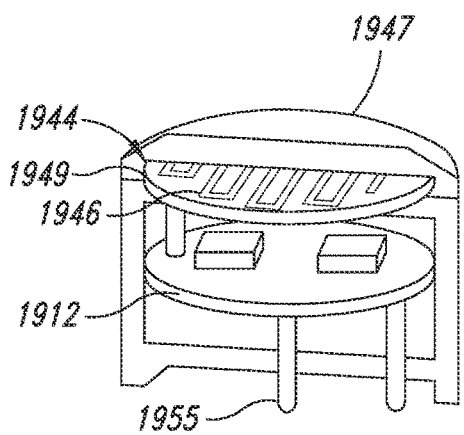
Figure 19D:
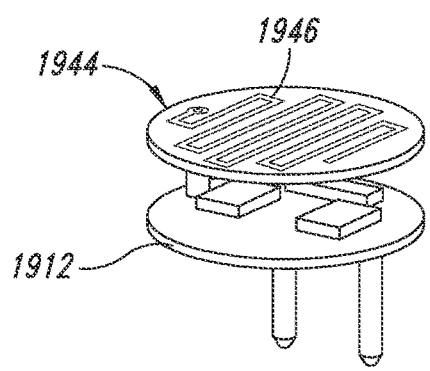

With reference to FIG. 18J, after the cannulated screws 1814 are implanted, an electronics cartridge 1820 is inserted into at least one of the cannulated screws. In some embodiments the electronics cartridge 1820 may be inserted into the screw in a two-step process. In a first action, an insertion tool similar to a syringe is used to inject and place electronics cartridge 1820 within the cannulated screw 1814. In a second action, the electronics cartridge 1820 is secured in place within the cannulated screw 1814 using at least one of the mechanisms described above with reference to FIGS. 2A-5B.

In some embodiments the electronics cartridge 1820 may be inserted into the screw using a guidance tool. The guidewire in the center of the cannulated screw 1814 is removed before the electronics cartridge 1820 can be installed. Before the guidewire is removed, a guidance tool is placed over the guidewire. The tip of the guidance tool has a tapered end that registers against the head of the cannulated screw 1814. Placed in this way, the guidance tool extends out of surgical site but does not extend past the end of the guidewire. With the guidance tool registered to the screw head, the guidewire is removed, and the electronics cartridge 1820 is fed down inside the guidance tool until it slides into the cannulated screw 1814.

Preloaded Configuration

With reference to FIGS. 19A-19D, in some embodiments a preloaded smart medical device 1900 includes a structure 1902 having a head 1904 and a shaft 1906, each respectively defining a head cavity 1908 and a shaft cavity 1910. In some embodiments, the medical device 1900 is a screw configured to be implanted in boney tissue. The medical device 1900 also includes an antenna 1944 and an electronics assembly 1912 located in the head cavity 1908, and a power supply 1954 located in the shaft cavity 1910. At least one electrode 1914 is associated with the shaft 1906 and is electrically coupled to the electronic assembly 1912 by a conductor 1916 through the sidewall of the shaft 1906. Regarding the antenna 1944, it may be a conductive wire 1946 or trace extending along an antenna board 1949 encapsulated in a material 1947, such as PEEK, ceramic, or a material that enables communication and connectivity, e.g. RF signal transmission or reception. Regarding the power supply 1954, it is coupled to the electronics assembly 1912 through a pair of battery contacts 1955.

A preloaded smart medical device may be structurally similar to anyone of the previously describe cartridge configurations, but for the electronics cartridge being permanently secured within the structure, e.g., cannulated screw, during manufacturing. For example, a preloaded smart medical device may be made by inserting an electronics cartridge into a cannulated screw and welding the head of the electronics cartridge within the head of the cannulated screw, or securing the head in place with a biocompatible adhesive, such as a silicone or urethane based adhesive, and then hermitically sealing the assembly at each of the distal end and proximal end. In these preloaded configuration, one of the head of the electronics cartridge and the head of the cannulated screw is configured to receive an implant tool. For example, the electronics cartridge may include a socket head that engages an implant tool, or the head of the cannulated screw may include features on its outer surface, such as shown in FIG. 4, that engages an implant tool.

Structural features of the preloaded configuration are generally the same as described for the cartridge configuration. Accordingly, a description of these features is not repeated here.

Figure 20A:
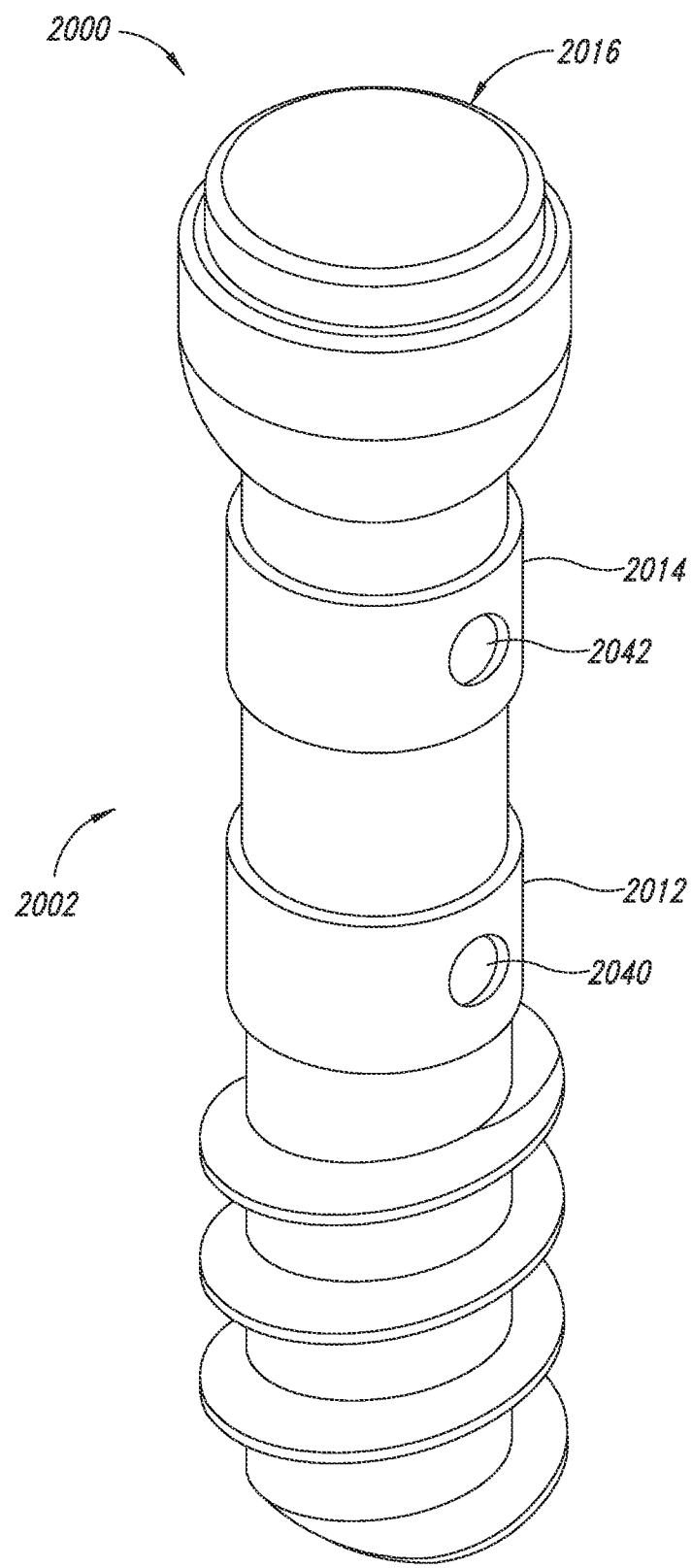
FIGS. 20A and 20B are illustrations of a preloaded configuration of a smart medical device that includes a cannulated screw having a pair of electrodes masked onto the surface of the screw that couple with an electronics package through vias in the sidewall of the screw.
Figure 20B:
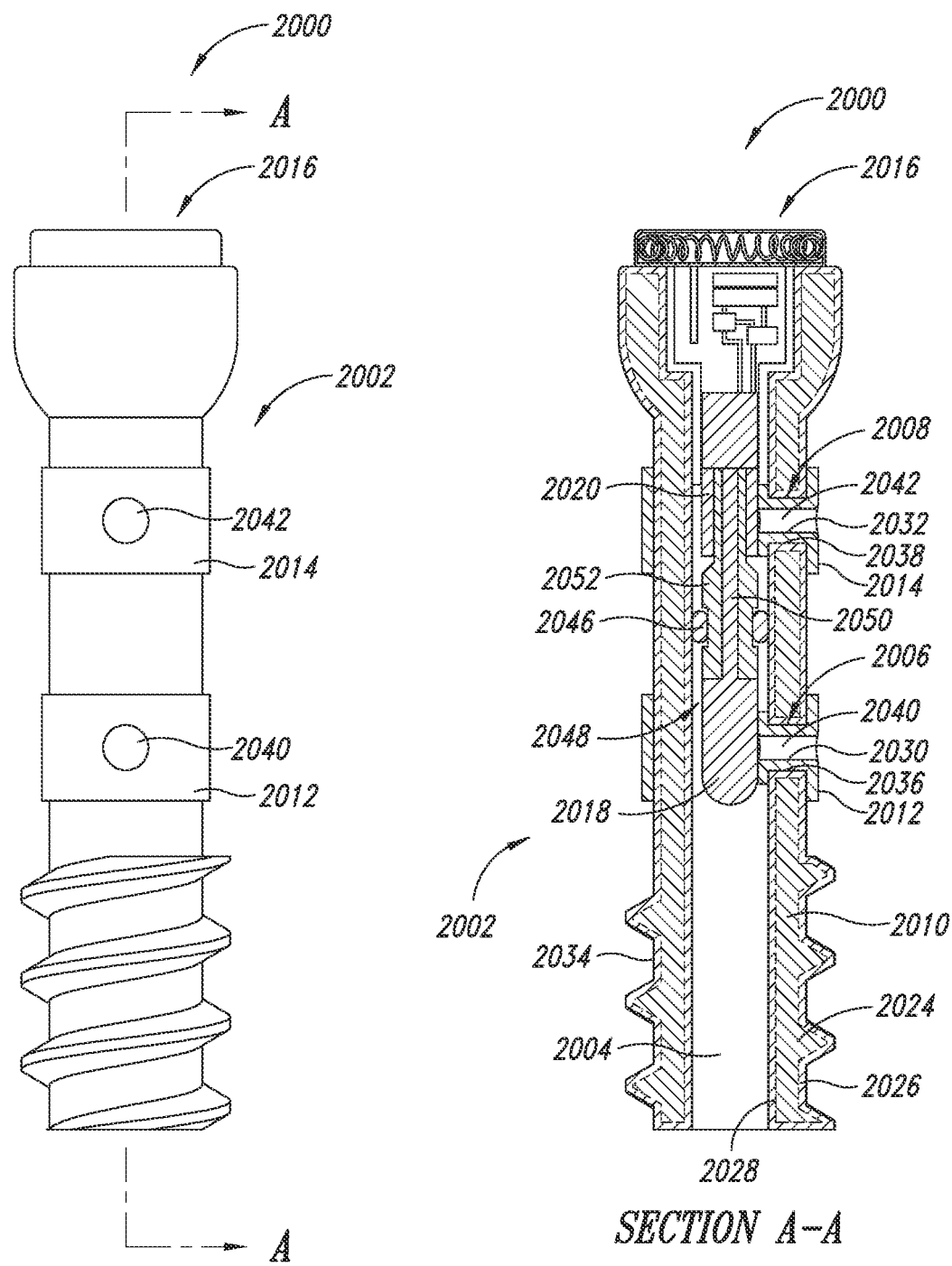

With reference to FIGS. 20A and 20B, in some embodiments a preloaded smart medical device 2000 includes a cannulated structure 2002 configured to be at least partially implanted in a body. The cannulated structure 2002 has a lumen 2004 extending therethrough, a plurality of apertures 2006, 2008 through a sidewall 2010, and a plurality of electrodes 2012, 2014 each associated with one of the plurality of apertures. The medical device 2000 also includes an electronics cartridge 2016 that is at least partially within the lumen 2004 of the cannulated structure 2002. The electronics cartridge 2016 includes electronics, e.g., an antenna, ASIC, power source, etc. The electronics cartridge 2016 also includes a plurality of electrical contacts 2018, 2020 each aligned with one of the apertures 2006, 2008 to establish an electrical coupling between the electronics of the cartridge and each of the electrodes 2012, 2014.

The cannulated structure 2002 includes a substrate 2024 having an outer surface 2026 and an inner surface 2028. A first electrode 2012 of the plurality of electrodes is located on the outer surface 2026 of the substrate and has a feedthrough 2030 that extends through a first aperture 2006 of the plurality of apertures to the inner surface 2028 of the substrate. A second electrode 2014 of the plurality of electrodes is also location on the outer surface 2026 of the substrate and has a feedthrough 2032 that extends through a second aperture 2008 of the plurality of apertures to the inner surface 2028 of the substrate.

In some embodiments, the substrate 2024 is formed of an electrically insulative material. In some embodiments the substrate 2024 is formed of an electrically conductive material that is coated with an electrically insulative material 2034. As shown in FIG. 20B, the substrate 2024 may be treated or coated so the outer surface 2026, the inner surface 2028 and the inner wall 2036, 2038 of each aperture 2006, 2008 are electrically insulated. For example, a titanium substrate 2024 may be anodized to make the surfaces electrically insulated.

The electrodes 2012, 2014 may be formed by coating or treating the outer surface 2026 of the substrate 2024 to make the exterior portion of the electrodes. The inner wall 2036, 2038 of the apertures 2006, 2008 and an adjacent part of the inner surface 2028 of the substrate 2024 are likewise coated or treated. The coating or treating may be done, for example, by electroplating or silk screening. After the electrodes 2012, 2014 are formed, for example by electroplating, the apertures 2040, 2042 through the electrodes may be filled with material to strengthen the sidewall 2010 of the cannulated structure 2002, or the electrode plating process may be controlled to produce an electrode without an aperture to strengthen the sidewall.

The electrodes 2012, 2014 may be a custom plated shape as shown in FIG. 20B or they may be the shaped end of a conductive pin through the sidewall 2010 of the cannulated structure 2002. Using these construction techniques, any number, size, and shape of electrodes could be added to the surface of the screw. The electrodes 2012, 2014 are separated by an insulating seal 2046. The insulating seal 2046 prevents detrimental electrical contact between the electrodes if the space between them fills with conductive fluid. The insulating seal 2046 may be an O-ring or a compliant over-molded silicone wiper.

With continued reference to FIGS. 20A and 20B, in one configuration, the electronics cartridge 2016 includes a connecting leg 2048 that extends down the lumen 2004 of the cannulated structure 2002. The connecting leg 2048 includes a conductive center peg 2050 having a distal end that forms a first electrical contact 2018, an insulating core 2052, and a conductive jacket that surrounds a portion of the insulating core to form a second electrical contact 2020. As such, the electronics cartridge 2016 includes a first electrical contact 2018 that is positioned to contact the feedthrough 2030 of the first electrode 2012 on the inner surface 2028 of the substrate to thereby establish an electrical coupling between the electronics and the first electrode, and a second electrical contact 2020 that is positioned to contact the feedthrough 2032 of the second electrode 2014 on the inner surface of the substrate to thereby establish an electrical coupling between the electronics and the second electrode.

Figure 21A:
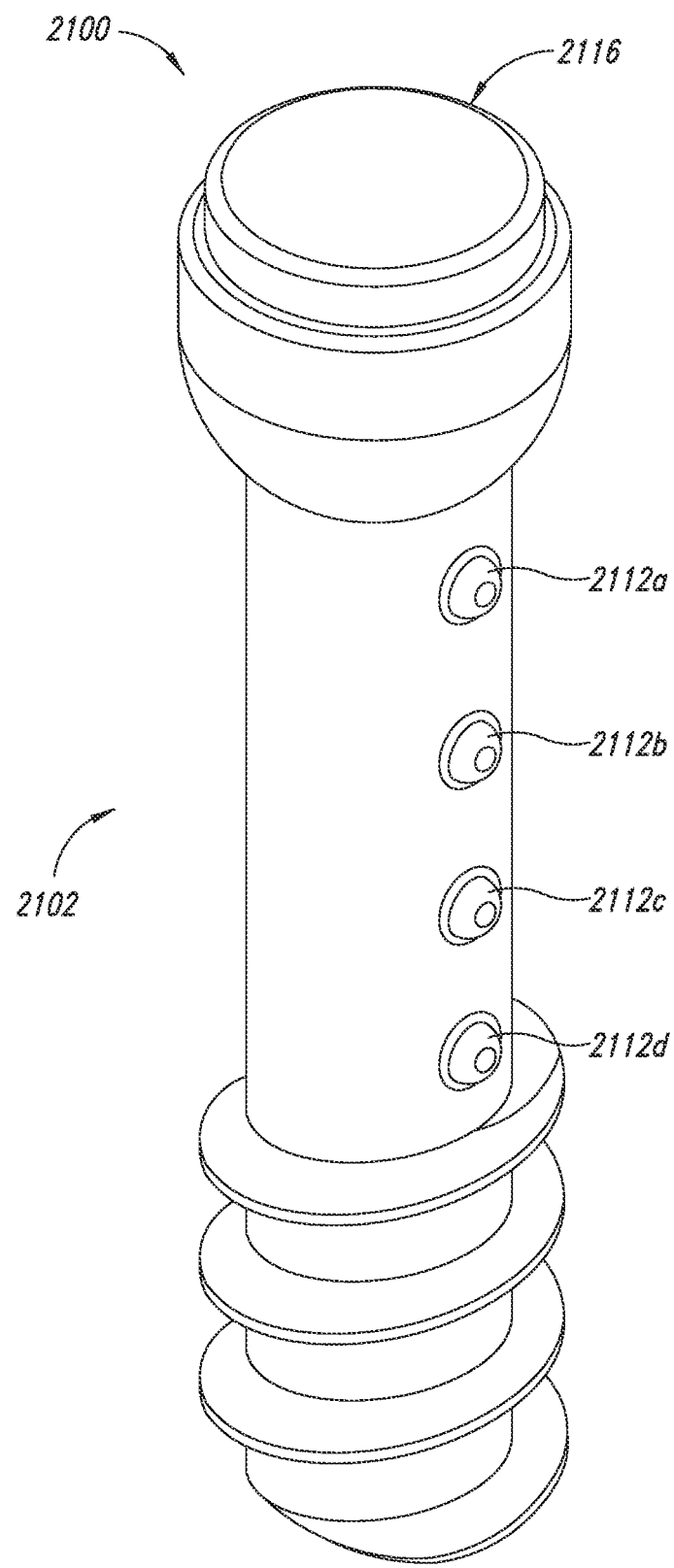
FIGS. 21A and 21B are illustrations of a preloaded configuration of a smart medical device that includes a cannulated screw having four pin electrodes that couple with an electronics package through vias in the sidewall of the screw.
Figure 21B:
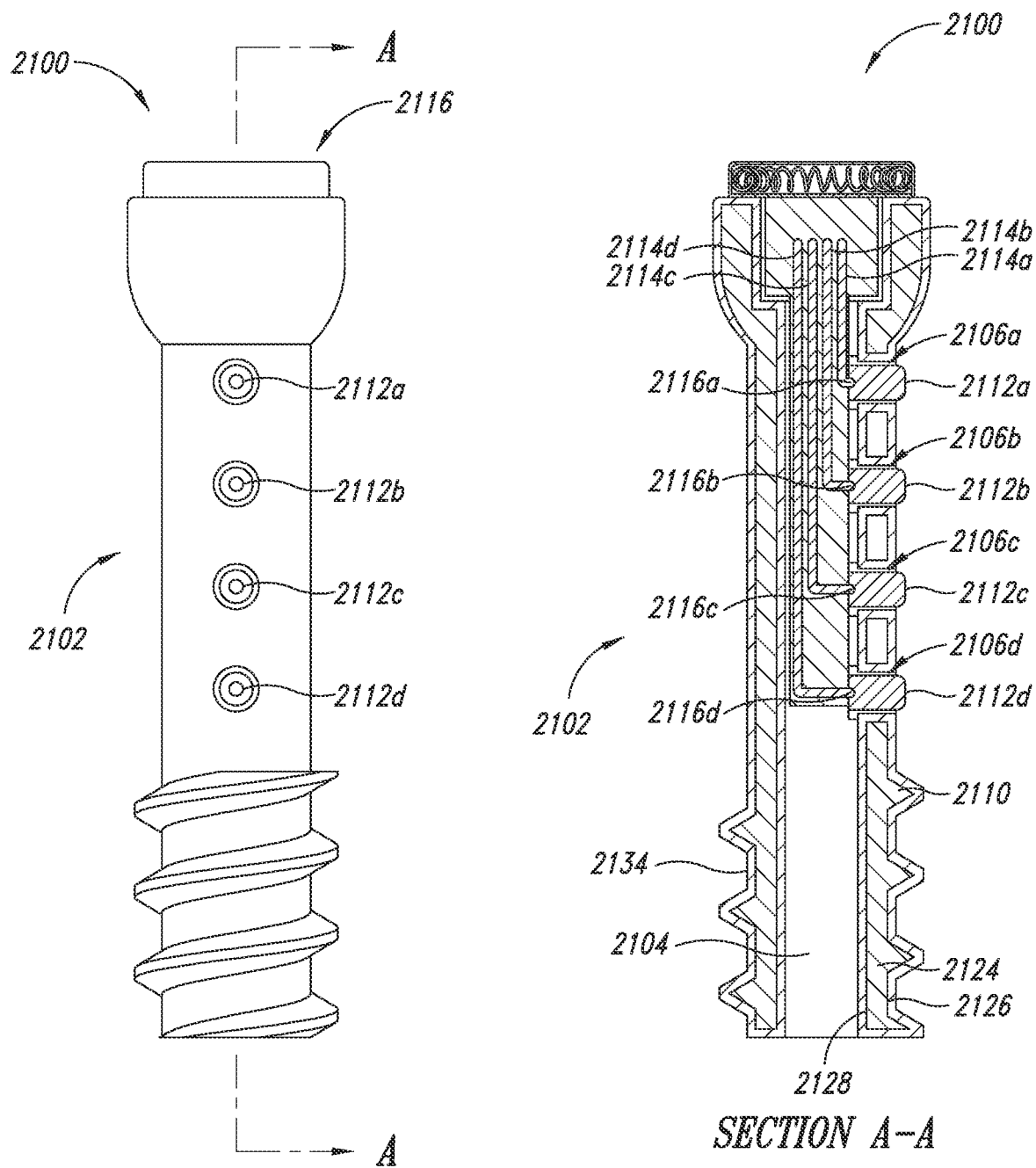

With reference to FIGS. 21A and 21B, in some embodiments a preloaded smart medical device 2100 includes a cannulated structure 2102 configured to be at least partially implanted in a body. The cannulated structure 2102 has a lumen 2104 extending therethrough, a plurality of apertures 2106a-2106d, through a sidewall 2110, and a plurality of pin electrodes 2112a-2112d each associated with one of the plurality of apertures. The medical device 2100 also includes an electronics cartridge 2116 that is at least partially within the lumen 2104 of the cannulated structure 2102. The electronics cartridge 2116 includes electronics, e.g., an antenna, ASIC, power source, etc. The electronics cartridge 2116 also includes a plurality of electrical traces 2114a-2114d each having a distal termination end 2116a-2116d that aligns with a respective one of the apertures 2106a-2106d to establish an electrical coupling between the electronics of the cartridge and each of the pin electrodes 2112a-2112d.

The cannulated structure 2102 includes a substrate 2124 having an outer surface 2126 and an inner surface 2128. In some embodiments, the substrate 2124 is formed of an electrically insulative material. In some embodiments the substrate 2124 is formed of an electrically conductive material that is coated with an electrically insulative material 2134. As shown in FIG. 21B, the substrate 2124 may be treated or coated so the outer surface 2126, the inner surface 2128, and the inner walls of each aperture 2106a-2106d are electrically insulated. For example, a titanium substrate 2124 may be anodized to make these surfaces electrically insulated.

The pin electrodes 2112a-2112d may be bonded or press fitted into the apertures 2106a-2106d and into contact with a corresponding one of the distal termination ends 2116a-2116d. The pins electrodes 2112a-2112d may be rigid or they may be spring loaded, pogo style pins biased to extend radially outward from the apertures 2106a-2106d. In configurations where the substrate 2124 of the cannulated structure 2102 is electrically conductive but not coated with an insulating material, the pin electrodes 2112a-2112d have an insulated outer surface and a conductive core. The pin electrodes 2112a-2112d could also be bonded into the apertures 2106a-2106d using an insulating bonding agent. The pin electrodes 2112a-2112d could be riveted into the apertures 2106a-2106d and the end of the pin could be flattened into an electrode in the riveting processes. The pin electrodes 2112a-2112d could be formed together by filling the apertures 2106a-2106d with conductive material that solidifies (e.g. conductive epoxy). This may help increase the strength of the sidewall 2110 of the cannulated structure 2102 in the region of the apertures 2106a-2106d.

Electrical Elements and Features

Having thus disclosed the mechanical, material, and other structural details of cartridge configuration and the preloaded configuration of smart medical devices, and their various embodiments, the electrical and operational elements and features of the two configurations are now described.

Figure 22A:
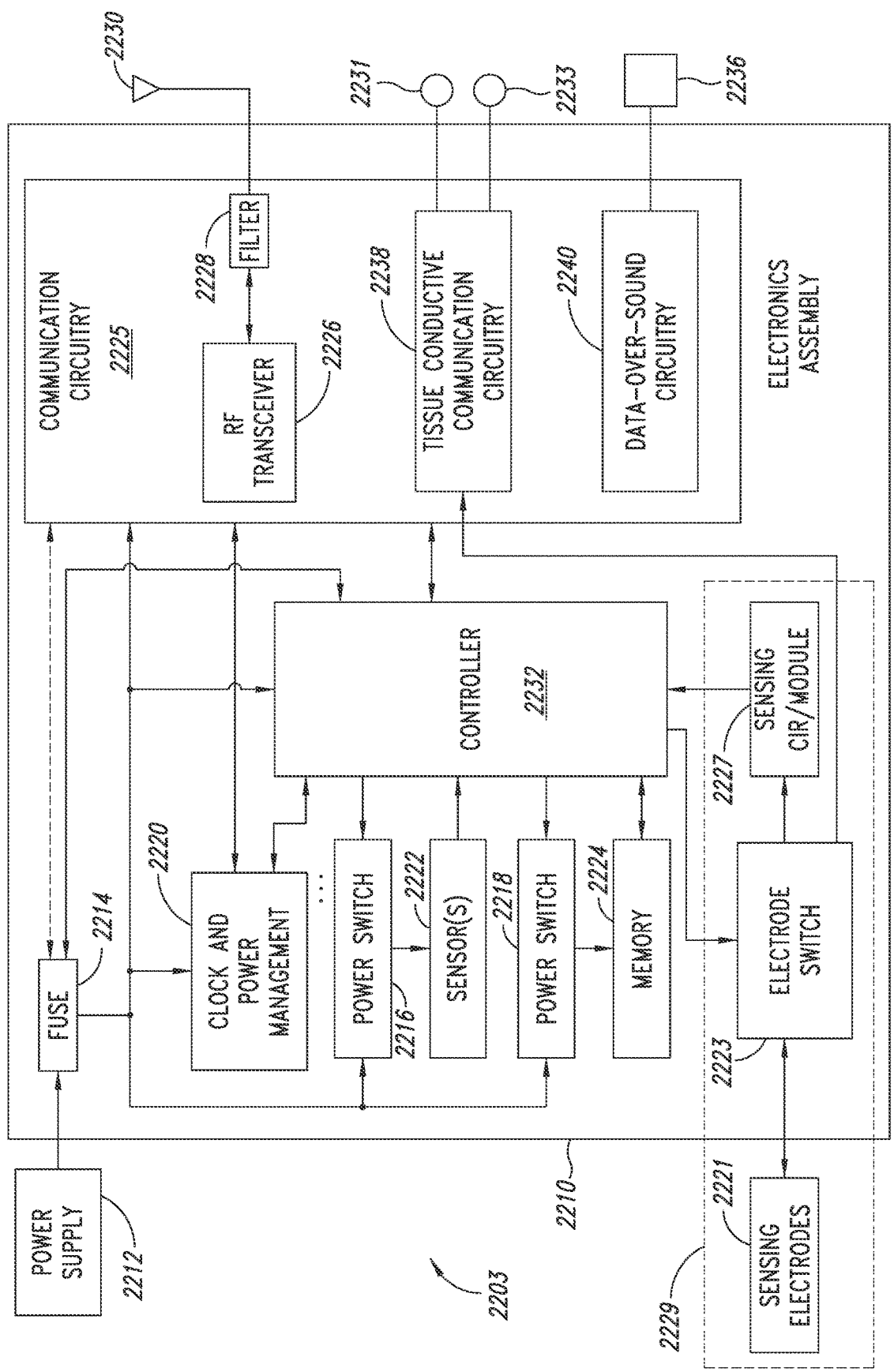
FIGS. 22A and 22B are block diagrams showing components of an exemplary implantable reporting processor (IRP) of a smart medical device that includes a sensor system for monitoring the healing state of a bone fracture.

With reference to FIG. 22A, configurations of the smart medical device include an implantable reporting processor (IRP) 2203. The IRP 2203 includes a power supply 2212, sensing electrodes 2221, an electronics assembly 2210, an antenna 2230, communication electrodes 2231, 2233, and an acoustic transducer 2236.

The circuitry of the electronics assembly 2210 may include one or more sensors 2222, an electrode switch 2223, and a sensing circuit/module 2227. As disclosed further below, in some embodiments, the sensing electrodes 2221, the electrode switch 2223, and the sensing circuit/module 2227 function together as a sensor 2229 configured to monitor an electrical property of tissue. For example, the sensor 2229 may be an impedance sensor.

The circuitry of the electronics assembly 2210 may include a fuse 2214, one or more power switches 2216, 2218, a clock generator and power management unit 2220, a memory 2224, a controller 2232, and communication circuitry 2225. The communication circuitry 2225 may include one or more of a radio frequency (RF) transceiver 2226 and a filter 2228, that couple with the antenna 2230; tissue conductive communication (TCC) circuitry 2238 that coupled with the set of communication electrodes 2231, 2233; or data-over-sound circuitry 2240 that couples with the acoustic transducer 2236. Examples of some or all of these components are described elsewhere in this application or in U.S. Ser. No. 16/084,544, which is incorporated by reference in all jurisdictions which allow incorporation by reference. In one embodiment, the electronics assembly 2210 may be an ASIC chip with capability of recharging through 2 mF-8 mF capacitors for processing and transmission of the data packages.

As noted above, the IRP 2203 includes one or more sensors 2222, 2229. "Sensor" refers to a device or a combination of components forming a sensor, that can be utilized to do one or more of: 1) detect, measure and/or monitor one or more aspects of body or body segment/joint condition or function (fracture healing, motion including measurement of the positions, angles, velocities, and accelerations of body segments and joints), 2) detect, measure and/or monitor one or more different aspects of a body tissue (anatomy, physiology, metabolism, and/or function), and/or 3) detect, measure and/or monitor one or more aspects of the orthopedic device or implant.

Figure 22B:
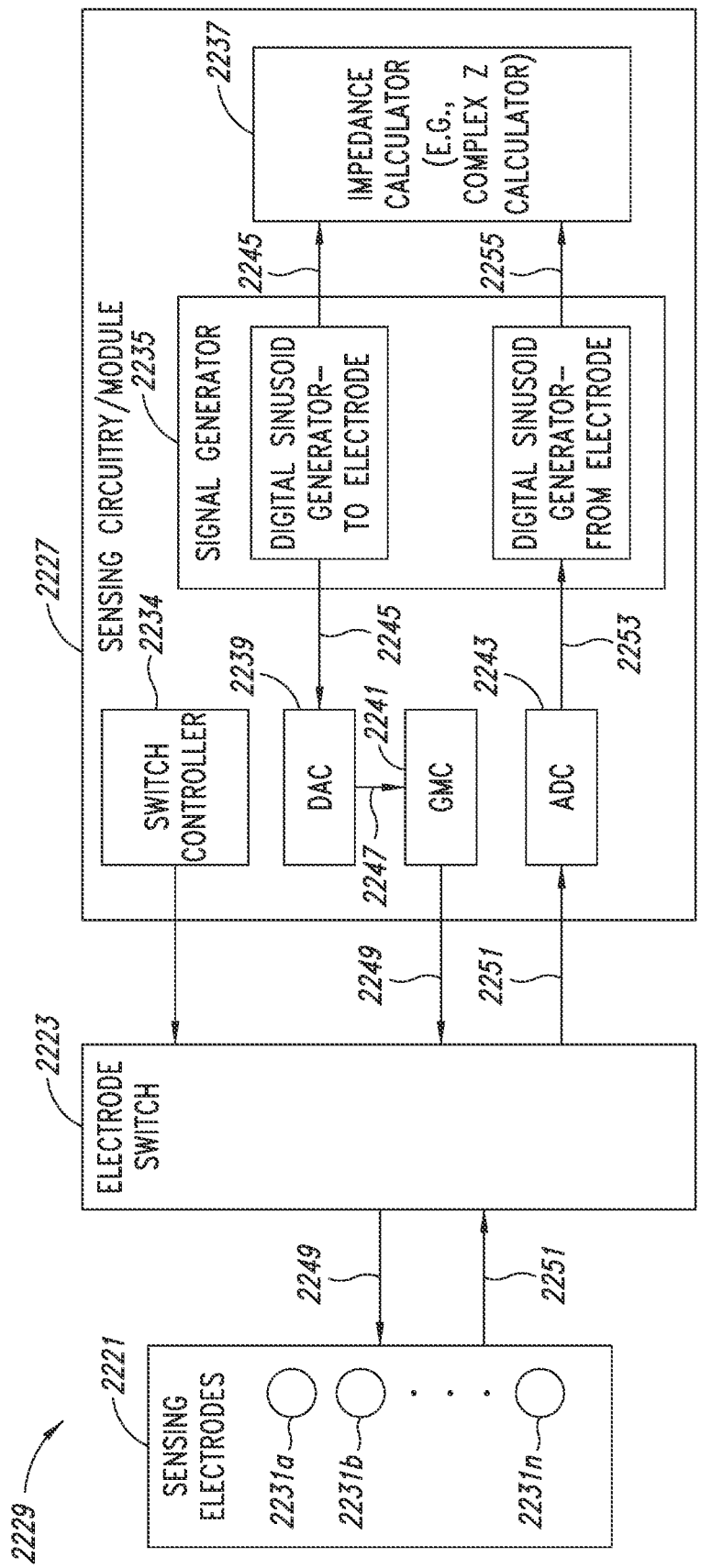

With reference to FIG. 22B, and as mentioned above, in some embodiments the IRP 2203 includes an impedance sensor 2229 comprising sensing electrodes 2221, an electrode switch 2223, and a sensing circuit/module 2227. The sensing electrodes 2221 may include a number of individual electrodes 2231a-2231n. In some embodiments, the number of electrodes 2231a-2231n is at least two and may be up to eight or possibly more. With reference to FIGS. 1A-1C, in some embodiments the sensing electrodes 2221 may correspond to the electrodes 128, 130 associated with a cannulated screw 102. With reference to FIGS. 13A-13D, in some embodiments the sensing electrodes 2221 may correspond to the electrodes 1328, 1330 associated with an electronics cartridge 1306. With reference to FIGS. 14A-14D, in some embodiments the sensing electrodes 2221 may correspond to an array of electrodes 1414 associated with an electronics cartridge 1406.

Returning to FIG. 22B, in some embodiments, the sensing circuit/module 2227 of the impedance sensor 2229 includes a switch controller 2234, a signal generator 2235, an impedance calculator 2237, a digital-to-analog converter (DAC) 2239, a transconductance amplifier (GMC) 2241, and an analog-to-digital converter (ADC) 2243. In this configuration, the impedance sensor 2229 functions as an EIS sensor that measures frequency-dependent impedances through body anatomy for purposes of characterizing a bone fracture and determining a healing state or condition of the bone fracture. EIS sensors within this context are described, for example, in New Opportunities for Fracture Healing Detection: Impedance Spectroscopy Measurements Correlate to Tissue Composition in Fractures, by Monica C. Lin et al., Journal of Orthopaedic Research, published December 2017, which is herein incorporated by reference.

With continued reference to FIG. 22B, a medical device may include a sensor system 2229, e.g., an impedance sensor or EIS sensor, that includes one or more sensing electrodes 2231a-2231n, and one or more components 2223, 2227 electrically coupled to the one or more sensing electrodes to monitor an electrical property of tissue for purposes of characterizing bone fracture healing. Two structural embodiments of such a medical device are contemplated, one in which the sensor components of the sensor system 2229 are included in a single medical device, and another in which the sensor components are located across a number of different structures of a medical device.

Figure 24A:
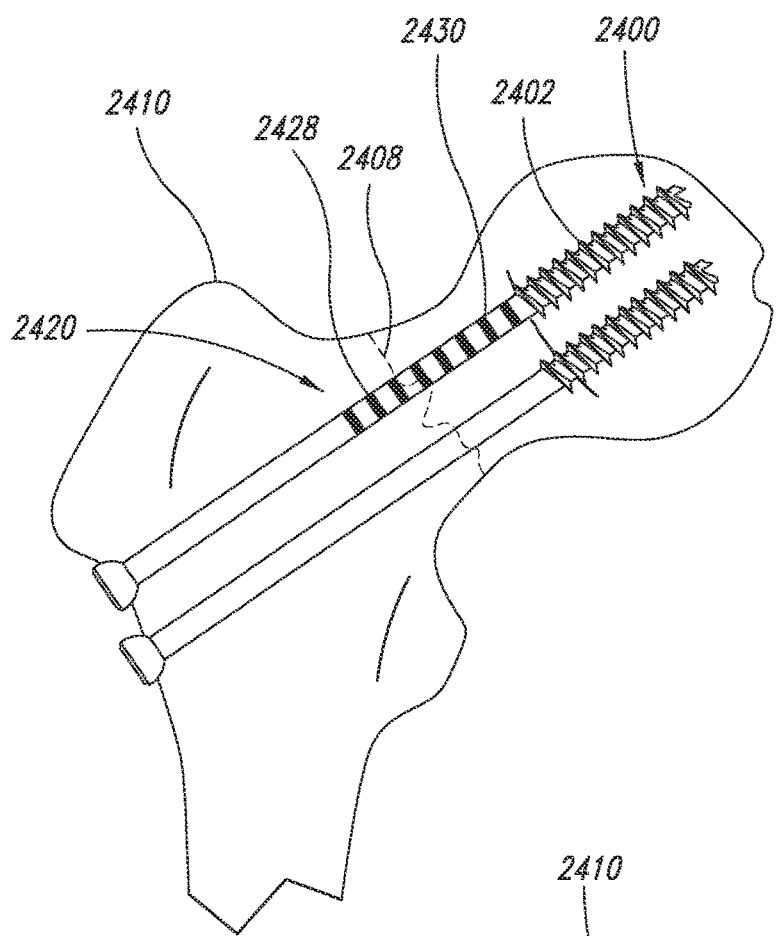
Figure 24B:
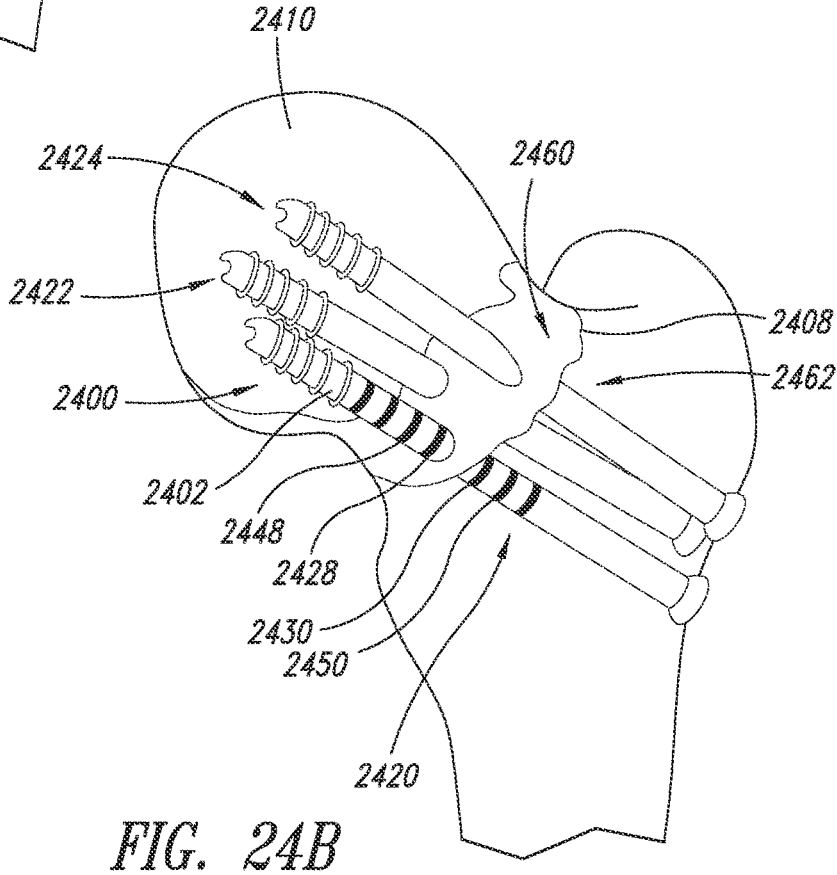

With reference to FIGS. 24A and 24B, in the first embodiment, a plurality of sensing electrodes 2420 are associated with a single medical device 2400 having a structure configured to be implanted in a bone 2410 to bridge a bone fracture 2408. In this embodiment, the length of the medical device 2400 is selected to enable the positioning of a first sensing electrode 2428 on a first side of the bone fracture 2408, and second sensing electrode 2430 on a second side of the bone fracture opposite the first side.

Figure 24C:
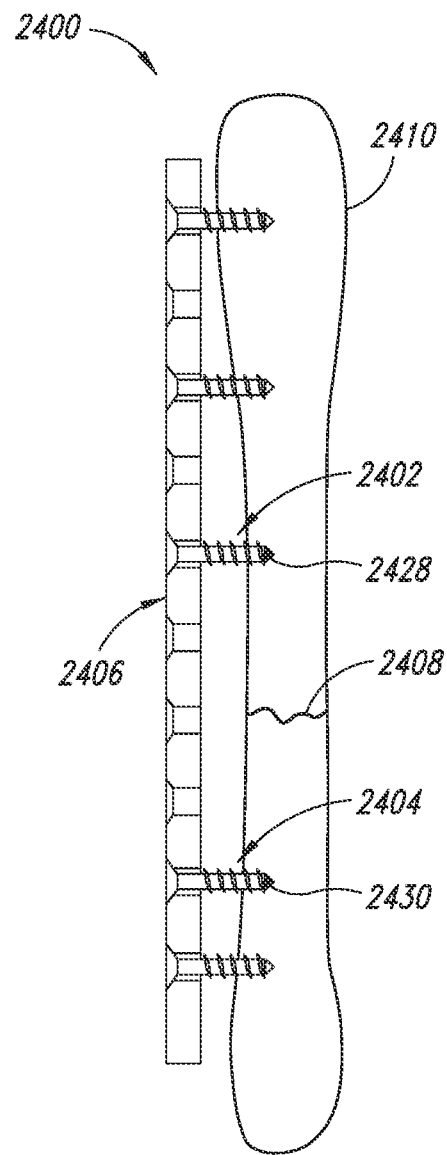

With reference to FIG. 24C, in the second embodiment, a first sensing electrode 2428 of a medical device 2400 is associated with a first implant or structure 2402 configured to be implanted on a first side of a bone fracture 2408, and a second sensing electrode 2430 of the medical device is associated with a second implant or structure 2404 configured to be implanted on a second side of the bone fracture. In this embodiment, the medical device 2400 includes a third implant or plate 2406 configured to span the structures 2402, 2404. The plate 2406 serves as a means of electrically coupling the two sensing electrodes 2428, 2430 to common sensing components. The common sensing components may be included in one or more of the first structure 2402, the second structure 2404, and the plate 2406.

In either embodiment, impedance measurements across a bone fracture 2408 of a bone may be obtained and analyzed overtime as a means of monitoring the healing process from the inflammatory phase, through the repairing phase, e.g., from hematoma to calluses, as it transitions to bony callus/spongy bone. To this end, changes in impedance measurements as a function of time may be obtained by the medical device 2400. The measurements may be obtained periodically, e.g., once an hour, once every 6 hours, etc., to collect a data set of impedance measurements overtime. In some embodiments the data set of impedance measurements is analyzed onboard by the medical device 2400 to provide an outcome that delineates the healing condition of the bone fracture. In some embodiments the data set is communicated to an external device for analysis to provide an outcome that delineates the healing condition of the bone fracture.

In either case, such delineations may include one of: "union" (meaning the fracture 2408 is healed, e.g., impedance magnitude across fracture has increased above a baseline by a threshold amount, e.g. percentile), "suspected non-union" (meaning healing is not progressing at a level corresponding to union, e.g., impedance magnitude across fracture is increasing relative to a baseline, but the amount of increase is too slight and the rate of increase is too slow as a function of time), or "non-union" (meaning healing is not occurring, e.g., impedance magnitude across fracture is staying the same over time).

In some embodiments the outcome of the analysis is obtained based on comparisons between measures derived from the patient's data set of impedance measurements and similar measures derived from a reference data set of impedance measurements across a patient population. For example, a measure of change in impedance over a period of time derived from the patient's data set may be compared to a measure of change in impedance over the same period of time derived from the reference data set to determine if the patient's measurement is within an acceptance range of the reference measurement. If the patient's measurement is determined to be outside of the acceptance range the smart medical device 2400 may issue an alert. For example, if the patient's measurement deviates from the reference measurement by a threshold criterion, e.g., is less than the reference measurement by a percentile, an alert may issue.

Figure 23:
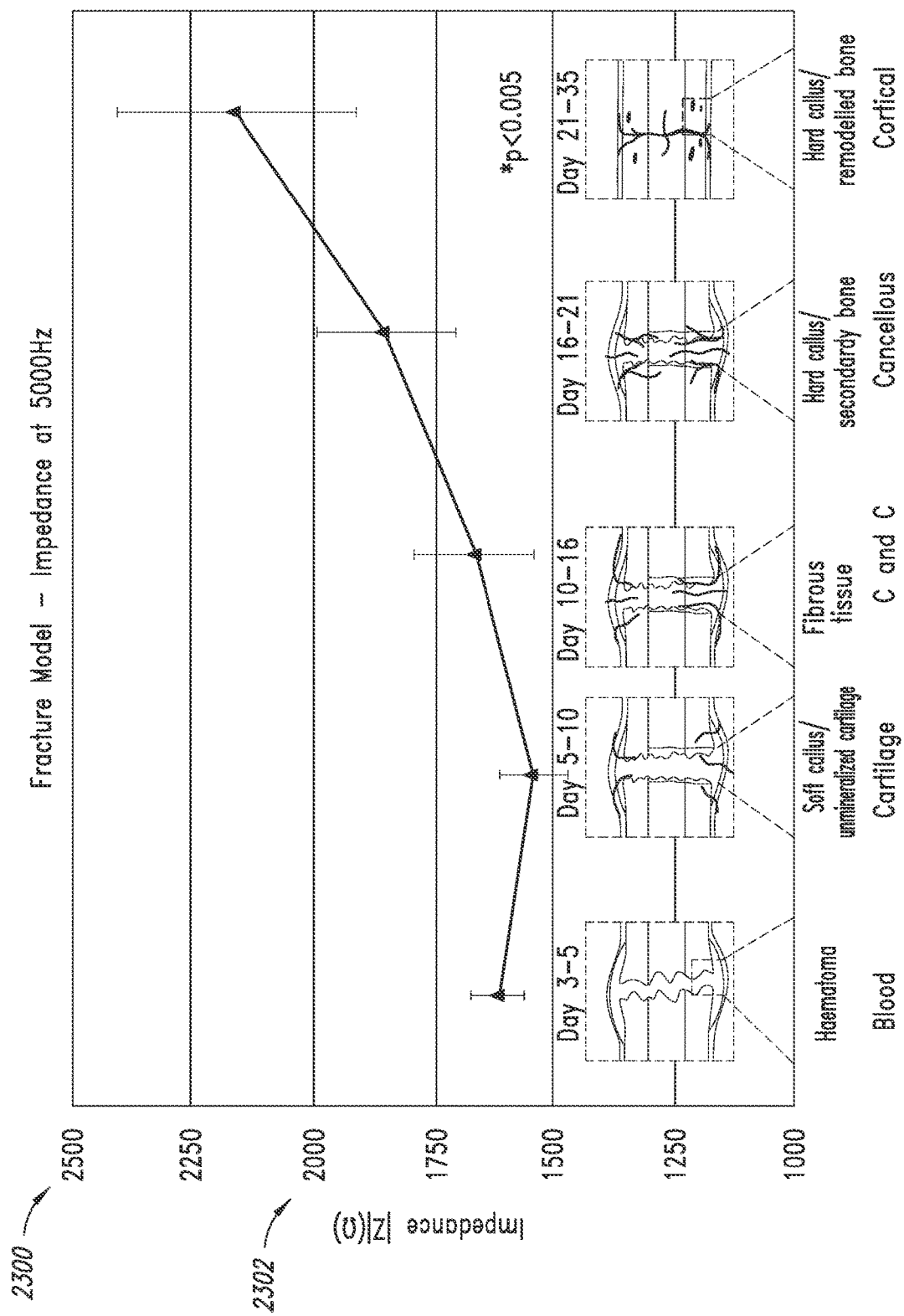
FIG. 23 is a graph of impedance magnitude measured across a bone fracture as a function of time using a smart medical device.

In some embodiments, measurements corresponding to different stages or modalities of bone healing over time may be established based on the reference data set. For example, with reference to FIG. 23, the reference data set may establish an expected change in impedance at day 7 after implant that is indicative of a "cartilage" healing state; an expected change in impedance at day 13 after implant that is indicative of a "C and C" healing state, where "C and C" stands for cartilage and cancellous; an expected change in impedance at day 19 after implant that is indicative of a "cancellous" healing state; and an expected change in impedance at day 28 after implant that is indicative of a "cortical" healing state. Patient measurements at similar times after implant may be compared to the reference measures to track the patients healing state and to issue an alert if a patient's measurement is outside an acceptance range of the corresponding reference measurement.

Regarding the obtaining of impedance measurements, with reference to FIG. 22B, as previously mentioned the impedance sensor 2229 may function as an EIS sensor. To this end, in some embodiments the impedance sensor 2229 employs a two-point impedance sensing method and the sensing electrodes 2221 include a first electrode and a second electrode. The first electrode and the second electrode may be selected from a plurality of available sensing electrodes 2231a-2231n. The sensing circuit/module 2227 is configured to enable the first electrode and the second electrode to function in either of an application mode or sensing mode. During the application mode a signal, e.g., a current, is applied across the first electrode and the second electrode. For example, a signal may be applied to the first electrode, while the second electrode is ground. During the sensing mode, the impedance between the first electrode and the second electrode is sensed based on a change in potential between the electrodes.

Regarding the application mode, in some embodiments, the signal generator 2235 generates a digital representation 2245 of a sinusoid in time at a first frequency and provides that sinusoid signal to both the DAC 2239 and the impedance calculator 2237. The DAC 2239 receives the digital representation 2245, converts it to an analog sinusoid voltage 2247, and provides it to the GMC 2241. The GMC 2241 converts the analog sinusoid voltage 2247 to a sinusoid current 2249. The GMC 2241 outputs the sinusoid current 2249 to the electrode switch 2223, which in turn, applies the sinusoid current to a first electrode 2231a-2231n of the sensing electrodes 2221. The sinusoid current 2249 is applied to body tissue by a voltage potential different between the first electrode and a second electrode 2231a-2231n of the sensing electrodes 2221 that is ground.

During the sensing mode, voltages 2251 across the first electrode and the second electrode and through the body tissue are sensed by the ADC 2243, which has an input coupled to the first electrode through the electrode switch

2223. The ADC 2243 converts the voltages 2251 to digital voltages 2253 and provides the voltages to the signal generator 2235. The signal generator converts the digital voltages 2253 to a digital sinusoid voltage 2255, and provides it to the impedance calculator 2237. The impedance calculator 2237 calculates an impedance based on the digital representation 2245 of a sinusoid in time at a first frequency and the resulting digital sinusoid voltage 2255.

The forgoing may be repeated for different frequencies in a range of frequencies. Different impedance measurements at different frequencies enables the collection of different measurements that may represent different bone fracture healing responses. Analysis of the measurements at different frequencies may reveal that impedance evolution at a specific frequency or a sub-set of frequencies correlate best with healing stage. For each frequency, the impedance calculator 2237 processes the corresponding digital representation 2245 of a sinusoid in time and the digital sinusoid voltage 2255 to calculate complex impedance (Z) of anatomy. As described above, these impedances are collected over time into a data set and analyzed to provide an outcome corresponding to the healing state of a bone fracture.

Regarding the obtaining of impedance measurements, and with continued reference to FIG. 22B, in some embodiments the impedance sensor 2229 employs a four-point impedance sensing method and the sensing electrodes 2221 include a first electrode, a second electrode, a third electrode, and a fourth electrode that are switchably coupled to the sensing module through the electrode switch 2223. The first electrode and the second electrode may be selected from a plurality of available sensing electrodes 2231a-2231n. The sensing circuit/module 2227 is configured to enable the first electrode and the second electrode to function in an application mode and the third electrode and the fourth electrode to function in a sensing mode. During the application mode a signal, e.g., a current, is applied across the first electrode and the second electrode. For example, a signal may be applied to the first electrode, while the second electrode is ground. During the sensing mode, the impedance between the third electrode and the fourth electrode is sensed based on the potential between the third electrode and the fourth electrode.

In some embodiments, changes in impedance are indicative of healing progression. For example, with reference to FIG. 23, a graph 2300 of impedance magnitude 2302 measured across a bone fracture as a function of time 2304 using a pair of sensing electrodes spaced 27 mm apart based on EIS measurements at a frequency of 5000 Hz is shown. A progression through different bone fracture characterizations or healing states, including cartilage, cartilage and cancellous (C and C), cancellous, and cortical, is indicated by a corresponding increase in impedance magnitude between days 5 and 35. In this example, given the increases in impedance magnitude over time, the data analysis outcome at day 35 would indicate "union" (meaning the fracture is healed).

The impedance sensor 2229 of the smart medical device 2400 provides various benefits over other methods of monitoring bone healing. For example, the monitoring capability of the medical device 2400 obviates the need for intermediate x-ray imaging, which reduces medical care costs and patient inconvenience of having to go to an imaging facility. In cases of suspected non-union, the monitoring capability of the medical device 2400 identifies slow healing earlier than image monitoring and allows for additional patient care and supplementary and/or alternative treatment options. In cases of non-union, the monitoring capability of the medical device 2400 identifies non-healing fractures earlier than image monitoring, thereby allowing for consideration of other options for the patient, such as a new surgery, e.g., hip replacement. The medical device 2400 also provides improved clinician workflow by providing useful information relatively automatically; and by providing relevant remote patient monitoring (RPM) data over a period of time that is likely to satisfy minimum requirements for reimbursement.

With reference to FIGS. 22A, 22B, and 24B, considering embodiments of the smart medical device wherein the sensor components of the sensor system 2229 are included in a single medical device, in one particular configuration, a medical device 2400 may have a plurality of electrodes 2420 along its shaft. In this configuration, the switch controller 2234 may be configured to control the electrode switch 2223 to select the first electrode 2428 and the second electrode 2430 from among the plurality of electrodes 2420 by testing various electrode pairs to: first, determine the location of the bone fracture 2408, and second, select an electrode on a first side 2460 of the bone fracture to serve as the first electrode 2428 and an electrode on a second side 2462 of the fracture to serve as the second electrode 2430.

Fracture location may be determined by obtaining impedance measurements between adjacent pairs of electrodes along the shaft of the medical device 2400 until a measurement indicative of a fracture is obtained. For example, the fracture 2408 may be determined to be between the pair of electrodes with the highest impedance measurement. Regarding the selection of the first electrode 2428 and the second electrode 2430, while any electrode on either side may be selected, electrodes that are closely spaced apart tend to provide more accurate impedance measurements. Accordingly, as a general rule, the electrodes closest to the bone fracture 2408, but on opposite sides thereof are selected as the first electrode 2428 and the second electrode 2430.

An initial electrode selection may occur during implant of the medical device through a physician interface, e.g., programmer, that is configured to detect bone fracture location relative to pairs of electrodes based on impedance measurements. To this end, the external programmer may control the implanted switch controller 2234 to implement the electrode selection process described above.

With continued reference to FIGS. 22A, 22B, and 24B, in another configuration of the smart medical device wherein the sensor components of the sensor system 2229 are included in a single medical device, the medical device 2400 may further include a third electrode 2448 and a fourth electrode 2450 at the exterior surface of the structure 2402, and the one or more electrical components include a signal generator and an impedance sensor. The first electrode 2428 and the second electrode 2430 are coupled to the signal generator to enable an application mode during which a signal, e.g., current, is applied across the first and second electrodes. The third electrode 2448 and the fourth electrode 2450 are couple to the impedance sensor to enable a sensing mode during which a voltage potential between the third and fourth electrodes is measured and from an impedance is calculated based on the current applied across the first and second electrodes.

With reference to FIGS. 22A, 22B, and 24C, considering embodiments of the smart medical device wherein the sensor components of the sensor components are located across a number of different structures of a medical device, in one particular configuration, a medical device 2400 includes a first structure 2402 configured to be at least partially implanted in the bone 2410, the first structure having at least one first electrode 2428, and a second structure 2404 configured to be at least partially implanted in the bone, the second structure having at least one second electrode 2430, and a third implant or structure 2406 configured to be placed on the bone across the bone fracture 2408 and secured in place by the first structure and the second structure. One or more electrical components are associated with one or more of the first structure 2402, the second structure 2404, and the third implant or structure 2406. These electrical components comprise a sensor that is configured to enable the measuring of tissue impedance between the first electrode 2428 and the second electrode 2430.

With reference to FIG. 22A, and as mentioned above, in some embodiments the IRP 2203 may include one or more other sensors 2222 besides an impedance sensor 2229. Representative examples of other sensors 2222 suitable for use within an IRP 2203 include ultrasound sensors, fluid pressure sensors, fluid volume sensors, contact sensors, position sensors, pulse pressure sensors, blood volume sensors, blood flow sensors, chemistry sensors (e.g., for blood and/or other fluids), metabolic sensors (e.g., for blood and/or other fluids), impedance sensors, electrical conductivity sensors, optical sensors, acoustic sensors, accelerometers, gyroscopes, mechanical stress sensors and temperature sensors.

A wide variety of sensors (also referred to as Microelectromechanical Systems or "MEMS", or Nanoelectromechanical Systems or "NEMS", and BioMEMS or BioNEMS, see generally https://en.wikipedia.org/wiki/MEMS) can be utilized. Representative patents and patent applications include U.S. Pat. Nos. 7,383,071, 7,450,332; 7,463,997, 7,924,267 and 8,634,928, and U.S. Publication Nos. 2010/0285082, and 2013/0215979. Representative publications include "Introduction to BioMEMS" by Albert Foch, CRC Press, 2013; "From MEMS to Bio-MEMS and Bio-NEMS: Manufacturing Techniques and Applications by Marc J. Madou, CRC Press 2011; "Bio-MEMS: Science and Engineering Perspectives, by Simona Badilescu, CRC Press 2011; "Fundamentals of BioMEMS and Medical Microdevices" by Steven S. Saliterman, SPIE—The International Society of Optical Engineering, 2006; "Bio-MEMS: Technologies and Applications", edited by Wanjun Wang and Steven A. Soper, CRC Press, 2012; and "Inertial MEMS: Principles and Practice" by Volker Kempe, Cambridge University Press, 2011; Polla, D. L., et al., "Microdevices in Medicine," Ann. Rev. Biomed. Eng. 2000, 02:551-576; Yun, K. S., et al., "A Surface-Tension Driven Micropump for Low-voltage and Low-Power Operations," J. Microelectromechanical Sys., 11:5, October 2002, 454-461; Yeh, R., et al., "Single Mask, Large Force, and Large Displacement Electrostatic Linear Inchworm Motors," J. Microelectromechanical Sys., 11:4, August 2002, 330-336; and Loh, N. C., et al., "Sub-10 cm3 Interferometric Accelerometer with Nano-g Resolution," J. Microelectromechanical Sys., 11:3, June 2002, 182-187; all of the above of which are incorporated by reference in their entirety.

A sensor 2222 may be located on a printed circuit board of the electronics assembly 2210, or in or on another structure of the smart medical device separate from the IRP 2203, but electrically coupled to the electronics assembly. Within certain embodiments a sensor 2222 may comprise a processor or may couple to a processor located on a printed circuit board of the electronics assembly 2210. In other embodiments, the sensor can be a wireless sensor. Within further embodiments one or more (including all) of the sensors can have a Unique Sensor Identification (USI) number which specifically identifies the sensor.

A sensor 2222 may be an ultrasound sensor utilized to characterize bone fracture healing based on known ultrasound techniques. To this end, an ultrasound sensor of suitable size and with power requirements supportable by the medical device may be located in a structure, e.g., cannulated screw or electronics cartridge, of the medical device that places the sensor at or near a bone fracture site upon implant of the medical device. Ultrasound measurements of tissue at fracture site may be obtained overtime and processed to provide one or more of a characterization of a bone fracture, and a characterization of tissue in the area of the structure.

A sensor 2222 may be a strain sensor utilized to characterize bone fracture healing based on known mechanical stress/strain techniques. To this end, a strain sensor may be located in a structure, e.g., cannulated screw or electronics cartridge, of the medical device that places the sensor at or near a bone fracture site upon implant of the medical device. Strain measurements at the fracture site may be obtained overtime and processed to provide one or more of a characterization of a bone fracture, and a characterization of tissue in the area of the structure.

A sensor 2222 may be a glucose detector or an oxygen sensor utilized to characterize tissue inflammation based on known techniques. To this end, a glucose detector or an oxygen sensor may be located in a structure, e.g., cannulated screw or electronics cartridge, of the medical device that places the sensor at or near a bone fracture site upon implant of the medical device. Sensor measurements at the tissue of the fracture site may be obtained overtime and processed using known techniques to provide an indication of inflammation fluid, interstitial fluids, or other biological fluids, e.g., blood, in a region of the device.

A sensor 2222 may be utilized to detect, measure and/or monitor information relevant to the state of the device after implantation. The state of the device may include the integrity of the device (device breakage), the movement of the device (device backout), the forces exerted on the device and other information relevant to the implanted device. Examples of these types of sensors 2222 include gyroscopes, accelerometers, and temperature and pressure sensors.

A sensor 2222 may be utilized to detect, measure and/or monitor information relevant to the state of a body or body segment after implantation of the device. The state of the body or a body segment may include kinematic information of the body or a body segment. Examples of these types of sensor 2222 include gyroscopes, accelerometers, and temperature and pressure sensors coupled to the processor. In some embodiments, a sensor 2222 is an inertial measurement unit (IMU) such as an accelerometer or gyroscope configured to output a signal corresponding to motion of the medical device 100, and by association, motion of the boney structure in which the device is implanted, and motion or activity of the patient in which the device is implanted.

A sensor 2222 may be utilized to detect, measure and/or monitor information relevant to body tissue after implantation of the device. Body tissue monitoring may include blood pressure, pH level. Examples of this type of sensor 2222 include fluid pressure sensors, fluid volume sensors, pulse pressure sensors, blood volume sensors, blood flow sensors, chemistry sensors (e.g., for blood and/or other fluids), metabolic sensors (e.g., for blood and/or other fluids). A sensor 2222 may be utilized to monitor temperature in the region of the device for purposes of detecting infection.

The power supply 2212 is configured to generate a regulated supply signal in an approximate range of 1-24 Volts (V) to power the components of the IRP 2203. The power supply 2212 may include one or more of a battery, a rechargeable power device (e.g., a rechargeable battery or a super capacitor), and an energy harvester.

In some embodiments, the power supply 2212 of the IRP 2203 may be any suitable battery, such as a Lithium Carbon Monofluoride (LiCFx) battery, or other storage cell configured to store energy for powering components of the electronics assembly 2210 for an expected lifetime (e.g., 5-25+ years) of the smart medical device.

The size of the power supply 2212 is generally constrained by the size of a structure, e.g., cannulated screw, electronics cartridge shell, of the medical device. For example, with reference to FIGS. 13C and 13D, the diameter of the power supply 1354 is limited by the diameter of the inner lumen 1304 of the cannulated screw 1302. In another example, with reference to FIGS. 17A-17C, the diameter of the power supply 1754 is limited by the diameter of the shaft 1726 of the electronics cartridge 1706. In yet another example, with reference to FIGS. 19A and 19B, the diameter of the power supply 1954 is limited by the diameter of the lower cavity of the structure 1902. In example designs, the diameter of the battery may be greater than 1 mm and generally in the range of 1 mm to 5 mm. The length of the battery may be greater than 1 mm and generally a minimum of 3 mm. The volume of the battery may be greater than 2 $mm^2$. The battery capacity may be greater than 1 mAh, though based on measurement and communication more energy, e.g., about 100 mAh, may be needed. Power required for full charge in one hour may be greater than 5 mW and generally in the range of 5 mW to 150 mW.

In some embodiments, the power supply 2212 of the IRP 2203 may be a supercapacitor. Supercapacitors are attractive due to their fast charge/discharge characteristics, e.g., 2.8 mAh battery is rated at 0.2 C charge/discharge→5 hours charge time. They also have increased current delivery capability compared to batteries. The supercapacitor may be an electrochemical double layer capacitor (EDLC) supercapacitor or a wire shaped supercapacitor. Commercially available EDLCs are only half the volumetric energy density of "advanced" wired shaped supercapacitors. Accordingly, wire shaped supercapacitors may be preferred.

Example characteristics and specifications for a wire shaped supercapacitor include: form factor (2×0.5 mm OD wires), gravimetric energy density of 153.3 Wh $kg^{-1}$ (⅓ of LiCFx), power density of 8810 W $kg^{-1}$ (20 times of LiCFx). Example characteristics and specifications for EDLC include form factor (3.2×2.5×0.9 mm), single-digit µAh, 2.3 mWh $cm^{-3}$.

In some embodiments, the power supply 2212 of the IRP 2203 may be a hybrid solution. In this configuration, the IRP includes a first power supply, e.g., a primary battery, for measurements, and a second power supply, e.g., a supercapacitor, for temporarily buffering energy while exchanging data.

The power supply 2212 of the IRP 2203 may be a rechargeable power device, such as a lithium-ion battery or a supercapacitor. In this case, the power supply 2212 and/or the electronics assembly 2210 includes additional components for charging the power source by an external recharge unit. These additional components may include a power coil configured to generate a voltage and current in response to a magnetic field generated by an external recharge unit. Possible modes of energy transfer include a far-field RF, near-field RF and ultrasonic.

In an example configuration of far-field RF energy transfer, operation parameters include: power: 0.24/32 mW, frequency: 2.34/1 GHz, efficiency: 12/0.2%, antenna size: 9/2160 $mm^2$, range: 20/150 cm, allowable specific absorption rate (SAR) limits (1.6 W/kg) restrict power transfer. Far-field energy transfer may be directed with multiple antennas. Furthermore, far-field energy transfer may be implemented using an antenna that is used for communications. For example, the antenna 144b of FIG. 9B may be used for both RF energy transfer and RF communications.

In an example configuration of near-field RF energy transfer, operation parameters include: power: 0.2/15.7 mW, frequency: 10 MHz/1.5 GHZ, efficiency: 15.2/0.5%, antenna size: 2.3/6 $mm^2$, and depth: 0.5/3 cm. Near-field energy transfer involves precise tuning and alignment, and close contact with the skin.

In an example configuration of ultrasonic energy transfer, operation parameters include: power: 0.36 mW @ 1 MHz, efficiency up to 5.6%, transducer size: 1×1 $mm^2$, depth: a minimum of 5 mm or more as relating to maximum thickness of a person with BMI (Body Mass Index) up to 45. In this configuration it may be possible to transmit energy over tissue depths greater than 10 cm. Ultrasonic energy transfer may have reduced efficiency when traveling through multiple tissue types, and involves direct contact with the skin.

The energy harvester is configured to convert an environmental stimulus into an energy for charging a rechargeable power device. For example, the harvester may convert, into a battery-charging electrical current or voltage or a supercapacitor-charging, one or more of body heat from the subject in which the IRP 2203 is implanted, kinetic energy generated by the subject's movement, changes in pressure (e.g., barometric pressure or pressure within the subject, such as the subject's blood pressure), energy generated by an electrochemical reaction within the subject's body, energy generated by radio-frequency (RF) fields, light, electromechanical conversion (such as piezoelectric), or electromagnetic conversion.

The fuse 2214 can be any suitable fuse (e.g., permanent) or circuit breaker (e.g., resettable) configured to prevent the power supply 2212, or a current flowing from the battery, from injuring the patient and damaging the battery and one or more components of the electronics assembly 2210. For example, the fuse 2214 can be configured to prevent the power supply 2212 from generating enough heat to burn the patient, to damage the electronics assembly 2210, to damage the battery, or to damage structural components of the smart implantable implant.

A first power switch 2216 is configured to couple the power supply 2212 to, or to uncouple the power supply from, the one or more sensors 2222 in response to a control signal from the controller 2232. For example, the controller 2232 may be configured to generate the control signal having an open state that causes the switch 2216 to open, and, therefore, to uncouple power from the one or more sensors 2222, during a sleep mode or other low-power mode to save power, and, therefore, to extend the life of the power supply 2212. Likewise, the controller 2232 also may be configured to generate the control signal having a closed state that causes the switch 2216 to close, and therefore, to couple power to the one or more sensors 2222, upon "awakening" from a sleep mode or otherwise exiting another low-power mode. Such a low-power mode may be for only the one or more sensors 2222 or for the sensors and one or more other components of the electronics assembly 2210.

A second power switch 2218 is configured to couple the power supply 2212 to, or to uncouple the power supply from, the memory 2224 in response to a control signal from the controller 2232. For example, the controller 2232 may be configured to generate the control signal having an open state that causes the switch 2218 to open, and, therefore, to uncouple power from the memory 2224, during a sleep mode or other low-power mode to save power, and, therefore, to extend the life of the power supply 2212. Likewise, the controller 2232 also may be configured to generate the control signal having a closed state that causes the switch 2218 to close, and therefore, to couple power to the memory 2224, upon "awakening" from a sleep mode or otherwise exiting another low-power mode. Such a low-power mode may be for only the memory 2224 or for the memory and one or more other components of the electronics assembly 2210.

The clock and power management unit 2220 can be configured to generate a clock signal for one or more of the other components of the electronics assembly 2210, and can be configured to generate periodic commands or other signals (e.g., interrupt requests) in response to which the controller 2232 causes one or more components of the IRP 2203 to enter or to exit a sleep, or other low-power, mode. The clock and power management unit 2220 also can be configured to regulate the voltage from the power supply 2212, and to provide a regulated power-supply voltage to some or all of the other components of the electronics assembly 2210.

The memory 2224 may include volatile memory and non-volatile memory. For example, the volatile memory may be configured to store the operating system and one or more applications executed by the controller 2232. The non-volatile memory may be configured to store configuration information for the IRP 2203 and to store data written by the controller 2232, and to provide data in response to a read command from the controller.

The IRP 2203 of the medical device includes a communication interface which facilitates communication between the medical device and another device. The other device may be, for example, an external device, e.g., a base station, that is located outside of or away from the patient who has received the medical device, or it may be an internal device that is located in the patient who has received the medical device. In either case, communication between an implanted medical device and another device, whether internal or external, is referred to as intra-body communication. One or modes of intra-body communication may be enabled by the communication interface of the IRP 2203. As previously disclosed, possible modes of intra-body communication include: 1) RF telemetry communication, 2) tissue conductive communication, e.g., galvanic coupling communication, and 3) data-over-sound communication, e.g. ultrasound or acoustic communication.

The communication interface includes communication circuitry 2225 that is generally, but not necessarily, associated with the electronics assembly 2210 of the IRP 2203. The communication circuitry 2225 may include any hardware, firmware, software or any combination thereof suitable for enabling one or more modes of intra-body communication. To this end, the communication circuitry 2225 may include, for example, voltage regulators, current generators, oscillators, or circuitry for generating a signal, resistors, capacitors, inductors, and other filtering circuitry for processing received signals, as well as circuitry for modulating and/or demodulating a signal according to a communication protocol.

Depending on the mode of intra-body communication, the communication circuitry 2225 may also include transistors or other switching circuitry for selectively coupling transmitted signals to or receiving signals from a desired transceiver, such as an antenna 2230 (which may be used for electromagnetic communication, e.g., RF telemetry communication) or electrodes 2231, 2233 (which may be used for tissue conductive communication) or an acoustic transducer 2236 (which may be used for data-over-sound communication). Under the control of the controller 2232, communication circuitry 2225 may receive downlink communication signals from, as well as send uplink communication signals to, an external device or another implanted device. In addition, communication circuitry 2225 may communicate with a networked computing device via an external device and a computer network, such as the Medtronic CareLink(R) Network developed by Medtronic, plc, of Dublin, Ireland.

Additional details on each of the RF telemetry communication, tissue conductive communication, and data-over-sound communication modes of intra-body communication follow.

An RF telemetry mode of intra-body communication is enabled by an RF communication interface that includes an antenna 2230 and RF telemetry circuitry, e.g., an RF transceiver 2226 and a filter 2228. Possible modes of RF communication include far-field RF and near-field RF. The RF transceiver 2226 can be a conventional transceiver that is configured to allow the controller 2232 (and optionally the fuse 2214) to communicate with another implanted medical device (not shown in FIG. 22A), or with a base station (not shown in FIG. 22A) configured for use with the smart implantable device. For example, the RF transceiver 2226 can be any suitable type of transceiver (e.g., Bluetooth, Bluetooth Low Energy (BTLE)), and WiFi®), can be configured for operation according to any suitable protocol (e.g., MICS, ISM, Bluetooth, Bluetooth Low Energy (BTLE), and WiFi®), and can be configured for operation in a frequency band that is within a range of 1 MHZ-5.4 GHz, or that is within any other suitable range. In an example configuration of far-field RF communication, the frequency band may be 401-406 MHz or 2.4 GHz. On some embodiments different frequencies may be used for different purposes. For example, in one configuration 2.4 GHz may be used to wake-up a device, while 400 MHz is used for communications.

In the case of far-field RF communication, the antenna 2230 may be a monopole, dipole, folded dipole, meander loading, loop, small loop, MEMs on-chip, or helical antenna. Furthermore, far-field RF communication may be implemented using an antenna that is used for energy transfer. For example, the antenna 144b of FIG. 9B may be used for both RF energy transfer and RF communications.

The filter 2228 can be any suitable bandpass filter, such as a surface acoustic wave (SAW) filter or a bulk acoustic wave (BAW) filter. The antenna 2230 can be any antenna suitable for the frequency band in which the RF transceiver 2226 generates signals for transmission by the antenna, and for the frequency band in which a base station (not shown in FIG. 22A) generates signals for reception by the antenna.

A tissue conductive communication (TCC) mode of intra-body communication is enabled by a TCC interface that includes TCC circuitry 2238 and a pair of electrodes 2231, 2233. The pair of electrodes 2231, 2233 may be selected from the sensing electrodes 2221 and coupled to the TCC circuitry 2238 through the electrode switch 2223. Alternatively, the pair of electrodes may be electrodes 2231, 2233 that are sensing electrodes 2221. The TCC interface allows the controller 2232 to communicate with another device having a same TCC interface as the IRP 2203. The other device may be an implanted medical device (not shown in FIG. 22A), or a base station (not shown in FIG. 22A) configured for use with the medical device.

Tissue conductive communication relies on the ion content of body tissue of a patient within which the smart medical device 2202 has been implanted, and is thus frequently referred to as galvanic communication. The ion content of the body tissue provides an electrical communication medium over which to send and receive information to and from the smart medical device. To communicate in a transmit mode, the TCC circuitry 2238 applies a voltage across the electrodes 2231, 2233 to cause current to flow between the electrodes and a corresponding electrical signal to propagate through the body tissue. The propagating current may be detected by a receiving device (not shown in FIG. 22A) by measuring the voltage generated between two electrodes. To communicate in a receive mode, the TCC circuitry 2238 measures voltage across the electrodes 2231, 2233.

When tissue conductive communication is employed to facilitate communication, the sensing attachment and the other device that receives and/or sends information to the sensing attachment, have associated hardware, firmware, software or any combination thereof suitable for providing such communication. TCC transmission and associated hardware, firmware, software have been described and may be included in the smart implantable device of the present disclosure. See, e.g., U.S. Patent Publication Nos. US2016213939, US2018207429, US2019160290, US2019160291, US2019160292, US2019184181. For example, in one aspect, the TCC circuitry 2238 may be coupled to one or more electrodes 2231, 2233, and configured with circuitry that enables the TCC interface to switch between a transmit mode during which TCC signals are transmitted, and a receive mode during which TCC signals are received from another similarly configured device.

A data-over-sound mode of intra-body communication is enabled by a data-over-sound communication interface that includes data-over-sound circuitry 2240 and at least one acoustic transducer 2236. The data-over-sound communication interface allows the controller 2232 to communicate with another device having a same data-over-sound communication interface as the IRP 2203. The other device may be an implanted medical device, or a base station configured for use with the smart implantable device.

When data-over-sound communication is employed to facilitate communication, the smart medical device and the other device that receives and/or sends information to the smart implantable device, have associated hardware, firmware, software or any combination thereof suitable for providing such communication. Data-over-sound communication transmission and associated hardware, firmware, software have been described and may be included in the smart medical device of the present disclosure. See, e.g., U.S. Patent No. U.S. Pat. No. 7,489,967 and U.S. Patent Publication Nos. US20100249882A1 and US20130033966A1. For example, in one aspect, the data-over-sound circuitry 2240 may be coupled to an acoustic transducer 2236 and configured with circuitry that enables the data-over-sound communication interface to switch between a transmit mode during which ultrasound signals are transmitted, and a receive mode during which ultrasound signals are received from another similarly configured device.

The controller 2232, which can be any suitable microcontroller or microprocessor, is configured to control the configuration and operation of one or more of the other components of the electronics assembly 2210. For example, the controller 2232 is configured to control the one or more sensors 2222, 2229 to sense relevant measurement data, to store the measurement data generated by the one or more sensors in the memory 2224. The controller 2232 is also configured to generate message for communication over one or more types of communication interfaces. For example, in the case of RF telemetry communication, the controller 2232 generates messages that include the stored data as a payload, packetizes the messages, and provides the message packets to the RF transceiver 2226 for transmission to the base station (not shown in FIG. 22A). The controller 2232 also can be configured to execute commands received from a base station (not shown in FIG. 22A) via a communication interface, e.g., the antenna 2230, filter 2228, and RF transceiver 2226. For example, the controller 2232 can be configured to receive configuration data from the base station, and to provide the configuration data to the component of the electronics assembly 2210 to which the base station directed the configuration data. If the base station directed the configuration data to the controller 2232, then the controller is configured to configure itself in response to the configuration data.

In one aspect, the medical device of the present disclosure is sterile. In one aspect, the medical device of the present disclosure has been subjected to a sterilization procedure to provide a sterile medical device. In various options, the medical device can be sterilized using an alcohol solution, by exposing the device to ethylene oxide, ionizing radiation, autoclaving, ultra-violet radiation or dry heat. Alcohol solutions that can be used include but are not limited to methanol, ethanol, isopropanol and aqueous solutions thereof. The ionizing radiation used can include gamma radiation and electron beam radiation. The dose of ionizing radiation used for sterilization is greater than 20 kGy, greater than 25 kGy, greater than 30 kGy, greater than 35 kGy or greater than 40 kGy. For a device that is sterilized using ethylene oxide, the sterilized device preferably complies with ISO 10993-7 for residual ethylene oxide and ethylene chlorohydrin levels.

The medical device of the present disclosure can be in a non-sterile form. In an aspect, the non-sterile medical device complies with the requirements of USP <1111>. In an aspect, the non-sterile device has a total aerobic microbial count (cfu/g or cfu/mL) of 102 or less. In an aspect, the non-sterile device has a total combined yeasts/molds count (cfu/g or cfu/mL) of 101 or less. In an aspect, the non-sterile device has a total aerobic microbial count (cfu/g or cfu/ml) of 102 or less and a total combined yeasts/molds count (cfu/g or cfu/mL) of 101 or less. The non-sterile contraceptive device cannot be contaminated with *Pseudomonas aeruginosa*, *Staphylococcus aureus* or *Candida albicans*.

Implant Locations

With reference to FIGS. 24A and 24B, in some embodiments, the structure 2402 of the medical device 2400 is configured to be implanted to bridge a bone fracture 2408 of a bone 2410. For example, in FIG. 24A, the medical device 2400 may be one of two devices arrange parallel to each other to bridge a femoral neck fracture 2408. In another example, shown in FIG. 24B, the medical device 2400 may be one of three devices that are implanted to form a triangle and to bridge a femoral head hip fracture 2408, with the other two devices 2422, 2424 being only cannulated screws. In this example, the medical device 2400 is implanted at the apex of the triangle at the location have the least amount of load of the three locations. In another embodiment, the medical device 2400 may be implanted only for purposes of monitoring bone healing and does not serve any support or load bearing function related to the orthopedic treatment provided by the other devices. To this end, the medical device 2400 may be implanted at the center of surrounding orthopedic support devices, e.g., at the center of a triangle, with an orthopedic support device being implanted at each apex of the triangle.

With reference to FIG. 24C, in some embodiments, the medical device 2400 includes a pair of smart structures 2402, 2404, each configured to be implanted through a respective hole in a plate 2406 that bridges a bone fracture 2408 of a bone 2410, such as a humeral shaft fracture.

Figure 24D:
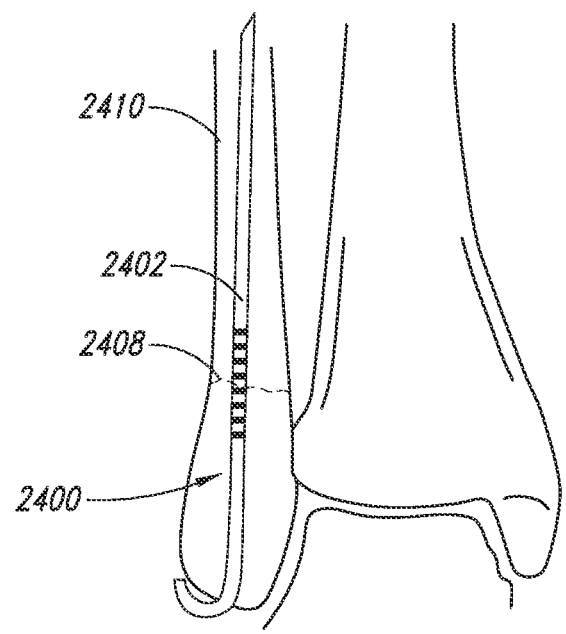
Figure 24E:
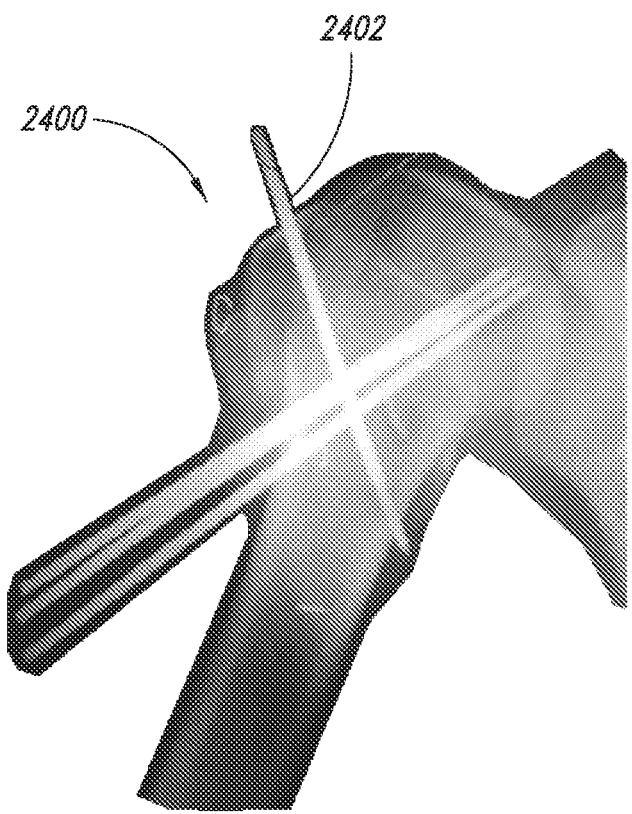

With reference to FIGS. 24D and 24E, in some embodiments the medical device 2400 is a structure 2402, e.g., a rod or a pin, configured to be implanted to bridge a bone fracture 2408 of a bone 2410. For example, in FIG. 24D, the structure 2402 of the medical device 2400 is a push rod that bridges a distal fibular fracture. In FIG. 24E, the structure 2402 of the medical device 2400 is one of four percutaneous pins that bridges a fracture of a neck humerus.

Bone Fracture Characterization Devices and Methods

Figure 25A:
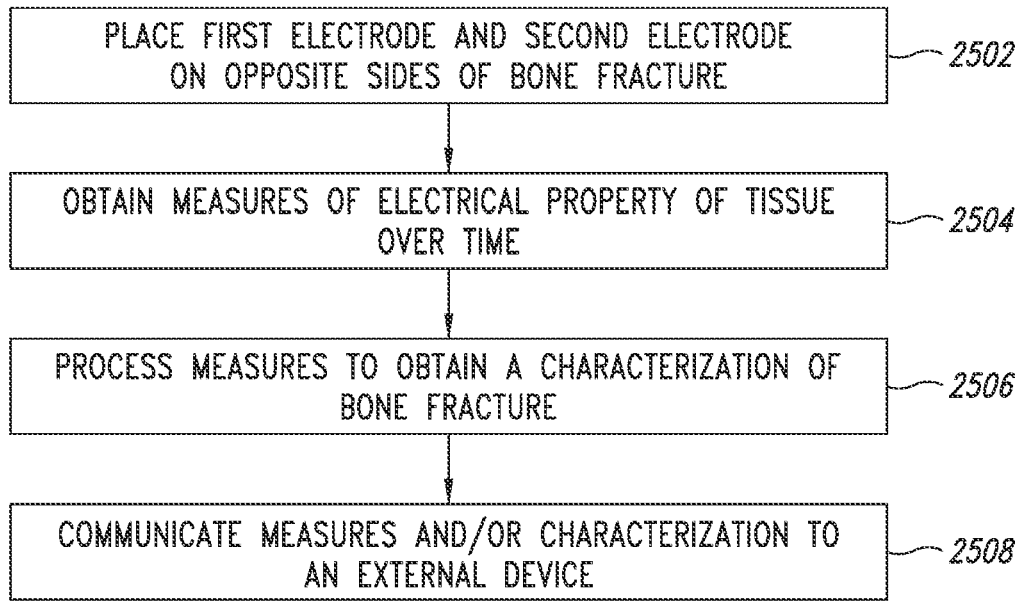
FIGS. 25A and 25B are respectively, a flowchart and a schematic representation of a method of characterizing a bone fracture with a smart medical device.
Figure 25B:
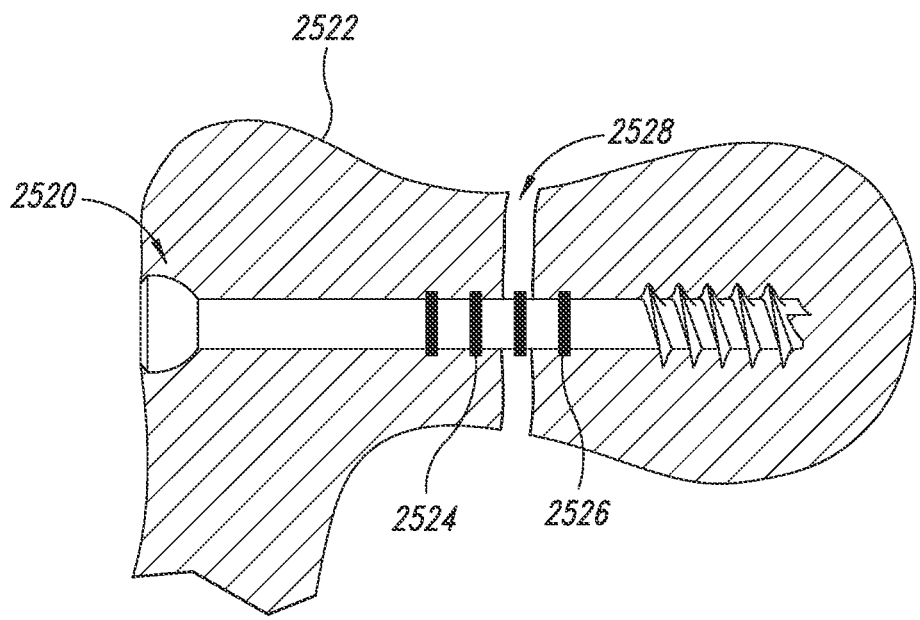

FIGS. 25A and 25B are respectively, a flowchart and a schematic representation of a method of characterizing a bone fracture. The method may be performed by one of the smart medical devices disclosed herein and further configured as described below.

At block 2502, a smart medical device 2520 having a plurality of electrodes is implanted in boney tissue 2522 to place a first electrode 2524 and a second electrode 2526 on opposite sides of a bone fracture 2528. In some methods, the plurality of electrodes are implanted by implanting a cannulated structure having a lumen into the boney tissue, and across the bone fracture. After the cannulated structure is implanted, an electronics cartridge with a sensing module and other electronics is inserted into the lumen. In some methods, the cannulated structure includes the plurality of electrodes and the electrodes couple to the sensing module upon insertion of the electronics cartridge into the lumen. In some methods, the plurality of electrodes are included in the electronics cartridge, and interface with boney tissue through apertures in a sidewall of the cannulated structure, or through openings at the ends of the cannulated structure. In some methods, the plurality of electrodes are implanted by implanting a preloaded medical device having a structure that includes the plurality of electrodes, a sensing module, and other electronics coupled to the plurality of electrodes.

At block 2504, a plurality of measures of an electrical property of tissue are obtained overtime through the first electrode 2524 and the second electrode 2526 that are on opposite sides of the bone fracture 2528. The electrical property of tissue may correspond to impedance measurements, and the measures are obtained by applying signals at different frequencies to the first electrode 2524 to measure tissue impedance in accordance with EIS techniques.

At block 2506, the measures are processed to determine a characterization of the bone fracture 2528 that corresponds to a healing state of the bone fracture, e.g., union, likely non-union, and non-union.

At block 2508, the plurality of measures of the electrical property of tissue, or the characterization of a bone fracture 2528 are communicated to an external device.

Figure 26A:
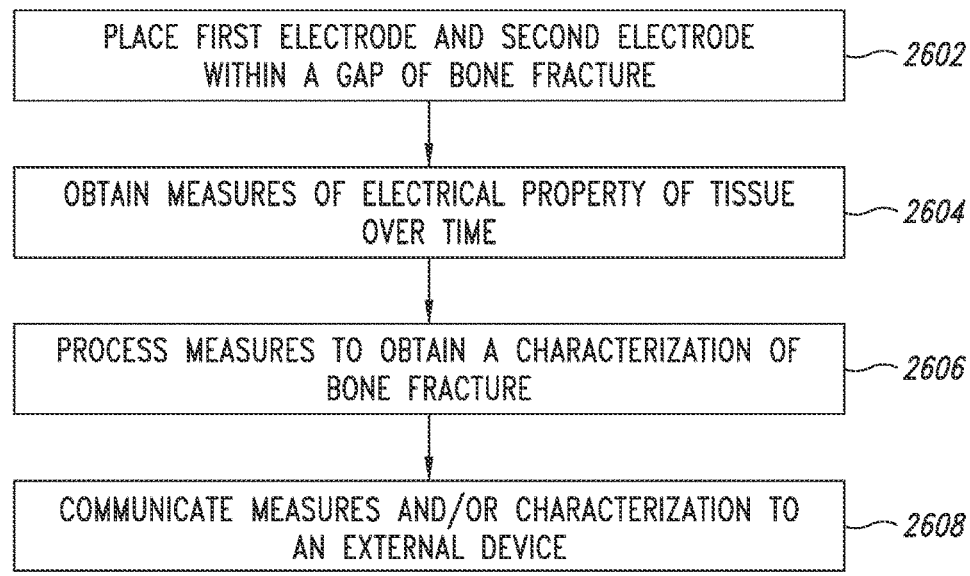
FIGS. 26A and 26B are respectively, a flowchart and a schematic representation of another method of characterizing a bone fracture with a smart medical device.
Figure 26B:
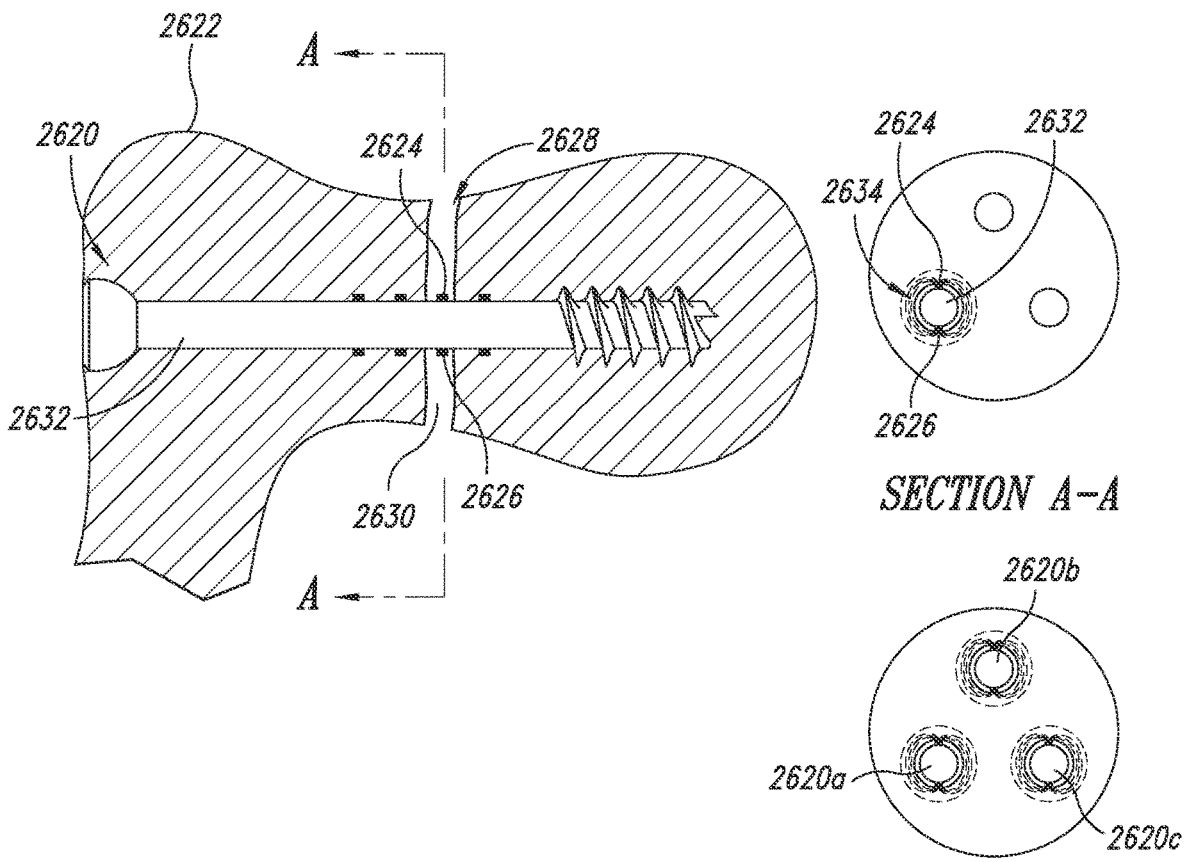

FIGS. 26A and 26B are respectively, a flowchart and a schematic representation of a method of characterizing a bone fracture. The method may be performed by one of the smart medical devices disclosed herein and further configured as described below.

At block 2602, a smart medical device 2620 having a plurality of electrodes is implanted in a bone 2622 to place each of a first electrode 2624 and a second electrode 2626 within a gap 2630 of a bone fracture 2628. In some methods, the plurality of electrodes are implanted by implanting a cannulated structure having a lumen into the boney tissue at the bone fracture. After the cannulated structure is implanted, an electronics cartridge with a sensing module and other electronics is inserted into the lumen. In some methods, the cannulated structure includes the plurality of electrodes and the electrodes couple to the sensing module upon insertion of the electronics cartridge into the lumen. In some methods, the plurality of electrodes are included in the electronics cartridge, and interface with boney tissue through apertures in a sidewall of the cannulated structure. In some methods, the plurality of electrodes are implanted by implanting a preloaded medical device having a structure that includes the plurality of electrodes, a sensing module, and other electronics coupled to the plurality of electrodes.

At block 2604, a plurality of measures of an electrical property of tissue are obtained overtime through the first electrode 2624 and the second electrode 2626 that are within the gap 2630 of the bone fracture 2628. The electrical property of tissue may correspond to impedance measurements, and the measures are obtained by applying signals at different frequencies to the first electrode 2624 to measure tissue impedance in accordance with EIS techniques.

At block 2606, the measures are processed to determine a characterization of the bone fracture 2628 that corresponds to a healing state of the bone fracture, e.g., union, likely non-union, and non-union.

At block 2608, the plurality of measures of the electrical property of tissue, or the characterization of a bone fracture 2628 are communicated to an external device.

With reference to FIG. 26B, the smart medical device 2620 includes a first set of electrodes on a first side of a shaft 2632 of the medical device and a second set of electrodes on a second side of the shaft spaced apart from the first side. This embodiment of the medical device may be based on, for example, the embodiment of FIGS. 21A and 21B, but modified to include two sets of four pin electrodes. Continuing with FIG. 26B, the smart medical device 2620 is placed in the patient's bone 2622 such that the first set of electrodes and the second set of electrodes span the bone fracture 2628, while at least one electrode of each set is within the gap 2630. The electrodes are located on the shaft 2632 such that a first electrode 2624 is on one side of the shaft and a second electrode 2626 is on the other side of the shaft. The shaft 2632 may be insulated (e.g., anodized titanium). This creates an electrical path 2634 from the first electrode 2624 to the second electrode 2626 through the healing bone in the gap 2630. This provides a high change in impedance as the fracture site heals. However, the electrical path 2634 may be localized to the area immediately around the shaft 2632. Accordingly, to better understand healing over the entire fracture site, multiple medical devices 2620a, 2620b, 2620c of this style may be employed to place multiple pairs of electrodes within the gap 2630 at multiple location of the gap cross-section to thereby collect sets of impedance measurements at different locations of the gap.

Figure 27A:
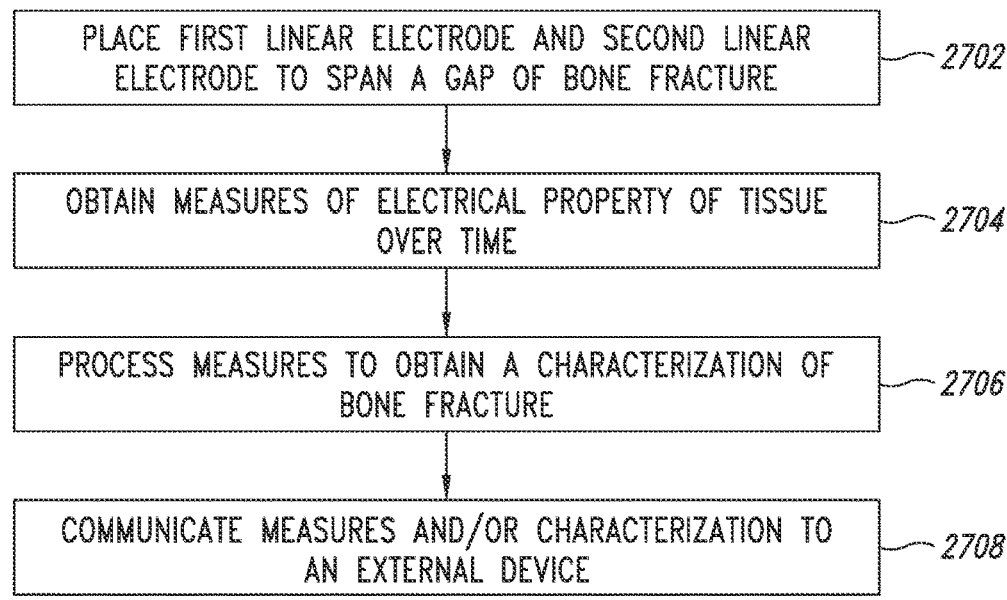
FIGS. 27A and 27B are respectively, a flowchart and a schematic representation of another method of characterizing a bone fracture with a smart medical device.
Figure 27B:
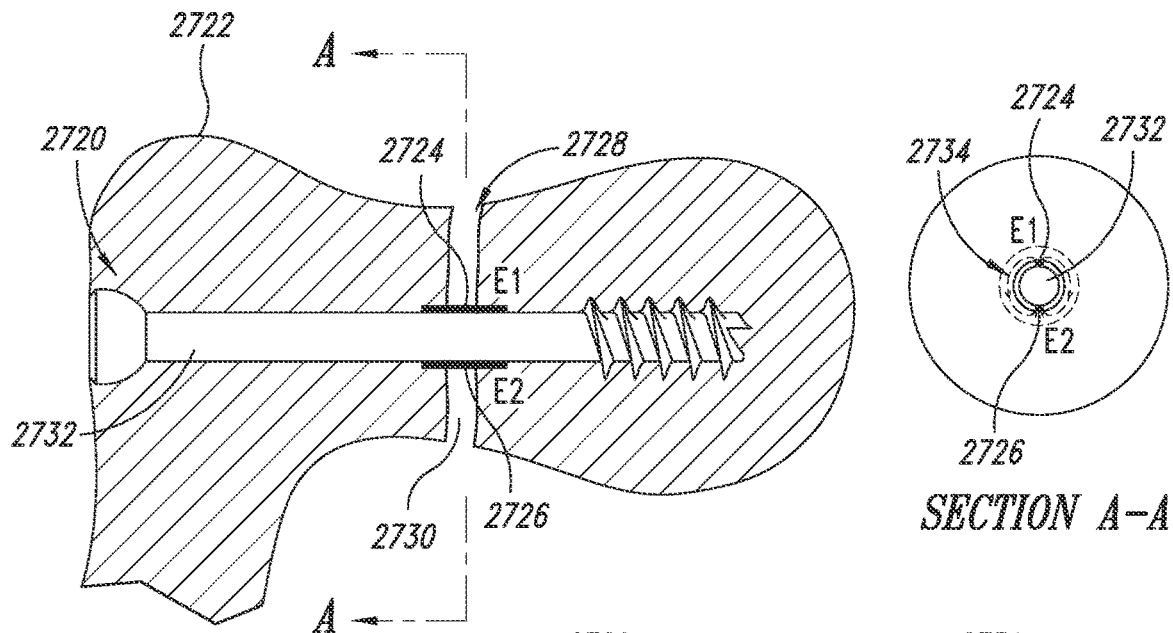
Figure 27B:
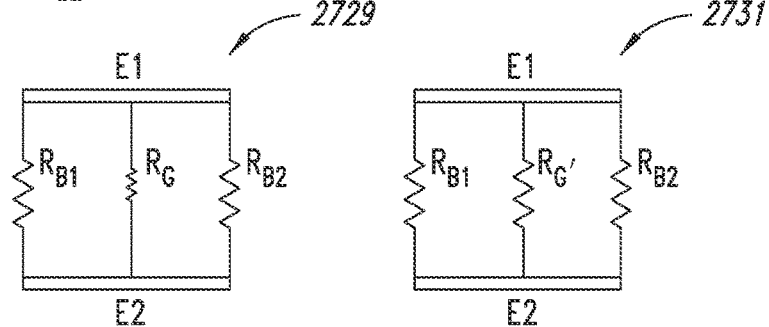

FIGS. 27A and 27B are respectively, a flowchart and a schematic representation of a method of characterizing a bone fracture. The method may be performed by one or more of the smart medical devices disclosed herein and further configured as described below.

At block 2702, a smart medical device 2720 having a plurality of electrodes is implanted in bone 2722 to place each of a first linear electrode 2724 and a second linear electrode 2726 such that each linear electrode spans a gap 2730 of a bone fracture 2728. The linear electrodes 2724, 2726 may be at least 1 mm in length. In some methods, the plurality of electrodes are implanted by implanting a cannulated structure having a lumen into the boney tissue at the bone fracture. After the cannulated structure is implanted, an electronics cartridge with a sensing module and other electronics is inserted into the lumen. In some methods, the cannulated structure includes the plurality of electrodes and the electrodes couple to the sensing module upon insertion of the electronics cartridge into the lumen. In some methods, the plurality of electrodes are included in the electronics cartridge, and interface with boney tissue through slots in a sidewall of the cannulated structure. In some methods, the plurality of electrodes are implanted by implanting a preloaded medical device having a structure that includes the plurality of electrodes, a sensing module, and other electronics coupled to the plurality of electrodes.

At block 2704, a plurality of measures of an electrical property of tissue are obtained overtime through the first linear electrode 2724 and the second linear electrode 2726 that span the gap 2730 of the bone fracture 2728. The electrical property of tissue may correspond to impedance measurements, and the measures are obtained by applying signals at different frequencies to the first linear electrode 2724 to measure tissue impedance in accordance with EIS techniques.

At block 2706, the measures are processed to determine a characterization of the bone fracture 2728 that corresponds to a healing state of the bone fracture, e.g., union, likely non-union, and non-union.

At block 2708, the plurality of measures of the electrical property of tissue, or the characterization of a bone fracture 2728 are communicated to an external device.

With reference to FIG. 27A, the smart medical device 2720 includes a first linear electrode 2724 on a first side of a shaft 2732 of the medical device and a second linear electrode 2726 on a second side of the shaft spaced apart from the first side. This embodiment of the medical device may be based on, for example, the embodiment of FIGS. 13A-13D, but modified to include two linear electrodes, each configured to extend through a respective slot on opposite sides of a cannulated structure. Continuing with FIG. 27B, the smart medical device 2720 is placed in the patient's bone 2722 such that the first linear electrode 2724 and the second linear electrode 2726 span the bone fracture 2628. The linear electrodes 2724, 2726 are located on the shaft 2732 such that the electrodes are on opposite sides of the shaft. The shaft 2632 may be insulated (e.g. anodized titanium). This creates an electrical current path 2734 from the first linear electrode 2724 to the second linear electrode 2726 through the local area around the shaft 2732. Because the linear electrodes 2724, 2726 contact bone 2722 on either side of the fracture site, the current path 2734 is through the healing bone in the fracture site, and through bone on either side of the fracture site.

Illustrative circuit diagrams are shown for the initial state 2729 of the bone fracture 2728 and the healed state 2731 of the bone fracture. As the bone heals, the impedance in the gap 2730 of the bone fracture 2728 changes from a low resistance in the fractured state, RG, to a higher resistance in the healed state, RG', allowing the smart medical device 2720 to detect if healing has occurred in the local area around the shaft 2732. If the two linear electrodes 2724, 2726 are placed on each side of the shaft 2732, it is possible to use 4 wire impedance measurement to remove the effect of electrode contact resistance from this measurement. This embodiment tends to measure healing only in the local area around the shaft 2732. Accordingly, to better understand healing over the entire fracture site, multiple medical devices of this style may be employed to span multiple pairs of linear electrodes across the gap 2730 at multiple location of the gap cross-section to thereby collect sets of impedance measurements at different locations of the gap.

In one aspect, the present disclosure provides a method of treating a fracture in boney tissue, where the method includes identifying a fracture in boney tissue, and inserting a medical device as disclosed herein into the bony tissue, where the medical device is inserted across the fracture. The fracture may be identified by, e.g., x-ray. In one embodiment the medical device is a screw. The medical device may be inserted into the boney tissue according to standard techniques used to insert cannulated screws into bone having a fracture. Optionally, the method further includes characterizing the fracture with the medical device.

In one aspect, the present disclosure provides a method of characterizing a fracture in boney tissue, the method including identifying a fracture in boney tissue, inserting a medical device as disclosed herein into the bony tissue, where the medical device is inserted across the fracture; and characterizing the fracture with a sensor located in the medical device. The fracture may be identified by, e.g., x-ray. In one embodiment the medical device is a screw. The medical device may be inserted into the boney tissue according to standard techniques used to insert cannulated screws into bone having a fracture.

Communication with the Smart Medical Device

The smart medical device may be part of an environment which communicates with the smart medical device. An exemplary environment is an operating room wherein the smart medical device is being implanted into a patient by a health care profession. Another exemplary environment is the patient's home, in the case where the smart medical device has already been implanted in the patient. Yet another exemplary environment is a doctor's office, where the patient having the implanted smart medical device is in the office for, e.g., an evaluation. The following provides a detailed description of an exemplary environment in a patient's home. However, the described features and connectivity are analogously present in other environments within which the patient with the implanted smart medical device is present, e.g., the operating room and the doctor's office, as also described herein albeit in lesser detail.

Figure 28:
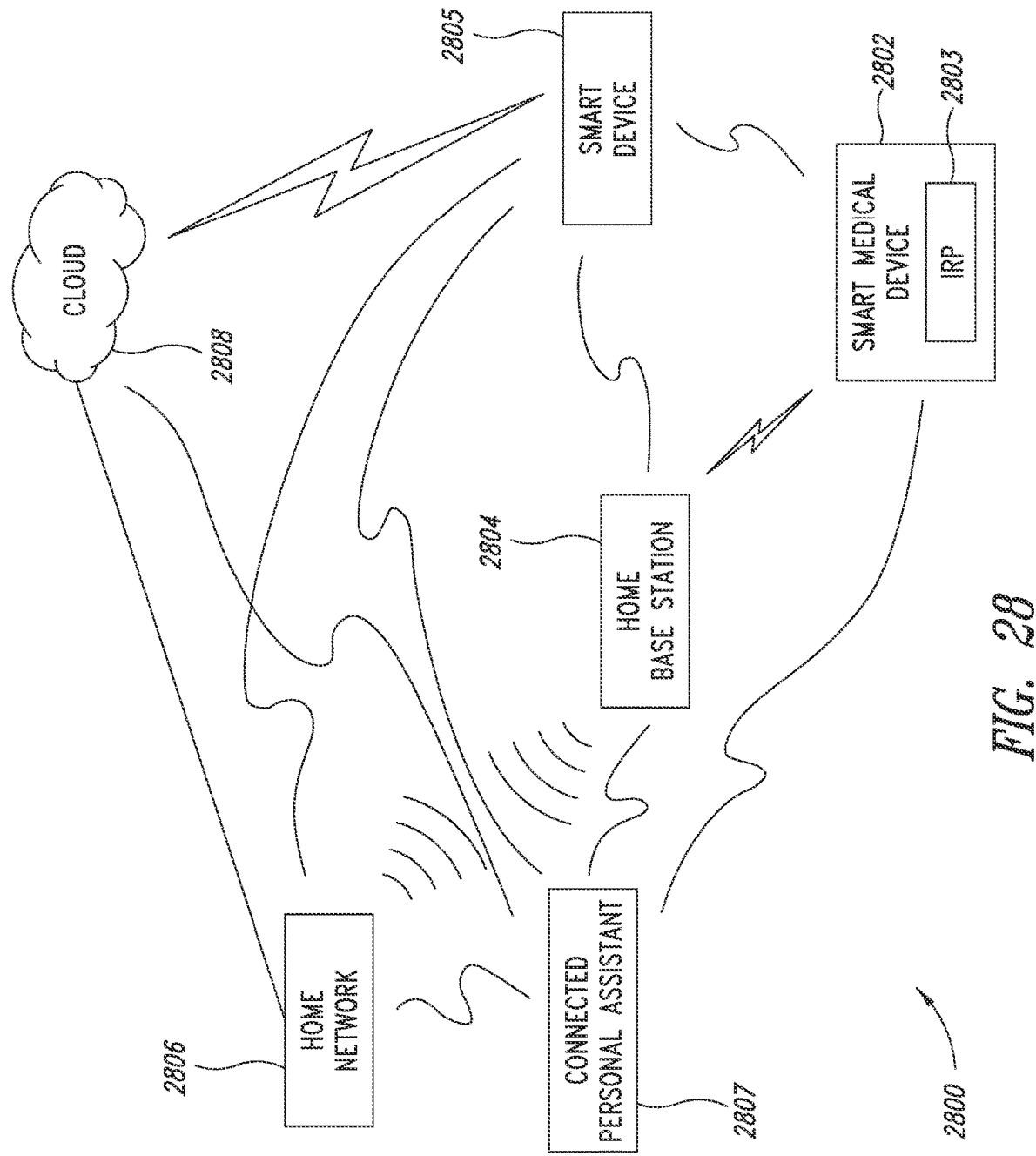
FIG. 28 is a context diagram of a smart medical device in a patient's home.

FIG. 28 illustrates a context diagram of a smart medical device environment 2800 including features present in the patient's home. In the environment, a smart medical device 2802 comprising an implantable reporting processor (IRP) 2803 has been implanted into a patient (not shown). Taken together, the sensing capability and the associated electronics assembly of the smart medical device of the present disclosure may be referred to as an implantable reporting processor (IRP). The IRP is a component of the smart medical device of the present disclosure, where the smart medical device comprises the IRP. An antenna may or may not be a component of the IRP. Likewise, a power supply may not be a component of the IRP. The implantable reporting processor 2803 is arranged and configured to collect data including for example, medical and health data related to a patient which the device is associated, and operational data of the smart medical device 2802 itself. The smart medical device 2802 communicates with one or more home base stations 2804 or one or more external smart devices 2805 during different stages of monitoring the patient.

The smart medical device 2802 includes one or more sensors that collect information and data, including medical and health data related to a patient which the device is associated, and operational data of the medical device 2802 itself. The smart medical device 2802 collects data at various different times and at various different rates during a monitoring process of the patient, and may optionally store that data in a memory until it is transmitted outside the body of the patient. In some embodiments, the smart medical device 2802 may operate in a plurality of different phases over the course of monitoring the patient so that more data is collected soon after the smart medical device 2802 is implanted into the patient, but less data is collected as the patient heals and thereafter.

The amount and type of data collected by the smart medical device 2802 may be different from patient to patient, and the amount and type of data collected may change for a single patient. For example, a medical practitioner studying data collected by the smart medical device 2802 of a particular patient may adjust or otherwise control how the smart medical device 2802 collects future data.

The amount and type of data collected by a smart medical device 2802 may be different for different body parts, for different types of patient conditions, for different patient demographics, or for other differences. Alternatively, or in addition, the amount and type of data collected may change overtime based on other factors, such as how the patient is healing or feeling, how long the monitoring process is projected to last, how much power remains in the smart medical device 2802 and should be conserved, the type of movement being monitored, the body part being monitored, and the like. In some cases, the collected data is supplemented with personally descriptive information provided by the patient such as subjective pain data, quality of life metric data, co-morbidities, perceptions or expectations that the patient associates with the smart medical device 2802, or the like.

Once the smart medical device 2802 is implanted into the patient and the patient returns home, the smart medical device may begin communications outside of the patient's body, within the home environment. The communication may be with, e.g., the home base station 2804, the external smart device 2805 (e.g., the patient's smart phone), the connected personal assistant 2807, or two or more of the home base station, and the external smart device, and the connected personal assistant can communicate with the smart medical device 2802. The smart medical device 2802 can collect data at determined rates and times, variable rates and times, or otherwise controllable rates and times. Data collection can start when the smart medical device 2802 is initialized in the operating room, when directed by a medical practitioner, or at some later point in time.

At least some data collected by the smart medical device 2802 may be transmitted to the home base station 2804 directly, to the external smart device 2805 directly, to the connected personal assistant 2807 directly, to the base station via one or both of the smart device and the connected personal assistant, to the smart device via one or both of the base station and the connected personal assistant, or to the connected personal assistant via one or both of the smart device and the base station. Here, "one or both" means via an item alone, and via both items serially or in parallel. For example, data collected by the implanted smart medical device 2802 may be transmitted to the home base station 2804 via the external smart device 2805 alone, via the connected personal assistant 2807 alone, serially via the external smart device and the connected personal assistant, serially via the connected personal assistant and the external smart device, and directly, and possibly contemporaneously, via both the external smart device and the connected personal assistant.

Similarly, data collected by the implanted smart medical device 2802 may be transmitted to the external smart device 2805 via the home base station 2804 alone, via the connected personal assistant 2807 alone, serially via the home base station and the connected personal assistant, serially via the connected personal assistant and the home base station, and directly, and possibly contemporaneously, via both the home base station and the connected personal assistant. Further in example, data collected by the implanted smart medical device 2802 may be transmitted to the connected personal assistant 2807 via the external smart device 2805 alone, via the home base station 2804 alone, serially via the external smart device and the home base station, serially via the home base station and the external smart device, and directly, and possibly contemporaneously, via both the external smart device and the home base station.

In various embodiments, one or more of the home base station 2804, the external smart device 2805, and the connected personal assistant 2807 pings the implanted smart medical device 2802 at periodic, predetermined, or other times to determine if the implanted smart medical device 2802 is within communication range of one or more of the home base station, the external smart device, and the connected personal assistant. Based on a response from the implanted smart medical device 2802, one or more of the home base station 2804, the external smart device 2805, and the connected personal assistant 2807 determines that the implanted smart medical device 2802 is within communication range, and the implanted smart medical device 2802 can be requested, commanded, or otherwise directed to transmit the data it has collected to one or more of the home base station 2804, the external smart device 2805, and the connected personal assistant 2807.

Each of one or more of the home base station 2804, the external smart device 2805, and the connected personal assistant 2807 may, in some cases, be arranged with a respective optional user interface. The user interface may be formed as a multimedia interface that unidirectionally or bi-directionally passes one or more types of multimedia information (e.g., video, audio, tactile, etc.). Via the respective user interface of one or more of the home base station 2804, the external smart device 2805, and the connected personal assistant 2807, the patient (not shown in FIG. 28) or an associate (not shown in FIG. 28) of the patient may enter other data to supplement the data collected by the implanted smart medical device 2802. A user, for example, may enter personally descriptive information (e.g., age change, weight change), changes in medical condition, co-morbidities, pain levels, quality of life, an indication of how the implanted smart medical device 2802 "feels," or other subjective metric data, personal messages for a medical practitioner, and the like. In these embodiments, the personally descriptive information may be entered with a keyboard, mouse, touch-screen, microphone, wired or wireless computing interface, or some other input means. In cases where the personally descriptive information is collected, the personally descriptive information may include, or otherwise be associated with, one or more identifiers that associate the information with unique identifier of the implanted smart medical device 2802, the patient, an associated medical practitioner, an associated medical facility, or the like.

In some of these cases, a respective optional user interface of each of one or more of the home base station 2804, the external smart device 2805, and the connected personal assistant 2807 may also be arranged to deliver information associated with the implanted smart medical device 2802 to the user from, for example, a medical practitioner. In these cases, the information delivered to the user may be delivered via a video screen, an audio output device, a tactile transducer, a wired or wireless computing interface, or some other like means.

In embodiments where one or more of the home base station 2804, the external smart device 2805, and the connected personal assistant 2807 are arranged with a user interface, which may be formed with an internal user interface arranged for communicative coupling to a patient portal device. The patent portal device may be smartphone, a tablet, a body-worn device, a weight or other health measurement device (e.g., thermometer, bathroom scale, etc.), or some other computing device capable of wired or wireless communication. In these cases, the user is able to enter the personally descriptive information, and the user also may be able to receive information associated with the implanted smart medical device 2802.

The home base station 2804 utilizes a home network 2806 of the patient to transmit the collected data to cloud 2808. The home network 2806, which may be a local area network, provides access from the home of the patient to a wide area network, such as the internet. In some embodiments, the home base station 2804 may utilize a Wi-Fi connection to connect to the home network 2806 and access the internet. In other embodiments, the home base station 2804 may be connected to a home computer (not shown in FIG. 28) of the patient, such as via a USB connection, which itself is connected to the home network 2806.

The external smart device 2805 can communicate with the implanted smart medical device 2802 directly via, for example, Blue Tooth® compatible signals, and can utilize the home network 2806 of the patient to transmit the collected data to cloud 2808, or can communicate directly with the cloud, for example, via a cellular network. Alternatively, the external smart device 2805 is configured to communicate directly with one or both of the home base station 2804 and the connected personal assistant 2807 via, for example, Blue Tooth® compatible signals, and is not configured to communicate directly with the implanted smart medical device 2802.

Furthermore, the connected personal assistant 2807 can communicate with the implanted smart medical device 2802 directly via, for example, Blue Tooth® compatible signals, and can utilize the home network 2806 of the patient to transmit the collected data to cloud 2808, or can communicate directly with the cloud, for example, via a modem/internet connection or a cellular network. Alternatively, the connected personal assistant 2807 is configured to communicate directly with one or both of the home base station 2804 and the external smart device 2805 via, for example, Blue Tooth® compatible signals, and is not configured to communicate directly with the implanted smart medical device 2802.

Along with transmitting collected data to the cloud 2808, one or more of the home base station 2804, the external smart device 2805, and the connected personal assistant 2807 may also obtain data, commands, or other information from the cloud 2808 directly or via the home network 2806. One or more of the home base station 2804, the external smart device 2805, and the connected personal assistant 2807 may provide some or all of the received data, commands, or other information to the implanted smart medical device 2802. Examples of such information include, but are not limited to, updated configuration information, diagnostic requests to determine if the implanted smart medical device 2802 is functioning properly, data collection requests, and other information.

The cloud 2808 may include one or more server computers or databases to aggregate data collected from the implanted smart medical device 2802, and in some cases personally descriptive information collected from a patient (not shown in FIG. 28), with data collected from other assemblies (not illustrated), and in some cases personally descriptive information collected from other patients. In this way, the cloud 2808 can create a variety of different metrics regarding collected data from each of a plurality of assemblies that are implanted into separate patients. This information can be helpful in determining if the assemblies are functioning properly. The collected information may also be helpful for other purposes, such as determining which specific devices may not be functioning properly, determining if a procedure or condition associated with the smart medical device is helping the patient (e.g., if the knee replacement is operating properly and reducing the patient's pain), and determining other medical information.

Still referring to FIG. 28, alternate embodiments are contemplated. For example, one or two of the home base station 2804, the external smart device 2805, and the connected personal assistant 2807 may be omitted from the smart medical device environment 2800. Furthermore, each of the home base station 2804, the external smart device 2805, and the connected personal assistant 2807 may be configured to communicate with one or both of the implanted smart medical device 2802 and the cloud 2808 via another one or two of the base station, the smart device, and the connected personal assistant. Moreover, the external smart device 2805 can be temporarily contracted as an interface to the implanted smart medical device 2802, and can be any suitable device other than a smart phone, such as a smart watch, a smart patch, and any IoT device, such as a coffee pot, capable of acting as an interface to the implanted smart medical device 2802.

In addition, one or more of the home base station 2804, external smart device 2805, and connected personal assistant 2807 can act as a communication hub for multiple prostheses implanted in one or more patients. Furthermore, one or more of the home base station 2804, external smart device 2805, and connected personal assistant 2807 can automatically order or reorder prescriptions or medical supplies (e.g., a knee brace) in response to patient input or implantable-prosthesis input (e.g., pain level, instability level) if a medical professional and insurance company have preauthorized such an order or reorder; alternatively, one or more of the base station, smart device, and connected personal assistant can be configured to request, from a medical professional or an insurance company, authorization to place the order or reorder. Moreover, one or more of the home base station 2804, external smart device 2805, and connected personal assistant 2807 can be configured with a personal assistant such as Alexa® or Siri®.

Although the smart medical device environment has been described in the context of a patient's home by reference to FIG. 28, the same principles apply when the environment is an operating room or a doctor's office. For example, in association with a medical procedure, a implanted smart medical device 2802 may be implanted in the patient's body within an operating room environment. Coetaneous with the medical procedure, the implanted smart medical device 2802 communicates with an operating room base station (analogous to the home base station). Subsequently, after sufficient recovery from the medical procedure, the patient returns home wherein the implanted smart medical device 2802 is arranged to communicate with a home base station 2804. Thereafter, at other times, the implanted smart medical device 2802 is arranged to communicate with a doctor office base station when the patient visits the doctor for a follow-up consultation. In any case, the implanted smart medical device 2802 communicates with each base station via a short range network protocol, such as the medical implant communication service (MICS), the medical device radio communications service (MedRadio), or some other wireless communication protocol suitable for use with the smart medical device 2802.

For example, implantation of the implanted smart medical device 2802 into the patient may occur in an operating room. As used herein, operating room includes any office, room, building, or facility where the smart medical device 2802 is implanted into the patient. For example, the operating room may be a typical operating room in a hospital, an operating room in a surgical clinic or a doctor's office, or any other operating theater where the smart medical device 2802 is implanted into the patient.

The operating room base station (analogous to the home base station of FIG. 28) is utilized to configure and initialize the implanted smart medical device 2802 in association with the smart medical device 2802 being implanted into the patient. A communicative relationship is formed between the smart medical device 2802 and the operating room base station, for example, based on a polling signal transmitted by the operating room base station and a response signal transmitted by the smart medical device 2802.

Upon forming a communicative relationship, which will often occur prior to implantation of the smart medical device 2802, the operating room base station transmits initial configuration information to the smart medical device 2802. This initial configuration information may include, but is not limited to, a time stamp, a day stamp, an identification of the type and placement of the smart medical device 2802, information on other implants associated with the smart medical device, surgeon information, patient identification, operating room information, and the like.

In some embodiments, the initial configuration information is passed unidirectionally; in other embodiments, initial configuration is passed bidirectionally. The initial configuration information may define at least one parameter associated with the collection of data by the smart medical device 2802. For example, the configuration information may identify settings for one or more sensors on the smart medical device 2802 for each of one or more modes of operation. The configuration information may also include other control information, such as an initial mode of operation of the smart medical device 2802, a particular event that triggers a change in the mode of operation, radio settings, data collection information (e.g., how often the smart medical device 2802 wakes up to collected data, how long it collects data, how much data to collect), home base station 2804, smart device 2805, and connected personal assistant 2807 identification information, and other control information associated with the implantation or operation of the smart medical device 2802. Examples of the connected personal assistant 2807, which also can be called a smart speaker, include Amazon Echo®, Amazon Dot®, Google Home®, Philips® patient monitor, Comcast's health-tracking speaker, and Apple HomePod®.

In some embodiments, the configuration information may be pre-stored on the operating room base station or an associated computing device. In other embodiments, a surgeon, surgical technician, or some other medical practitioner may input the control information and other parameters to the operating room base station for transmission to the smart medical device 2802. In at least one such embodiment, the operating room base station may communicate with an operating room configuration computing device. The operating room configuration computing device includes an application with a graphical user interface that enables the medical practitioner to input configuration information for the smart medical device 2802. In various embodiments, the application executing on the operating room configuration computing device may have some of the configuration information predefined, which may or may not be adjustable by the medical practitioner.

The operating room configuration computing device communicates the configuration information to the operating room base station via a wired or wireless network connection (e.g., via a USB connection, Bluetooth connection, Bluetooth Low Energy (BTLE) connection, or Wi-Fi connection), which in turn communicates it to the smart medical device 2802.

The operating room configuration computing device may also display information regarding the smart medical device 2802 or the operating room base station to the surgeon, surgical technician, or other medical practitioner. For example, the operating room configuration computing device may display error information if the smart medical device 2802 is unable to store or access the configuration information, if the smart medical device 2802 is unresponsive, if the smart medical device 2802 identifies an issue with one of the sensors or radio during an initial self-test, if the operating room base station is unresponsive or malfunctions, or for other reasons.

Although the operating room base station and the operating room configuration computing device are described as separate devices, embodiments are not so limited; rather, the functionality of the operating room configuration computing device and the operating room base station may be included in a single computing device or in separate devices as illustrated. In this way, the medical practitioner may be enabled in one embodiment to input the configuration information directly into the operating room base station.

After the smart medical device has been implanted in the patient, the patient may periodically visit a doctor's office for follow-up evaluation. In one aspect, the present disclosure provides a doctor's office environment (analogous to the home environment described herein) wherein the implanted smart medical device communicates with the office environment. During these visits, the data that has been stored in memory may be accessed, and/or specific data may be requested and obtained as part of a monitoring process.

For example, at various times throughout the monitoring process, the patient may be requested to visit a medical practitioner for follow up appointments. This medical practitioner may be the surgeon who implanted the smart medical device 2802 in the patient or a different medical practitioner that supervises the monitoring process, physical therapy, and recovery of the patient. For a variety of different reasons, the medical practitioner may want to collect real-time data from the smart medical device 2802 in a controlled environment. In some cases, the request to visit the medical practitioner may be delivered through a respective optional bidirectional user interface of each of one or more of the home base station 2804, the external smart device 2805, and the connected personal assistant 2807.

A medical practitioner utilizes the doctor office base station (analogous to the home base station shown in FIG. 28), which communicates with the smart medical device 2802, to pass additional data between the doctor office base station and the smart medical device 2802. Alternatively, or in addition, the medical practitioner utilizes the doctor office base station (not shown in FIG. 28) to pass commands to the smart medical device 2802. In some embodiments, the doctor office base station instructs the smart medical device 2802 to enter a high-resolution mode to temporarily increase the rate or type of data that is collected for a short time. The high-resolution mode directs the smart medical device 2802 to collect different (e.g., large) amounts of data during an activity where the medical practitioner is also monitoring the patient.

In some embodiments, the doctor office base station enables the medical practitioner to input event or pain markers, which can be synchronized with the high-resolution data collected by the smart medical device 2802. For example, the medical practitioner can have the patient walk on a treadmill while the smart medical device 2802 is in the high-resolution mode. As the patient walks, the patient may complain about pain. The medical practitioner can click a pain marker button on the doctor office base station to indicate the patient's discomfort. The doctor office base station records the marker and the time at which the marker was input. When the timing of this marker is synchronized with the timing of the collected high-resolution data, the medical practitioner can analyze the data to try and determine the cause of the pain.

In other embodiments, the doctor office base station may provide updated configuration information to the smart medical device 2802. The smart medical device 2802 can store this updated configuration information, which can be used to adjust the parameters associated with the collection of the data. For example, if the patient is doing well, the medical practitioner can direct a reduction in the frequency at which the smart medical device 2802 collects data. On the contrary, if the patient is experiencing an unexpected amount of pain, the medical practitioner may direct the smart medical device 2802 to collect additional data for a determined period of time (e.g., a few days). The medical practitioner may use the additional data to diagnose and treat a particular problem. In some cases, the additional data may include personally descriptive information provided by the patient after the patient has left presence of the medical practitioner and is no longer in range of the doctor office base station. In these cases, the personally descriptive information may be collected and delivered from via one or more of the home base station 2804, the external smart device 2805, and the connected personal assistant 2807. Firmware within the smart medical device and/or the base station will provide safeguards limiting the duration of such enhanced monitoring to ensure the smart medical device 2802 retains sufficient power to last for the implant's lifecycle.

In various embodiments, the doctor office base station may communicate with a doctor office configuration computing device (analogous to the operating room computing device). The doctor office configuration computing device includes an application with a graphical user interface that enables the medical practitioner to input commands and data. Some or all of the commands, data, and other information may be later transmitted to the smart medical device 2802 via the doctor office base station. For example, in some embodiments, the medical practitioner can use the graphical user interface to instruct the smart medical device 2802 to enter its high-resolution mode. In other embodiments, the medical practitioner can use graphical user interface to input or modify the configuration information for the smart medical device 2802. The doctor office configuration computing device transmits the information (e.g., commands, data, or other information) to the doctor office base station via a wired or wireless network connection (e.g., via a USB connection, Bluetooth connection, or Wi-Fi connection), which in turn transmits some or all of the information to the smart medical device 2802.

The doctor office configuration computing device may also display, to the medical practitioner, other information regarding the smart medical device 2802, regarding the patient (e.g., personally descriptive information), or the doctor office base station. For example, the doctor office configuration computing device may display the high-resolution data that is collected by the smart medical device 2802 and transmitted to the doctor office base station. The doctor office configuration computing device may also display error information if the smart medical device 2802 is unable to store or access the configuration information, if the smart medical device 2802 is unresponsive, if the smart medical device 2802 identifies an issue with one of the sensors or radio, if the doctor office base station is unresponsive or malfunctions, or for other reasons.

In some embodiments, doctor office configuration computing device may have access to the cloud 2808. In at least one embodiment, the medical practitioner can utilize the doctor office configuration computing device to access data stored in the cloud 2808, which was previously collected by the smart medical device 2802 and transmitted to the cloud 2808 via one or both of the home base station 2804 and external smart device 2805. Similarly, the doctor office configuration computing device can transmit the high-resolution data obtain from the smart medical device 2802 via the doctor office base station to the cloud 2808. In some embodiments, the doctor office base station may have internet access and may be enabled to transmit the high-resolution data directly to the cloud 2808 without the use of the doctor office configuration computing device.

In various embodiments, the medical practitioner may update the configuration information of the smart medical device 2802 when the patient is not in the medical practitioner's office. In these cases, the medical practitioner can utilize the doctor office configuration computing device (not shown in FIG. 28) to transmit updated configuration information to the smart medical device 2802 via the cloud 2808. One or more of the home base station 2804, the external smart device 2805, and the connected personal assistant 2807 can obtain updated configuration information from the cloud 2808 and pass updated configuration information to the cloud. This can allow the medical practitioner to remotely adjust the operation of the smart medical device 2802 without needing the patient to come to the medical practitioner's office. This may also permit the medical practitioner to send messages to the patient in response, for example, to personally descriptive information that was provided by the patient and passed through one or more of the home base station 2804, the external smart device 2805, and the connected personal assistant 2807 to the doctor office base station (not shown in FIG. 28). For example, if a patient speaks "I feel pain" into the connected personal assistant 2807, then the medical practitioner may issue a prescription for a pain reliever and cause the connected personal assistant to notify the patient by "speaking" "the doctor has called in a prescription for Vicodin® to your preferred pharmacy; the prescription will be ready for pick up at 4 pm."

Although the doctor office base station (not shown in FIG. 28) and the doctor office configuration computing device (not shown in FIG. 28) are described as separate devices, embodiments are not so limited; rather, the functionality of the doctor office configuration computing device and the doctor office base station may be included in a single computing device or in separate devices (as illustrated). In this way, the medical practitioner may be enabled in one embodiment to input the configuration information or markers directly into the doctor office base station and view the high-resolution data (and synchronized marker information) from a display on the doctor office base station.

Certain exemplary embodiments of the present disclosure, which are numbered for convenience of reference, include the following:

1. A medical device comprising:
    a structure having a lumen extending at least partially therethrough, and configured to be at least partially implanted in a body; and
    an electronics cartridge including electronics and configured to be inserted into the lumen after implant of the structure.
2. The medical device of embodiment 1, further comprising a sensor for measuring an electrical property of tissue, the sensor comprising:
    a plurality of electrodes; and
    a sensing module of the electronics cartridge, coupled to the plurality of electrodes.
3. The medical device of embodiment 2, wherein:
    the plurality of electrodes comprise a first electrode and a second electrode; and
    the sensing module is configured to enable the first electrode and the second electrode to function in either of an application mode during which a signal is applied across the electrodes, or a sensing mode during which an impedance between the electrodes is sensed.
4. The medical device of embodiment 3, wherein the sensing module comprises a signal generator configured to apply signals at different frequencies to measure tissue impedance in accordance with electrical impedance spectroscopy (EIS) techniques.
5. The medical device of embodiment 2, wherein:
    the sensor further comprises an electrode switch;
    the plurality of electrodes comprise a first electrode, a second electrode, a third electrode and a fourth electrode switchably coupled to the sensing module through the electrode switch; and
    the sensing module is configured to enable an application mode during which a signal is applied across the first electrode and the second electrode, and to enable a sensing mode during which an impedance between the third electrode and the fourth electrode is sensed.
6. The medical device of embodiment 5, wherein the sensing module comprises a signal generator configured to apply signals at different frequencies to measure tissue impedance in accordance with electrical impedance spectroscopy (EIS) techniques.
7. The medical device of embodiment 2, wherein the electrical property of tissue comprises impedance measurements, and further comprising a controller configured to process impedance measurements over time to determine a characterization of a bone fracture, the characterization corresponding to a healing state of the bone fracture.
8. The medical device of embodiment 7, wherein the healing state corresponds to one of union, likely non-union, and non-union.
9. The medical device of embodiment 2, wherein:
    the plurality of electrodes are associated with the structure and spaced apart to enable placement of a first electrode and a second electrode on opposite sides of a bone fracture; and
    the electronics cartridge comprises a plurality of electrical contacts located to electrically couple with the plurality of electrodes when the electronics cartridge is inserted into the lumen of the structure.
10. The medical device of embodiment 2, wherein:
    the plurality of electrodes are associated with the electronics cartridge and spaced apart to enable placement of a first electrode and a second electrode on opposite sides of a bone fracture.
11. The medical device of embodiment 10, wherein:
    the structure comprises at least one aperture through a sidewall; and
    the plurality of electrodes are positioned on the electronics cartridge to align with the at least one aperture when the electronics cartridge is inserted into the lumen of the structure.
12. The medical device of embodiment 10, wherein:
    the structure comprises a distal end opening and a proximal end opening; and
    the plurality of electrodes comprises a first electrode positioned on the electronics cartridge to be adjacent the distal end opening and a second electrode positioned on the electronics cartridge to be adjacent the proximal end opening when the electronics cartridge is inserted into the lumen of the structure.
13. The medical device of embodiment 10, wherein:
    the structure comprises a distal end opening; and
    the plurality of electrodes comprises a first electrode and a second electrode each positioned on the electronics cartridge to be located distal the distal end opening of the structure when the electronics cartridge is inserted into the lumen of the structure.
14. The medical device of any of embodiments 1-13, wherein the lumen is configured to receive an implant tool during implant of the structure.
15. The medical device of embodiment 14, wherein the structure comprises a head having a sunken pocket that define a head portion of the lumen that is configured to receive a part of the implant tool to enable a transfer of torque applied to the implant tool to the structure.
16. The medical device of any of embodiments 1-15, wherein the structure is configured to be implanted in a bone.
17. The medical device of embodiment 16, wherein the structure is configured to be implanted to bridge a fracture of the bone.
18. The medical device of embodiment 16, wherein the structure is configured to be implanted through a hole in a plate that bridges a fracture of the bone.
19. The medical device of any of embodiments 1-18, wherein the structure is a screw, pin, rod, nail, a part of a joint replacement implant, a part of a spinal fixation device, or a part of other orthopedic devices.
20. The medical device of any of embodiments 1-19, wherein the structure comprises a shaft having an outer diameter in a range of 4 millimeters or greater.

21. The medical device of any of embodiments 1-20, wherein the lumen comprises a shaft portion having a diameter sized to receive at least a portion of the electronics cartridge.

22. The medical device of any of embodiments 1-21, wherein each of the electronics cartridge and the lumen have a respective form factor that is generally the same.

23. The medical device of embodiment 22, wherein the respective form factors of the electronics cartridge and the lumen comprise a head portion and a shaft portion, wherein the head portion has a diameter greater than the shaft portion.

24. The medical device of any of embodiments 1-23, wherein the structure and the electronics cartridge comprise mechanical features that enable the electronics cartridge to be fixedly secured within the lumen.

25. The medical device of embodiment 24, wherein the mechanical features comprise one of: a difference in form factor between a head of the electronics cartridge and a head portion of the lumen of the structure; a projection associated with the electronics cartridge and a recess associated with the lumen of the structure; and an interlock feature associated with a shaft of the electronics cartridge for receiving an adhesive and an inner wall of the structure for engaging the adhesive.

26. The medical device of any of embodiments 1-25, wherein the structure and the electronics cartridge comprise mechanical features that enable the electronics cartridge to be removed from the lumen without damaging the structural integrity of either the electronics cartridge or the structure.

27. The medical device of embodiment 26, wherein the mechanical features comprise complementary screw threads.

28. The medical device of any of embodiments 1-27, wherein the electronics cartridge comprises a head and a shaft and at least a portion of electronics are included in an electronics assembly located in the head.

29. The medical device of any of embodiments 1-28, wherein the electronics cartridge comprises a head and a shaft and at least a portion of electronics are included in an electronics assembly located in the shaft.

30. The medical device of any of embodiments 1-29, wherein:
the structure comprises an exterior surface and one or more electrodes are at the exterior surface; and
the electronics cartridge comprises an exterior surface and one or more electrical contacts at the exterior surface configured to electrically couple to the one or more electrodes when the electronics cartridge is inserted into the lumen.

31. The medical device of embodiment 30, wherein the structure comprises an electrically conductive substrate, and the one or more electrodes corresponds to an electrically conductive material associated with a sidewall of the electrically conductive substrate and electrically isolated from the electrically conductive substrate by an electrically insulative material.

32. The medical device of embodiment 31, further comprising a feedthrough for each of the one or more electrodes, the feedthrough extending through the sidewall of the electrically conductive substrate and providing an electrical coupling between each of the one or more electrodes and an interior of the structure.

33. The medical device of embodiment 30, wherein the structure comprises an electrically conductive substrate at least partially coated with an electrically insulative material, and the one or more electrodes corresponds to one or more of:
an area of the electrically conductive substrate not coated by the electrically insulative material; and
an electrically conductive material overlying the electrically insulative material.

34. The medical device of embodiment 30, wherein the structure comprises a substrate and the one or more electrodes corresponds to an electrically conductive material on the substrate.

35. The medical device of embodiment 34, wherein the substrate is of an electrically non-conductive material.

36. The medical device of embodiment 34, wherein:
the substrate is of an electrically conductive material; and
the one or more electrodes corresponds to an electrically conductive material overlying an electrically insulative material.

37. The medical device of embodiment 30, wherein the structure comprises a proximal end, a distal end, and the one or more electrodes comprise one or more of: a distal electrode near the distal end, a proximal electrode near the proximal end, a plurality of distal electrodes near the distal end, a plurality of proximal electrodes near the proximal end, and a plurality of electrodes between the proximal end and the distal end.

38. The medical device of embodiment 30, wherein the one or more electrodes are electrically isolated from each other and from the structure.

39. The medical device of any of embodiments 1-38, wherein:
the structure comprises one or more apertures through a sidewall; and the electronics cartridge comprises one or more electrodes positioned to align with the one or more apertures when the electronics cartridge is inserted into the lumen of the structure.

40. The medical device of embodiment 39, wherein each of the structure and the electronics cartridge are configured to align each of the one or more electrodes with a corresponding one of the one or more apertures when the electronics cartridge is inserted into the lumen.

41. The medical device of embodiment 39, wherein the electronics cartridge comprises a proximal end, a distal end, and the one or more electrodes comprise one or more of: a distal electrode near the distal end, a proximal electrode near the proximal end, a plurality of distal electrodes near the distal end, a plurality of proximal electrodes near the proximal end, and a plurality of electrodes between the proximal end and the distal end.

42. The medical device of embodiment 39, wherein the one or more electrodes are electrically isolated from each other.

43. The medical device of embodiment 39, wherein:
the one or more apertures corresponds to a slot; and
the electronics cartridge comprises an electrode assembly that extends outward from a surface of the electronics cartridge, has a form factor that fits through the slot, and that includes the one or more electrodes.

44. The medical device of embodiment 43, wherein the electrode assembly is biased relative to the surface of the electronics cartridge to enable the electronics cartridge to transition between a compression state during which an outer surface of the electrode assembly is substantially flush with the surface of the electronics cartridge, and an expanded state during which the outer surface of the electrode assembly is elevated relative to the surface of the electronics cartridge to extend through the slot.

45. The medical device of embodiment 39, wherein the electrodes are associated with a shaft of the electronics cartridge and include an electrode surface that is recessed relative to a surface of the shaft such that when inserted into the lumen of the structure an empty space in communication with an aperture is formed between the electrode surface and an inner wall of the structure.

46. The medical device of any of embodiments 1-45, wherein:
the structure comprises a distal end opening and a proximal end opening; and
the electronics cartridge comprises a first electrode positioned to be adjacent the distal end opening and a second electrode positioned to be adjacent the proximal end opening when the electronics cartridge is inserted into the lumen of the structure.

47. The medical device of any of embodiments 1-46, wherein:
the structure comprises a distal end opening; and
the electronics cartridge comprises a plurality of electrodes positioned on the electronics cartridge to be located distal the distal end opening of the structure when the electronics cartridge is inserted into the lumen of the structure.

48. The medical device of any of embodiments 1-47, wherein the electronics comprises an antenna.

49. The medical device of embodiment 48, wherein:
the electronics cartridge comprises a proximal end, a distal end, a head at the proximal end, and a shaft extending from the head toward the distal end; and
the antenna is associated with the shaft.

50. The medical device of embodiment 49, wherein the antenna comprises a conductive wire or trace extending along a length of the shaft.

51. The medical device of embodiment 50, wherein the antenna extends in a helical pattern around the shaft.

52. The medical device of embodiment 51, wherein the antenna is electrically insulated from an outer surface of the shaft to avoid contact with the structure when the electronics cartridge is inserted into the lumen of the structure.

53. The medical device of embodiment 48, wherein:
the electronics cartridge comprises a proximal end, a distal end, a head at the proximal end, and a shaft extending from the head toward the distal end; and
the antenna is associated with the head.

54. The medical device of embodiment 53, wherein the antenna comprises a conductive wire or trace extending along a plane parallel with a base of the head.

55. The medical device of any of embodiments 1-55, wherein the electronics comprises one or more power sources.

56. The medical device of embodiment 55, wherein:
the electronics cartridge comprises a proximal end, a distal end, a head at the proximal end, and a shaft extending from the head toward the distal end; and
the one or more power sources is associated with the shaft.

57. The medical device of embodiment 55, wherein:
the electronics cartridge comprises a proximal end, a distal end, a head at the proximal end, and a shaft extending from the head toward the distal end; and
the one or more power sources is associated with the head.

58. The medical device of embodiment 55, wherein the one or more power sources comprises one or more of a battery and a capacitor.

59. The medical device of embodiment 55, wherein the one or more power sources comprises an energy harvesting device configured to harvest energy by one of electrostatic energy, wireless energy transfer, electromechanical conversion, electro-magnetic conversion, and IR radiation.

60. The medical device of any of embodiments 1-59, wherein the electronics comprises one or more communication components that enable communication between the medical device and another device that is either implanted in the body or external the body.

61. The medical device of embodiment 60, wherein the one or more communication components comprises:
an antenna; and
a radio frequency (RF) transceiver coupled to the antenna and configured to receive and transmit RF signals.

62. The medical device of embodiment 60, wherein the one or more communication components comprise:
a transmitter coupled to electrodes associated with the medical device and configured and located to be placed in contact with tissue; and
a receiver coupled to electrodes associated with the medical device and configured and located to be placed in contact with tissue.

63. The medical device of embodiment 60, wherein the one or more communication components are configured to at least one of:
enable capacitive coupling between the medical device and the other device; or to enable galvanic coupling between the medical device and the other device.

64. The medical device of any of embodiments 1-63, wherein the electronics comprises one or more sensors.

65. The medical device of embodiment 64, wherein the one or more sensors comprises an accelerometer configured to output a signal corresponding to motion of the structure.

66. The medical device of embodiment 65, wherein the accelerometer comprises one of a one-dimensional accelerometer and a three-dimensional accelerometer.

67. The medical device of embodiment 65, wherein the electronics further comprise a processor coupled to the accelerometer to receive the signal and configured to process the signal to provide an indication of one or more of patient activity, integrity of the structure, and movement of the structure relative to implant location.

68. The medical device of embodiment 64, wherein the one or more sensors comprises a temperature sensor configured to output a signal corresponding to a temperature of the structure at an implant location.

69. The medical device of embodiment 64, wherein the one or more sensors comprise a strain sensor configured to output a signal corresponding to motion, force, tension, velocity, or other mechanical forces associated with the structure.

70. The medical device of embodiment 69, wherein the electronics further comprise a processor coupled to the strain sensor to receive signals from the strain sensor overtime and configured to process the signals to provide a characterization of a bone fracture, the characterization corresponding to a healing state of the bone fracture.

71. The medical device of embodiment 64, wherein the one or more sensors comprise an ultrasonic transducer configured to output a signal corresponding to ultrasound energy sensed in an area of the structure.
72. The medical device of embodiment 71, wherein the electronics further comprise a processor coupled to the ultrasonic transducer to receive signals from the ultrasonic transducer and configured to process the signals to provide one or more of a characterization of a bone fracture, a characterization of tissue in the area of the structure, healing area glucose.
73. The medical device of embodiment 64, wherein the one or more sensors comprise one or more of a glucose detector and an oxygen sensor configured to output a signal corresponding to a respective one of glucose level and oxygen level.
74. The medical device of embodiment 73, wherein the electronics further comprise a processor coupled to the one or more of a glucose detector and an oxygen sensor to receive the signal and configured to process the signal to provide an indication of inflammation fluid in a region of the medical device.
75. The medical device of any of embodiments 1-74, wherein the electronics cartridge further comprises a mechanism configured to deliver a catalyst material that produces a gaseous oxygen reaction at an implant site by a chemical reaction.
76. The medical device of embodiment 75, wherein the mechanism comprises one or more of:
 a reservoir that releases the catalyst material at one or more times after implant under control of a time release controller; and
 a coating of catalyst material on the electronics cartridge.
77. A medical device comprising:
 a cannulated structure having a lumen extending therethrough, and a plurality of electrodes at an outer surface of the cannulated structure, the cannulated structure configured to be at least partially implanted in a body; and
 an electronics cartridge including electronics, the electronics cartridge configured to be inserted into the lumen, and to establish one or more electrical couplings between the electronics and the plurality of electrodes upon such insertion.
78. The medical device of embodiment 77, wherein the cannulated structure comprises a shaft and the plurality of electrodes comprise a single set of electrodes spaced apart along a length of the shaft.
79. The medical device of embodiment 77, wherein the cannulated structure comprises a shaft and the plurality of electrodes comprise a first set of electrodes spaced apart along a length of a first side of the shaft, and a second set of electrodes spaced apart along a length of a second side of spaced from the first side.
80. The medical device of embodiment 77, wherein the cannulated structure comprises a shaft and the plurality of electrodes comprise a first linear electrode at a first side of the shaft, and a second linear electrode at a second side of spaced from the first side.
81. The medical device of embodiment 77, wherein the cannulated structure comprises:
 an electrically conductive body having an exterior surface at least partially coated with an electrically insulative material,
 a first electrode of the plurality of electrodes corresponding to an exposed portion of the electrically conductive body, and
 a second electrode of the plurality of electrodes that overlies a portion of the electrically insulative material.
82. The medical device of embodiment 81, wherein the electronics cartridge comprises:
 a first electrical contact positioned to contact an inner surface of the electrically conductive body to thereby establish an electrical coupling between the electronics and the first electrode; and
 a second electrical contact positioned to contact a portion of the second electrode to thereby establish an electrical coupling between the electronics and the second electrode.
83. The medical device of embodiment 82, wherein the electronics cartridge further comprises an insulating seal between the first electrical contact and the second electrical contact.
84. The medical device of embodiment 82, wherein the second electrode is partially coated with an electrically insulative material, and the portion of the second electrode that contacts the second electrical contact corresponds to an uncoated portion of the second electrode.
85. The medical device of embodiment 84, wherein the uncoated portion of the second electrode is located in a head portion of the lumen at a proximal end of the cannulated structure.
86. The medical device of embodiment 77, wherein the cannulated structure comprises:
 a body having a head and an exterior surface at least partially coated with an electrically insulative material;
 a first portion of electrically conductive material on the electrically insulative material forming a first electrode of the plurality of electrodes, a first electrical contact near the head, and a first conductive path between the first electrode and the first electrical contact; and
 a second portion of electrically conductive material on the electrically insulative material forming a second electrode of the plurality of electrodes, a second electrical contact near the head, and a second conductive path between the second electrode and the second electrical contact.
87. The medical device of embodiment 86, wherein the electronics cartridge comprises:
 a first electrical contact positioned to contact the first electrical contact of the cannulated structure to thereby establish an electrical coupling between the electronics and the first electrode; and
 a second electrical contact positioned to contact the second electrical contact of the cannulated structure to thereby establish an electrical coupling between the electronics and the second electrode.
88. The medical device of embodiment 77, wherein the cannulated structure comprises:
 a distal piece that includes a first electrode of the plurality of electrodes; and
 a proximal piece that includes a second electrode of the plurality of electrodes.
89. The medical device of embodiment 88, wherein each of the distal piece and the proximal piece comprise an electrically conductive substrate with an exterior surface that is at least partially coated with an electrically insulative coating.
90. The medical device of embodiment 88, wherein the each of the distal piece and the proximal piece comprise a mechanical feature that enables a mechanical coupling between the distal piece and the proximal piece.

91. The medical device of embodiment 77, wherein the cannulated structure and the electronics cartridge comprise mechanical features that enable the electronics cartridge to be fixedly secured within the lumen.

92. The medical device of embodiment 91, wherein the mechanical features comprise one of: a difference in form factor between a head of the electronics cartridge and a head portion of the lumen of the cannulated structure; a projection associated with the electronics cartridge and a recess associated with the lumen of the cannulated structure; and an interlock feature associated with a shaft of the electronics cartridge for receiving an adhesive and an inner wall of the cannulated structure for engaging the adhesive.

93. The medical device of embodiment 77, wherein the cannulated structure and the electronics cartridge comprise mechanical features that enable the electronics cartridge to be removed from the lumen without damaging the structural integrity of either the electronics cartridge or the cannulated structure.

94. The medical device of embodiment 93, wherein the mechanical features comprise complementary screw threads.

95. A medical device comprising:
a cannulated structure having a lumen extending therethrough and at least one aperture through a sidewall of the cannulated structure, the cannulated structure configured to be at least partially implanted in a body; and
an electronics cartridge including a plurality of electrodes and electronics electrically coupled to the electrodes, the electronics cartridge configured to be inserted into the lumen, and to provide alignment between the plurality of electrodes and the at least one aperture upon such insertion.

96. The medical device of embodiment 95, wherein:
the at least one aperture corresponds to a slot; and
the electronics cartridge comprises an electrode assembly that extends outward from a surface of the electronics cartridge, has a form factor that fits through the slot, and includes the plurality of electrodes.

97. The medical device of embodiment 96, wherein the electrode assembly is biased relative to the surface of the electronics cartridge to enable the electronics cartridge to transition between a compression state during which an outer surface of the electrode assembly is substantially flush with the surface of the electronics cartridge, and an expanded state during which the outer surface of the electrode assembly is elevated relative to the surface of the electronics cartridge to extend through the slot.

98. The medical device of embodiment 95, wherein:
the at least one aperture corresponds to a plurality of apertures; and
the electronics cartridge comprises a corresponding plurality of electrodes.

99. The medical device of embodiment 98, wherein the plurality of electrodes are ring electrodes recessed relative to a surface of the electronics cartridge such that when inserted into the lumen of the cannulated structure an annular space in communication with an aperture is formed between an electrode surface and an inner wall of the cannulated structure.

100. The medical device of embodiment 98, wherein the plurality of electrodes comprise a distal electrode and a proximal electrode.

101. The medical device of embodiment 98, wherein the plurality of electrodes comprise more than two electrodes arrange in an array between a distal electrode and a proximal electrode 102. A medical device comprising:
a cannulated structure having a lumen extending therethrough, and a distal end opening and a proximal end opening, the cannulated structure configured to be at least partially implanted in a body; and
an electronics cartridge including a plurality of electrodes and electronics electrically coupled to the electrodes, the electronics cartridge configured to be inserted into the lumen, and to position a first electrode of the plurality of electrodes at the distal end opening and a second electrode of the plurality of electrodes at the proximal end opening upon such insertion.

103. The medical device of embodiment 102, wherein the first electrode is a ring electrode recessed relative to a surface of the electronics cartridge such that when inserted into the lumen an annular space in communication with the distal end opening is formed between a surface of the first electrode and an inner wall of the cannulated structure.

104. The medical device of embodiment 102, wherein the cannulated structure comprises a head having an outer perimeter and the second electrode extends out from the electronics cartridge and beyond the outer perimeter.

105. A medical device comprising:
a cannulated structure having a lumen extending therethrough, and a distal end opening and a proximal end opening, the cannulated structure configured to be at least partially implanted in a body; and
an electronics cartridge including a plurality of electrodes and electronics electrically coupled to the electrodes, the electronics cartridge configured to be inserted into the lumen, and to position the plurality of electrodes distal the distal end opening upon such insertion.

106. The medical device of embodiment 105, wherein the electronics cartridge comprises a shaft having a length, and at least two portions of different rigidity along the length.

107. The medical device of embodiment 106, wherein the plurality of electrodes are associated with a less rigid portion of the at least two portions.

108. The medical device of embodiment 106, wherein the electronics are associated with a more rigid portion of the at least two portions.

109. A medical device configured to be at least partially implanted in a body, the medical device comprising:
a structure having a head and a shaft, each respectively defining a head cavity and a shaft cavity;
electronics located in one or more of the head cavity and the shaft cavity; and
at least one electrode associated with the shaft and electrically coupled to the electronics.

110. The medical device of embodiment 109, wherein the structure comprises a shaft and the at least one electrode comprises a single set of electrodes spaced apart along a length of the shaft.

111. The medical device of embodiment 109, wherein the structure comprises a shaft and the at least one electrode comprises a first set of electrodes spaced apart along a length of a first side of the shaft, and a second set of electrodes spaced apart along a length of a second side of spaced from the first side.

112. The medical device of embodiment 109, wherein the structure comprises a shaft and the at least one electrode comprises a first linear electrode at a first side of the shaft, and a second linear electrode at a second side of spaced from the first side.

113. The medical device of embodiment 109, further comprising a sensor for measuring an electrical property of tissue, the sensor comprising:
a plurality of electrodes; and
a sensing module coupled to the plurality of electrodes.

114. The medical device of embodiment 113, wherein:
the plurality of electrodes comprise a first electrode and a second electrode; and
the sensing module is configured to enable the first electrode and the second electrode to function in either of an application mode during which a signal is applied across the electrodes, or a sensing mode during which an impedance between the electrodes is sensed.

115. The medical device of embodiment 114, wherein the sensing module comprises a signal generator configured to apply signals at different frequencies to measure tissue impedance in accordance with electrical impedance spectroscopy (EIS) techniques.

116. The medical device of embodiment 113, wherein:
the sensor further comprises an electrode switch;
the plurality of electrodes comprise a first electrode, a second electrode, a third electrode and a fourth electrode switchably coupled to the sensing module through the electrode switch; and
the sensing module is configured to enable an application mode during which a signal is applied across the first electrode and the second electrode, and to enable a sensing mode during which an impedance between the third electrode and the fourth electrode is sensed.

117. The medical device of embodiment 116, wherein the sensing module comprises a signal generator configured to apply signals at different frequencies to measure tissue impedance in accordance with electrical impedance spectroscopy (EIS) techniques.

118. The medical device of embodiment 113, wherein the electrical property of tissue comprises impedance measurements, and further comprising a controller configured to process impedance measurements overtime to determine a characterization of a bone fracture, the characterization corresponding to a healing state of the bone fracture.

119. The medical device of embodiment 118, wherein the healing state corresponds to one of union, likely non-union, and non-union.

120. The medical device of embodiment 109, wherein the structure is configured to be implanted in a bone.

121. The medical device of embodiment 120, wherein the structure is configured to be implanted to bridge a fracture of the bone.

122. The medical device of embodiment 120, wherein the structure is configured to be implanted through a hole in a plate that bridges a fracture of the bone.

123. The medical device of embodiment 109, wherein the structure is a screw, pin, rod, nail, a part of a joint replacement implant, a part of a spinal fixation device, or a part of other orthopedic devices.

124. The medical device of embodiment 109, wherein the structure comprises a shaft having an outer diameter in a range of 4 millimeters or greater.

125. The medical device of embodiment 109, wherein:
the structure comprises an exterior surface and one or more electrodes at the exterior surface that electrically couple to the electronics.

126. The medical device of embodiment 125, wherein the structure comprises a substrate, and the one or more electrodes corresponds to an electrically conductive structure extending from the exterior surface along a sidewall of the substrate to the electronics.

127. The medical device of embodiment 125, wherein the structure comprises a substrate, and the one or more electrodes corresponds to an electrically conductive structure extending through an aperture through a sidewall of the substrate.

128. The medical device of embodiment 127, wherein the electrically conductive structure comprises a layer of electrically conductive material that extends from an exterior surface of the structure, along a sidewall of the aperture, to an inner surface of the structure.

129. The medical device of embodiment 127, wherein the electrically conductive structure comprises a conductive pin extending through the aperture.

130. The medical device of embodiment 129, wherein the conductive pin is a pogo style pin that is normally biased outward from the aperture.

131. The medical device of embodiment 129, wherein the electrically conductive structure comprises a conductive material that fills the aperture.

132. The medical device of embodiment 129, wherein the substrate is of an electrically conductive material that is at least partially coated with an electrically insulative material.

133. The medical device of embodiment 132, wherein the aperture has a sidewall that is coated with an electrically insulative material.

134. The medical device of embodiment 129, wherein the substrate is of an electrically non-conductive material.

135. The medical device of embodiment 125, wherein the structure comprises a proximal end, a distal end, and the one or more electrodes comprise one or more of: a distal electrode near the distal end, a proximal electrode near the proximal end, a plurality of distal electrodes near the distal end, a plurality of proximal electrodes near the proximal end, and a plurality of electrodes between the proximal end and the distal end.

136. The medical device of embodiment 135, wherein the one or more electrodes are electrically isolated from each other.

137. The medical device of embodiment 109, wherein the electronics comprises an antenna.

138. The medical device of embodiment 137, wherein the antenna is associated with the shaft of the structure.

139. The medical device of embodiment 138, wherein the antenna comprises a conductive wire or trace extending along a length of the shaft.

140. The medical device of embodiment 139, wherein the antenna extends in a helical pattern around the shaft.

141. The medical device of embodiment 138, wherein the antenna is associated with the head of the structure.

142. The medical device of embodiment 141, wherein the antenna comprises a conductive wire or trace extending along a plane parallel with a base of the head.

143. The medical device of embodiment 109, wherein the electronics comprises one or more power sources.

144. The medical device of embodiment 143, wherein the one or more power sources is associated with the shaft of the structure.
145. The medical device of embodiment 143, wherein the one or more power sources is associated with the head of the structure.
146. The medical device of embodiment 143, wherein the one or more power sources comprises one or more of a battery and a capacitor.
147. The medical device of embodiment 143, wherein the one or more power sources comprises an energy harvesting device configured to harvest energy by one of electrostatic energy, wireless energy transfer, electro-mechanical conversion, electro-magnetic conversion, and IR radiation.
148. The medical device of embodiment 109, wherein the electronics comprises one or more communication components that enable communication between the medical device and another device either implanted in the body or external the body.
149. The medical device of embodiment 148, wherein the one or more communication components comprises:
an antenna; and
a radio frequency (RF) transceiver coupled to the antenna and configured to receive and transmit RF signals.
150. The medical device of embodiment 148, wherein the one or more communication components comprise:
a transmitter coupled to electrodes associated with the medical device and configured and located to be placed in contact with tissue; and
a receiver coupled to electrodes associated with the medical device and configured and located to be placed in contact with tissue.
151. The medical device of embodiment 150, wherein the one or more communication components are configured to at least one of:
enable capacitive coupling between the medical device and the other device; or to enable galvanic coupling between the medical device and the other device.
152. The medical device of embodiment 109, wherein the electronics comprises one or more sensors.
153. The medical device of embodiment 152, wherein the one or more sensors comprises an accelerometer configured to output a signal corresponding to motion of the structure.
154. The medical device of embodiment 153, wherein the accelerometer comprises one of a one-dimensional accelerometer and a three-dimensional accelerometer.
155. The medical device of embodiment 153, wherein the electronics further comprise a processor coupled to the accelerometer to receive the signal and configured to process the signal to provide an indication of one or more of patient activity, integrity of the structure, and movement of the structure relative to implant location.
156. The medical device of embodiment 152, wherein the one or more sensors comprises a temperature sensor configured to output a signal corresponding to a temperature of the structure at an implant location.
157. The medical device of embodiment 152, wherein the one or more sensors comprise a strain sensor configured to output a signal corresponding to motion, force, tension, velocity, or other mechanical forces associated with the structure.
158. The medical device of embodiment 157, wherein the electronics further comprise a processor coupled to the strain sensor to receive signals from the strain sensor overtime and configured to process the signals to provide a characterization of a bone fracture, the characterization corresponding to a healing state of the bone fracture.
159. The medical device of embodiment 152, wherein the one or more sensors comprise an ultrasonic transducer configured to output a signal corresponding to ultrasound energy sensed in an area of the structure.
160. The medical device of embodiment 159, wherein the electronics further comprise a processor coupled to the ultrasonic transducer to receive signals from the ultrasonic transducer and configured to process the signals to provide one or more of a characterization of a bone fracture, a characterization of tissue in the area of the structure, and glucose level.
161. The medical device of embodiment 152, wherein the one or more sensors comprise one or more of a glucose detector and an oxygen sensor configured to output a signal corresponding to a respective one of glucose level and oxygen level.
162. The medical device of embodiment 161, wherein the electronics further comprise a processor coupled to the one or more of a glucose detector and an oxygen sensor to receive the signal and configured to process the signal to provide an indication of inflammation fluid in a region of the medical device.
163. The medical device of embodiment 109, further comprising a mechanism configured to deliver a catalyst material that produces a gaseous oxygen reaction at an implant site by a chemical reaction.
164. The medical device of embodiment 163, wherein the mechanism comprises one or more of:
a reservoir that releases the catalyst material at one or more times after implant under control of a time release controller; and
a coating of catalyst material on the structure.
165. A medical device comprising:
a cannulated structure having a lumen extending therethrough, a plurality of apertures through a sidewall, and a plurality of electrodes each associated with one of the plurality of apertures, the cannulated structure configured to be at least partially implanted in a body; and
an electronics cartridge including electronics, the electronics cartridge at least partially within the lumen, and comprising a plurality of electrical contacts each aligned with one of the apertures to establish an electrical coupling between the electronics and each of the plurality of electrodes.
166. The medical device of embodiment 165, wherein:
the cannulated structure comprises a shaft,
the plurality of apertures comprises a single set of apertures spaced apart along a length of the shaft, and
the plurality of electrodes comprises a single set of electrodes spaced apart along a length of the shaft.
167. The medical device of embodiment 165, wherein:
the cannulated structure comprises a shaft,
the plurality of apertures comprises a first set of apertures spaced apart along a length of a first side of the shaft, and a second set of apertures spaced apart along a length of a second side of spaced from the first side, and
the plurality of electrodes comprises a first set of electrodes spaced apart along a length of a first side of the shaft, and a second set of electrodes spaced apart along a length of a second side of spaced from the first side.
168. The medical device of embodiment 165, wherein:
the cannulated structure comprises a shaft,
the plurality of apertures comprises a first linear slot at a first side of the shaft, and a second linear slot at a second side of spaced from the first side, and
the plurality of electrodes comprises a first linear electrode at a first side of the shaft, and a second linear electrode at a second side of spaced from the first side.
169. The medical device of embodiment 165, wherein:
the cannulated structure comprises a substrate having an outer surface and an inner surface, and
the plurality of electrodes comprises:
a first electrode on the outer surface and having a feedthrough that extends through a first aperture of the plurality of apertures to the inner surface of the substrate, and
a second electrode on the outer surface and having a feedthrough that extends through a second aperture of the plurality of apertures to the inner surface of the substrate.
170. The medical device of embodiment 169, wherein the substrate comprises an electrically insulative material.
171. The medical device of embodiment 169, wherein the substrate comprises an electrically conductive material coated with an electrically insulative material.
172. The medical device of embodiment 169, wherein the electronics cartridge comprises:
a first electrical contact of the plurality of electrical contacts positioned to contact the feedthrough of the first electrode on the inner surface of the substrate to thereby establish an electrical coupling between the electronics and the first electrode; and
a second electrical contact of the plurality of electrical contacts positioned to contact the feedthrough of the second electrode on the inner surface of the substrate to thereby establish an electrical coupling between the electronics and the second electrode.
173. The medical device of embodiment 165, wherein the plurality of electrodes comprise:
a first conductive structure that extends through a first aperture of the plurality of apertures; and
a second conductive structure that extends through a second aperture of the plurality of apertures to an inner surface of the body.
174. The medical device of embodiment 173, wherein the first conductive structure corresponds to a first conductive pin and the second conductive structure corresponds to a second conductive pin.
175. The medical device of embodiment 174, wherein each of the first conductive pin and the second conductive pin is a pogo style pin that is normally biased outward from the first aperture or the second aperture.
176. The medical device of embodiment 173, wherein each of the first conductive structure and the second conductive structure corresponds to a conductive material that fills the first aperture or the second aperture.
177. An implantable medical device for characterizing a bone fracture in a bone, the medical device comprising:
an implant configured to be at least partially implanted in the bone and across the bone fracture;
an impedance sensor included in the implant and comprising:
a first electrode and a second electrode; and
a sensing module configured to obtain impedance measurements between the first electrode and the second electrode;
a controller and memory included in the implant and configured to process and store the impedance measurements; and
communication circuitry included in the implant and configured to transmit the impedance measurements to an external device.
178. The medical device of embodiment 177, wherein the sensing module is configured to enable the first electrode and the second electrode to function in either of an application mode during which a signal is applied across the first electrode and the second electrode, or a sensing mode during which an impedance between the first electrode and the second electrode is sensed.
179. The medical device of embodiment 178, wherein the sensing module comprises a signal generator configured to apply signals at different frequencies to measure tissue impedance in accordance with electrical impedance spectroscopy (EIS) techniques.
180. The medical device of embodiment 177, wherein:
the impedance sensor further comprises a third electrode and a fourth electrode; and
the sensing module is configured to enable an application mode during which a signal is applied across the first and second electrodes, and to enable a sensing mode during which an impedance between the third and fourth electrodes is sensed.
181. The medical device of embodiment 180, wherein the sensing module comprises a signal generator configured to apply signals at different frequencies to measure tissue impedance in accordance with electrical impedance spectroscopy (EIS) techniques.
182. The medical device of embodiment 177, wherein the controller is further configured to process impedance measurements overtime to determine a characterization of the bone fracture, the characterization corresponding to a healing state of the bone fracture.
183. The medical device of embodiment 182, wherein the healing state corresponds to one of union, likely non-union, and non-union.
184. The medical device of embodiment 177, wherein the first electrode and the second electrode are spaced apart on the implant to enable placement of the first electrode and the second electrode on opposite sides of the bone fracture.
185. The medical device of embodiment 177, wherein the impedance sensor comprises a plurality of electrodes including the first electrode, the second electrode and at least one additional electrode, wherein the sensing module is configured to select the first electrode and the second electrode from the plurality of electrodes based on impedance measurements such that the first electrode and the second electrode are on opposite sides of the bone fracture.
186. The medical device of embodiment 177, wherein the communication circuitry comprises tissue conductive communication circuitry coupled to the first electrode and the second electrode and configured to enable capacitive coupling between the medical device and another other device, or to enable galvanic coupling between the medical device and another device.
187. The medical device of embodiment 177, wherein the implant comprises:

a structure having a lumen extending at least partially therethrough, and configured to be at least partially implanted in the bone and across the bone fracture; and an electronics cartridge including at least a portion of the impedance sensor, the controller, the memory, and at least a portion of the communication circuitry, the electronics cartridge configured to be inserted into the lumen after implant of the structure.

188. The medical device of embodiment 187, wherein the structure comprises an exterior surface and the first electrode and the second electrode are at the exterior surface.

189. The medical device of embodiment 187, wherein:
the structure comprises at least one aperture through a sidewall; and
the electronics cartridge comprises an exterior surface and the first electrode and the second electrode are at the exterior surface and positioned to align with the at least one aperture when the electronics cartridge is inserted into the lumen of the structure.

190. The medical device of embodiment 187, wherein the structure is a screw, pin, rod, nail, a part of a joint replacement implant, a part of a spinal fixation device, or a part of other orthopedic devices.

191. The medical device of embodiment 177, wherein the implant comprises a single structure.

192. The medical device of embodiment 191, wherein the single structure is a screw, pin, rod, nail, a part of a joint replacement implant, a part of a spinal fixation device, or a part of other orthopedic devices.

193. A method of characterizing a bone fracture, the method comprising:
obtaining a plurality of measures of an electrical property of tissue overtime through a plurality of electrodes located in a boney tissue and across a bone fracture, the plurality of electrodes including a first electrode and a second electrode on opposite sides of the bone fracture; and
processing the measures to determine a characterization of a bone fracture, the characterization corresponding to a healing state of the bone fracture;
where optionally the plurality of measures is performed with a medical device according to any of embodiments 1-192, 226-238 and 262-263.

194. The method of embodiment 193, wherein the healing state corresponds to one of union, likely non-union, and non-union.

195. The method of embodiment 193, further comprising communicating the plurality of measures of an electrical property of tissue, or the characterization of a bone fracture to an external device.

196. The method of embodiment 193, wherein the electrical property of tissue comprises impedance, and obtaining a plurality of measures comprises:
applying signals at different frequencies to the first electrode to measure tissue impedance in accordance with electrical impedance spectroscopy (EIS) techniques.

197. The method of 196, wherein the signals are applied by an implanted sensing module.

198. The method of embodiment 193, further comprising implanting the plurality of electrodes to place the first electrode and the second electrode on opposite sides of the bone fracture.

199. The method of embodiment 198, wherein implanting the plurality of electrodes comprises:

implanting at least one cannulated structure into the boney tissue and across the bone fracture, the cannulated structure having a lumen extending at least partially therethrough; and
after implanting the cannulated structure, inserting an electronics cartridge into the lumen, the electronics cartridge including a sensing module.

200. The method of embodiment 199, wherein the plurality of electrodes are carried by the cannulated structure, and couple to the sensing module upon insertion of the electronics cartridge into the lumen.

201. The method of embodiment 199, wherein the plurality of electrodes are carried by the electronics cartridge, and interface with boney tissue through a plurality of apertures in a sidewall of the cannulated structure.

202. The method of embodiment 199, further comprising securing the electronics cartridge to the cannulated structure.

203. The method of embodiment 198, wherein implanting the plurality of electrodes comprises:
implanting a medical device including a structure carrying the plurality of electrodes, and electronics located in the structure and coupled to the plurality of electrodes.

204. A method of characterizing a bone fracture, the method comprising:
obtaining a plurality of measures of an electrical property of tissue overtime through a plurality of electrodes located in a boney tissue at a bone fracture, the plurality of electrodes including a first electrode and a second electrode, each within a gap of the bone fracture; and
processing the measures to determine a characterization of a bone fracture, the characterization corresponding to a healing state of the bone fracture.

205. The method of embodiment 204, wherein the healing state corresponds to one of union, likely non-union, and non-union.

206. The method of embodiment 204, further comprising communicating the plurality of measures of an electrical property of tissue, or the characterization of a bone fracture to an external device.

207. The method of embodiment 204, wherein the electrical property of tissue comprises impedance, and obtaining a plurality of measures comprises:
applying signals at different frequencies to the first electrode to measure tissue impedance in accordance with electrical impedance spectroscopy (EIS) techniques.

208. The method of 207, wherein the signals are applied by an implanted sensing module.

209. The method of embodiment 204, further comprising implanting the plurality of electrodes to place the first electrode and the second electrode within the gap of the bone fracture.

210. The method of embodiment 209, wherein implanting the plurality of electrodes comprises:
implanting at least one cannulated structure into the boney tissue and across the gap of the bone fracture, the cannulated structure having a lumen extending at least partially therethrough; and
after implanting the cannulated structure, inserting an electronics cartridge into the lumen, the electronics cartridge including a sensing module.

211. The method of embodiment 210, wherein the plurality of electrodes are carried by the cannulated structure, and couple to the sensing module upon insertion of the electronics cartridge into the lumen.

212. The method of embodiment 210, wherein the plurality of electrodes are carried by the electronics cartridge, and interface with boney tissue through a plurality of apertures in a sidewall of the cannulated structure.

213. The method of embodiment 210, further comprising securing the electronics cartridge to the cannulated structure.

214. The method of embodiment 209, wherein implanting the plurality of electrodes comprises:
implanting a medical device including a structure carrying the plurality of electrodes, and electronics located in the structure and coupled to the plurality of electrodes.

215. A method of characterizing a bone fracture, the method comprising:
obtaining a plurality of measures of an electrical property of tissue overtime through a plurality of electrodes located in a boney tissue at a bone fracture, the plurality of electrodes including a first electrode and a second electrode, each spanning a gap of the bone fracture; and
processing the measures to determine a characterization of a bone fracture, the characterization corresponding to a healing state of the bone fracture;
where optionally the plurality of measures is performed with a medical device according to any of embodiments 1-192, 226-238 and 262-263.

216. The method of embodiment 215, wherein the healing state corresponds to one of union, likely non-union, and non-union.

217. The method of embodiment 215, further comprising communicating the plurality of measures of an electrical property of tissue, or the characterization of a bone fracture to an external device.

218. The method of embodiment 215, wherein the electrical property of tissue comprises impedance, and obtaining a plurality of measures comprises:
applying signals at different frequencies to the first electrode to measure tissue impedance in accordance with electrical impedance spectroscopy (EIS) techniques.

219. The method of 218, wherein the signals are applied by an implanted sensing module.

220. The method of embodiment 215, further comprising implanting the plurality of electrodes to place the first electrode and the second electrode to span the gap of the bone fracture.

221. The method of embodiment 220, wherein implanting the plurality of electrodes comprises:
implanting at least one cannulated structure into the boney tissue and across the gap of the bone fracture, the cannulated structure having a lumen extending at least partially therethrough; and
after implanting the cannulated structure, inserting an electronics cartridge into the lumen, the electronics cartridge including a sensing module.

222. The method of embodiment 221, wherein the plurality of electrodes are carried by the cannulated structure, and couple to the sensing module upon insertion of the electronics cartridge into the lumen.

223. The method of embodiment 221, wherein the plurality of electrodes are carried by the electronics cartridge, and interface with boney tissue through a plurality of apertures in a sidewall of the cannulated structure.

224. The method of embodiment 221, further comprising securing the electronics cartridge to the cannulated structure.

225. The method of embodiment 220, wherein implanting the plurality of electrodes comprises:
implanting a medical device including a structure carrying the plurality of electrodes, and electronics located in the structure and coupled to the plurality of electrodes.

226. An implantable medical device for characterizing a bone fracture in a bone, the medical device comprising:
a first implant configured to be at least partially implanted in the bone, the first implant having a first electrode;
a second implant configured to be at least partially implanted in the bone, the second implant having a second electrode;
a third implant configured to be placed on the bone across the bone fracture and secured in place by the first implant and the second implant;
an impedance sensor comprised of:
the first electrode and the second electrode; and
a sensing module included in one of the first, second or third implants and configured to obtain impedance measurements between the first electrode and the second electrode;
a controller and memory included in one of the first, second or third implants and configured to process and store the impedance measurements; and
communication circuitry included in one of the first, second or third implants and configured to transmit the impedance measurements to an external device.

227. The medical device of embodiment 226, wherein the third implant is configured to allow for coupling of the first implant and the second implant at respective locations along the third implant that place the first electrode and the second electrode on opposite sides of the bone fracture.

228. The medical device of embodiment 226, wherein the sensing module is configured to enable the first electrode and the second electrode to function in either of an application mode during which a signal is applied across the first electrode and the second electrode, or a sensing mode during which an impedance between the first electrode and the second electrode is sensed.

229. The medical device of embodiment 228, wherein the sensing module comprises a signal generator configured to apply signals at different frequencies to measure tissue impedance in accordance with electrical impedance spectroscopy (EIS) techniques.

230. The medical device of embodiment 226, wherein the controller is further configured to process impedance measurements overtime to determine a characterization of the bone fracture, the characterization corresponding to a healing state of the bone fracture.

231. The medical device of embodiment 230, wherein the healing state corresponds to one of union, likely non-union, and non-union.

232. The medical device of embodiment 226, wherein the communication circuitry comprises tissue conductive communication circuitry coupled to the first electrode and the second electrode and configured to enable capacitive coupling between the medical device and another other device, or to enable galvanic coupling between the medical device and another device.

233. The medical device of embodiment 226, wherein at least one of the first implant and the second implant comprises:
   a structure having a lumen extending at least partially therethrough, and configured to be at least partially implanted in the bone and across the bone fracture; and
   an electronics cartridge including at least a portion of the impedance sensor, the controller, the memory, and at least a portion of the communication circuitry, the electronics cartridge configured to be inserted into the lumen after implant of the structure.

234. The medical device of embodiment 233, wherein the structure comprises an exterior surface and the first electrode or the second electrode are at the exterior surface.

235. The medical device of embodiment 233, wherein:
   the structure comprises at least one aperture through a sidewall; and
   the electronics cartridge comprises an exterior surface and the first electrode or the second electrode are at the exterior surface and positioned to align with the at least one aperture when the electronics cartridge is inserted into the lumen of the structure.

236. The medical device of embodiment 233, wherein the structure is a screw, pin, rod, nail, a part of a joint replacement implant, a part of a spinal fixation device, or a part of other orthopedic devices.

237. The medical device of embodiment 228, wherein at least one of the first implant and the second implant comprises a single structure.

238. The medical device of embodiment 237, wherein the single structure is a screw, pin, rod, nail, a part of a joint replacement implant, a part of a spinal fixation device, or a part of other orthopedic devices.

239. A method of manufacturing an implantable medical device, the method comprising:
   creating a plurality of apertures through a sidewall of a cannulated structure configured to be at least partially implanted in a body and having a lumen extending therethrough;
   associating an electrode with each of the plurality of apertures; and
   associating an electronics cartridge with the lumen of the cannulated structure, the electronics cartridge including electronics and a plurality of electrical contacts, wherein the associating aligns each of the plurality of electrical contacts with one of the apertures to establish an electrical coupling between the electronics and each electrode;
   where optionally the manufactured medical device is a medical device according to any of embodiments 1-192, 226-238 and 262-263.

240. The method of embodiment 239, wherein the cannulated structure comprises an electrically conductive material, and associating an electrode with each of the plurality of apertures comprises:
   applying an electrically insulating material to the cannulated structure in an area of each of the plurality of apertures; and
   applying an electrically conductive material over the electrically insulating material in an area of each of the plurality of apertures.

241. The method of embodiment 239, wherein the cannulated structure comprises an electrically insulative material, and associating an electrode with each of the plurality of apertures comprises:
   applying an electrically conductive material over surfaces of the cannulated structure in an area of each of the plurality of apertures.

242. The method of embodiment 239, wherein the cannulated structure comprises an electrically conductive material, and associating an electrode with each of the plurality of apertures comprises:
   applying an electrically insulating material to the cannulated structure in an area of each of the plurality of apertures; and
   placing an electrically conductive structure through each of the plurality of apertures.

243. The method of embodiment 242, wherein placing an electrically conductive structure comprises inserting a conductive pin through each of the plurality of apertures.

244. The method of embodiment 242, wherein placing an electrically conductive structure comprises filling each of the plurality of apertures with an electrically conductive material.

245. The method of embodiment 239, wherein the cannulated structure comprises an electrically insulative material, and associating an electrode with each of the plurality of apertures comprises at least one of:
   inserting a conductive pin through each of the plurality of apertures; and
   filling each of the plurality of apertures with an electrically conductive material.

246. A method of implanting a medical device, the method comprising:
   implanting an implant structure at least partially in a body, the implant structure having a lumen extending at least partially therethrough; and
   after implanting the implant structure, inserting an electronics cartridge into the lumen.

247. The method of embodiment 246, wherein the implant structure comprises a proximal end having a head, and a shaft extending from the head to a distal end of the implant structure, and implanting the implant structure comprises:
   inserting a support structure into the shaft and at least partially along a length of the lumen; and
   rotating the support structure together with the implant structure.

248. The method of embodiment 247, wherein rotating the support structure together with the implant structure comprises transmitting rotational torque from the support structure to a portion of the shaft.

249. The method of embodiment 248, wherein the shaft and the support structure are configured to mechanically couple to enable a direct transmission of rotational torque to the shaft.

250. The method of embodiment 247, further comprising, prior to inserting a support structure, placing the implant structure over a guidewire placed across a bone fracture.

251. The method of embodiment 246, wherein the implant structure comprises a proximal end having a head, and a shaft extending from the head to a distal end of the implant structure, and implanting the implant structure comprises:
   placing the implant structure in a coupling device comprising a body configured to establish a mechanical coupling with a distal end portion of the implant structure; and rotating the coupling device together with the implant structure.
252. The method of embodiment 251, wherein rotating the coupling device together with the implant structure comprises transmitting rotational torque along a length of the body to the mechanical coupling and to distal end portion of the implant structure.
253. The method of embodiment 252, wherein the coupling device couples to the implant structure only at the distal end portion of the implant structure.
254. The method of embodiment 246, further comprising securing the electronics cartridge to the implant structure.
255. The method of embodiment 254, further comprising: after securing the electronics cartridge to the implant structure, removing the electronics cartridge from the lumen without affecting the structural integrity of the implant structure or the electronics cartridge.
256. The method of embodiment 255, further comprising: after removing the electronics cartridge from the lumen, inserting a replacement electronics cartridge in the lumen of the implant structure.
257. A tool for implanting an implant structure having a proximal end having a head, a shaft extending from the head to a distal end of the implant structure, and a lumen extending through the shaft, the tool comprising:
a drill bit; and
a mechanism for applying rotational torque to the drill bit,
wherein the drill bit comprises:
a first portion configured to directly couple to the head of the implant structure; and
a second portion extending from the first portion, the second portion configured to extend at least partially into the lumen of the implant structure.
258. The tool of embodiment 257, wherein the second portion comprises a mechanical feature configured to mechanically couple with a corresponding feature of the shaft to thereby enable transmission of rotational torque from the second portion to the shaft.
259. A coupling device for implanting an implant structure having a proximal end having a head, and a shaft extending from the head to a distal end of the implant structure, the coupling device comprising:
a body having a proximal end region and a distal end region configured to establish a mechanical coupling to a distal end portion of the implant structure; and
a cap configured to the couple to the proximal end region of the body without directly coupling to the implant structure.
260. The coupling device of embodiment 259, wherein: the cap is configured to couple to a tool, receive rotational torque from the tool through the coupling, and transmit rotational torque along a length of the body to the mechanical coupling and to the distal end portion of the implant structure.
261. The coupling device of embodiment 259, wherein the coupling device is configured to couple to the implant structure only at the distal end portion of the implant structure.
262. The medical device of any of embodiments 1-192 and 226-238, wherein the medical device is sterile.
263. The medical device of any of embodiments 1-192 and 226-238, wherein the medical device has been subjected to a sterilization procedure to provide a sterile medical device.
264. A method of treating a fracture in boney tissue, the method comprising identifying a fracture in boney tissue, and inserting a medical device according to any of embodiments 1-192, 226-238 and 262-263 into the bony tissue, where the medical device is inserted across the fracture.
265. The method of embodiment 264 wherein the medical device is a medical device according to any of embodiments 1-76.
266. The method of embodiment 264 wherein the medical device is a medical device according to any of embodiments 77-94.
267. The method of embodiment 264 wherein the medical device is a medical device according to any of embodiments 95-101.
268. The method of embodiment 264 wherein the medical device is a medical device according to any of embodiments 102-104.
269. The method of embodiment 264 wherein the medical device is a medical device according to any of embodiments 105-108.
270. The method of embodiment 264 wherein the medical device is a medical device according to any of embodiments 109-164.
271. The method of embodiment 264 wherein the medical device is a medical device according to any of embodiments 165-176.
272. The method of embodiment 264 wherein the medical device is a medical device according to any of embodiments 177-192.
273. The method of embodiment 264 wherein the medical device is a medical device according to any of embodiments 226-238.
274. The method of embodiment 264 wherein the medical device is a medical device according to any of embodiments 262-263.
275. The method of any embodiments 264-274 wherein the medical device is a screw.
276. The method of any of embodiments 264-275 further comprising characterizing the fraction with the medical device.
277. A method of characterizing a fracture in boney tissue, the method comprising identifying a fracture in boney tissue, inserting a medical device according to any of embodiments 1-192, 226-238 and 262-263 into the bony tissue, where the medical device is inserted across the fracture; and characterizing the fracture with a sensor located in the medical device.
278. The method of embodiment 277 wherein the medical device is a medical device according to any of embodiments 1-76.
279. The method of embodiment 277 wherein the medical device is a medical device according to any of embodiments 77-94.
280. The method of embodiment 277 wherein the medical device is a medical device according to any of embodiments 95-101.
281. The method of embodiment 277 wherein the medical device is a medical device according to any of embodiments 102-104.
282. The method of embodiment 277 wherein the medical device is a medical device according to any of embodiments 105-108.
283. The method of embodiment 277 wherein the medical device is a medical device according to any of embodiments 109-164.

284. The method of embodiment 277 wherein the medical device is a medical device according to any of embodiments 165-176.
285. The method of embodiment 277 wherein the medical device is a medical device according to any of embodiments 177-192.
286. The method of embodiment 277 wherein the medical device is a medical device according to any of embodiments 226-238.
287. The method of embodiment 277 wherein the medical device is a medical device according to any of embodiments 262-263.
288. The method according to any of embodiments 277-287 wherein the medical device is a screw.
289. A set of medical devices, the set comprising at least one first medical device according to any of embodiments 1-192, 226-238 and 262-263, the set further comprising at least one second medical device configured for insertion into boney tissue, where the second medical device does not contain a sensor.
290. The set of medical devices of embodiment 289 wherein each of the first medical device and the second medical device is a screw.
291. The set of medical devices of embodiment 289 comprising a single first medical device and a plurality of second medical devices.
292. The set of medical devices of embodiment 291 wherein each member of the set is a screw.

The various aspects of this disclosure are provided to enable one of ordinary skill in the art to practice the embodiments. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the present disclosure are described in terms of Markush groups, it is intended, and those skilled in the art will recognize, that the present disclosure embraces and is also thereby described in terms of any individual member and any subgroup of members of the Markush group, and Applicants reserve the right to revise the application or claims to refer specifically to any individual member or any subgroup of members of the Markush group.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents, i.e., one or more, unless the content and context clearly dictates otherwise. For example, the term "a sensor" refers to one or more sensors, and the term "a medical device comprising a sensor" is a reference to a medical device that includes at least one sensor, where the medical device comprising a sensor may have, for example, 1 sensor, 2 sensors, 3 sensors, 4 sensors, 5 sensors, 6 sensors, 7 sensors, 8 sensors, 9 sensors, 10 sensors, or more than 10 sensors. A plurality of sensors refers to more than one sensor. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claims.

Any headings used within this document are only being utilized to expedite its review by the reader, and should not be construed as limiting the disclosure, invention or claims in any manner. Thus, the headings and Abstract of the Disclosure provided herein are for convenience only and do not interpret the scope or meaning of the embodiments.

Where a range of values is provided herein, it is understood that each intervening value, to the tenth of the unit of the lower limit unless the context clearly dictates otherwise, between the upper and lower limit of that range and any other stated or intervening value in that stated range is encompassed within the disclosure, invention or claims. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Such documents may be incorporated by reference for the purpose of describing and disclosing, for example, materials and methodologies described in the publications, which might be used in connection with the present disclosure. The publications discussed above and throughout the text are provided solely for their disclosure prior to the filing date of the present application. Nothing herein is to be construed as an admission that the inventors are not entitled to antedate any referenced publication by virtue of prior invention.

All patents, publications, scientific articles, web sites, and other documents and materials referenced or mentioned herein are indicative of the levels of skill of those skilled in the art to which the disclosure pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Furthermore, the written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

Other nonlimiting embodiments are within the following claims. The patent may not be interpreted to be limited to the specific examples or nonlimiting embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A medical device comprising:
  a structure having a lumen extending at least partially therethrough, and configured to be at least partially implanted in a body;
  an electronics cartridge including electronics and configured to be inserted into the lumen after implant of the structure; and
  a sensor for measuring an electrical property of tissue, the sensor comprising:
  a plurality of electrodes; and
  a sensing module of the electronics cartridge, coupled to the plurality of electrodes; wherein
  the plurality of electrodes comprises a first electrode and a second electrode; and
  the sensing module is configured to enable the first electrode and the second electrode to function in either of an application mode during which a signal is applied across the electrodes, or a sensing mode during which an impedance between the electrodes is sensed.

2. The medical device of claim 1, wherein the sensing module comprises a signal generator configured to apply signals at different frequencies to measure tissue impedance in accordance with electrical impedance spectroscopy (EIS) techniques.

3. The medical device of claim 1, wherein:
  the sensor further comprises an electrode switch;
  the plurality of electrodes further comprises a third electrode and a fourth electrode switchably coupled to the sensing module through the electrode switch; and
  the sensing module is further configured to enable a sensing mode during which an impedance between the third electrode and the fourth electrode is sensed.

4. The medical device of claim 3, wherein the sensing module comprises a signal generator configured to apply signals at different frequencies to measure tissue impedance in accordance with electrical impedance spectroscopy (EIS) techniques.

5. The medical device of claim 1, wherein the electrical property of tissue comprises impedance measurements, and further comprising a controller configured to process impedance measurements over time to determine a characterization of a bone fracture, the characterization corresponding to a healing state of the bone fracture.

6. The medical device of claim 5, wherein the healing state corresponds to one of union, likely non-union, and non-union.

7. The medical device of claim 1, wherein:
  the plurality of electrodes are associated with the structure and spaced apart to enable placement of the first electrode and the second electrode on opposite sides of a bone fracture; and
  the electronics cartridge comprises a plurality of electrical contacts located to electrically couple with the plurality of electrodes when the electronics cartridge is inserted into the lumen of the structure.

8. The medical device of claim 1, wherein:
  the plurality of electrodes are associated with the electronics cartridge and spaced apart to enable placement of the first electrode and the second electrode on opposite sides of a bone fracture.

* * * * *